United States Patent
Kim et al.

(10) Patent No.: US 11,068,561 B2
(45) Date of Patent: Jul. 20, 2021

(54) REDUCED MODELING METHOD FOR NEURONS

(71) Applicant: DAEGU GYEONGBUK INSTITUTE OF SCIENCE AND TECHNOLOGY, Daegu (KR)

(72) Inventors: Ho Jeong Kim, Daegu (KR); Kelvin E. Jones, Alberta (CA)

(73) Assignee: DAEGU GYEONGBUK INSTITUTE OF SCIENCE AND TECHNOLOGY, Daegu (KR)

(*) Notice: Subject to any disclaimer, the term of this patent is extended or adjusted under 35 U.S.C. 154(b) by 399 days.

(21) Appl. No.: 14/679,383

(22) Filed: Apr. 6, 2015

(65) Prior Publication Data
US 2015/0356267 A1 Dec. 10, 2015

(30) Foreign Application Priority Data
Jun. 10, 2014 (KR) .......................... 10-2014-0070324

(51) Int. Cl.
*G06F 17/10* (2006.01)
*G16H 50/50* (2018.01)
*G06F 30/20* (2020.01)
*G06F 111/10* (2020.01)

(52) U.S. Cl.
CPC .............. *G06F 17/10* (2013.01); *G16H 50/50* (2018.01); *G06F 30/20* (2020.01); *G06F 2111/10* (2020.01)

(58) Field of Classification Search
CPC .............. A61B 5/4041; A61B 1/00135; A61N 1/36021; A01N 1/02; A61K 31/137; G06F 17/10; G06F 30/20; G06F 2111/10; G16H 50/50
See application file for complete search history.

(56) References Cited

U.S. PATENT DOCUMENTS

| | | | |
|---|---|---|---|
| 6,723,698 B2* | 4/2004 | Rueger | A01N 1/02 514/17.7 |
| 2007/0053996 A1* | 3/2007 | Boyden | A61K 31/137 424/718 |
| 2012/0101336 A1* | 4/2012 | Hirsch | A61B 1/00135 600/156 |

(Continued)

OTHER PUBLICATIONS

Michael London et al., Dendritic Computation, book, 2005, pp. 503-532, Annual Reviews, Republic of Korea.

(Continued)

*Primary Examiner* — Kandasamy Thangavelu
(74) *Attorney, Agent, or Firm* — Harness, Dickey & Pierce, P.L.C.

(57) ABSTRACT

Disclosed herein is modeling method which is enabled to analyses neurons in order to reduce real neurons physiologically properly using the relationship between asymmetry in signal propagation between a soma and dendrites and dendritic excitability. The modeling method for neurons include determining voltage attenuation factors which represent properties of signal propagation between dendrites and a soma and is represented as functions of distance from the soma; and determining a plurality of passive parameter at a pre-determined path length using system parameters defined from the anatomical model comprising the voltage attenuation factors at the pre-determined path length.

18 Claims, 38 Drawing Sheets

(56) References Cited

U.S. PATENT DOCUMENTS

| | | | | |
|---|---|---|---|---|
| 2014/0324118 A1* | 10/2014 | Simon | ............... | A61N 1/36021 607/46 |
| 2014/0336479 A1* | 11/2014 | Ando | ................ | A61B 5/4041 600/310 |

OTHER PUBLICATIONS

Albert Gidon et al., Principles Governing the Operation of Synaptic Inhibition in Dendrites, article, May 15, 2012, pp. 330-311, Elsevier Inc., Jerusalem, Israel.

R.H. Lee et al., Influence of Active Dendritic Currents on Input-Output Processing in Spinal Motoneurons In Vivo, journal, 2003, pp. 27-39, American Physiological Society, Berthesda, MD.

C.J. Heckman et al., Hyperexcitable dendrites in motoneurons and their neuromodulatory control during motor behavior, book, 2003, pp. 688-695, vol. 26; No. 12, Elsevier Ltd.

Wilfrid Rall, Theory of Physiological Properties of Dendrites, paper, pp. 1071-1092, Annals New York Academy of Sciences.

Dan Bar-Yehuda et al., Space-Clamp Problems When Voltage Clamping Neurons Expressing Voltage-Gated Conductances, journal, Jan. 8, 2008, pp. 1127-1136, American Physiological Soceity, Bethesda, MD.

W. Mueller et al., Analysis of Voltage-Dependent Membrane Currents in Spatially Extended Neurons From Point-Clamp Data, journal, 1993, pp. 241-247, The American Physiological Society, Berthesda, MD.

Kevin P. Carlin et al., Staircase Currents in Motoneurons: Insight into the Spatial Arrangement of Calcium Channels in the Dendritic Tree, journal, Apr. 22, 2009, pp. 5343-5353, Society for Neuroscience.

Zachary F. Mainen et al., Influence of dendetritic structure on filing pattern in model neocortical neurons, book, Jul. 25, 1996, pp. 363-366, vol. 382.

Reza Zomorrodi et al., Modeling thalamocortical cell: impaft of $Ca^2+$ channel distribution and cell geometry on firing pattern, article, Dec. 12, 2008, pp. 1-11, vol. 2, article 5, Frontiers Research Foundation, Quebec, Canada.

Michael Hauser et al., Diversity and Dynamics of Dendritic Signaling, book, Oct. 27, 2000, pp. 739-744, vol. 290, American Association for the Advancement of Science.

Idan Segev et al., Untangling Dendrites with Quantitative Models, book, Oct. 27, 2000, pp. 744-750, vol. 290, American Association for Advacement of Science.

Wilfrid Rall et al., Branch Input Resistance and Steady Attenuation for Input to One Branch of a dendritic Neuron Model, journal, 1973, pp. 648-688, vol. 13, Biophysical Journal.

Nicholas T. Carnevale et al., Electrophysiological Characterization of Remote Chemical Synapses, journal, Apr. 1982, pp. 606-621, vol. 47, No. 4, Journal of Neurophysiology, USA.

Anthony M. Zador et al., The Morphoelectronic Transform: A Graphical Approach to Dendritic Function, journal, Mar. 1995, pp. 1669-1682, Society of Neuroscience.

Hojeong Kim et al., Asymmetric electrotonic coupling between the soma and dendrites alters the bistable firing behaviour of reduced models, journal, 2010, pp. 659-674, Springer Science+Business Media, LLC, Alberta, CA.

Hojeong Kim et al., The Retrograde Frequency Response of Passive Dendritic Trees Constrains the Nonlinear Firing Behaviour of a Reduced Neuron Model, article, Aug. 2012, pp. 1-15, vol. 7, Issue 8, Kim Jones.

Giorgio A. Ascoli, Mobilizing the base of neuroscience data: the case of neuronal morphologies, journal, Apr. 2006, pp. 318-324, vol. 7.

M.L. Hines et al., The Neuron Simulation Environment, journal, pp. 1179-1209, Neural Computation 9, Massachusetts Institute of Technology, Massachusetts.

Hojeong Kim et al., Derivation of cable parametesr for a reduced model that retrains asymmetric voltage attenuation of reconstructed spinal motor neuron dendrites, article, 2009, pp. 321-336, Springer Science + Business Media, LLC, Alberta, Canada.

S. Cullheim et al., Membrane Area and Dendritic Structure in Type-Identified Triceps Surae Alpha Motoneurons, journal, 1987, pp. 68-81, Alan R. Liss, Inc.

James W. Fleshman et al., Electronic Architecture of Type-Identified α-Motoneurons in the Cat Spinal Cord, journal, 1988, pp. 60-85, vol. 60, No. 1, Journal of Neurophysiology, USA.

Idan Segev et al., Computer Simulation of Group la EPSPs Using Morphologically Realistic Models of cat α-Motoneurons, journal, 1990, pp. 648-660, vol. 64, No. 2, Journal of Neurophysiology, USA.

William R. Holmes et al., Electronic Length Estimates in Neurons with Dendritic Tapering of Somatic Shunt, journal, 1992, pp. 1421-1437, Journal of Neurophysiology, USA.

David Thurbon et al., Passive Electrical Properties of Ventral Horn Neurons in Rat Spinal Cord Slices, journal, 1998, pp. 2485-2502, American Physiological Society, Bethesda, MD.

Guy Major et al., Solutions for Transients in Arbitrarily Branching Cables: I. Voltage Recording with a Somatic Shunt, journal, Jul. 1993, pp. 423-449, Biophysical Society, Oxford, UK.

J.S. Coombs et al., The Electrical Properties of the Motoneurone Membrane, journal, 1955, pp. 291-325, J. Physiol, Canberra, Australia.

Sherif M. Elbasiouny et al., Simulation of Dendritic $Ca_v1.3$ Channels in Cat Lumbar Motorneurons: Spatial Distribution, journal, Aug. 25, 2005, pp. 3961-3974, The American Physiological Society, Canada.

Tuan V. Bui et al., Computational Estimation of the Distribution of L-type $Ca^{2+}$Channels in Motoneurons Based on Variable Threshold of Activation of Persistent Inward Currents, journal, 2006, pp. 225-241, American Physiological Society, Bethesda, MD.

S. Hochman et al., Effects of Chronic Spinalization on Ankle Extensor Motoneurons II. Motoneuron Electrical Properties, journal, Apr. 4, 1994, pp. 1468-1479, vol. 71, No. 4, The American Physiological Society, Bethesda, MD.

R.H. Lee et al., Paradoxical Effect of QX-314 on Persistent Inward Currents and Bistable Behavior in Spinal Motoneurons In Vivo, journal, 1999, pp. 2518-2527, The American Physiological Society, Bethesda, MD.

Sherif M. Elbasiouny et al., Simulation of $Ca^{2+}$persistent inward currents in spinal motoneurones: mode of activation and integration of synaptic inputs, journal, 2006, pp. 355-374, The Authors; The Physiological Society.

Jørn Hounsgaard et al., Serotonin-Induced Bistability of Turtle Motoneurones caused by a Nifedipine-Sensitive Calcium Plateau Potential, journal, 1989, pp. 265-282, Journal of Physiology, Great Britian.

Yunru Li et al., Persistent Sodium and Calcium Currents Cause Plateau Potentials in Motoneurons of Chronic Spinal Rats, journal, 2003, pp. 857-869, The American Physiological Society, Bethesda, MD.

C. F. Meehan et al., Intrinsic Properties of Mouse Lumbar Motoneurons Revealed by Intracellular Recording In Vivo, journal, 2010, pp. 2599-2610, The American Physiological Society, Bethesda, MD.

R.H. Lee et al., Bistability in Spinal Motoneurons In Vivo: Systematic Variations in Persistent Inward Currents, journal, 1998, pp. 583-593, The American Physiological Society, Bethesda, MD.

David J. Bennett et al., Synaptic Activation of Plateaus in Hindlimb Motorneurons of Decerebrate Cats, journal, 1998, pp. 2023-2037, The American Physiological Society, Bethesda, MD.

K. P. Carlin et al., Dendritic L-type calcium currents in mouse spinal motoneurons: implication for bistability, journal, 2000, pp. 1635-1646, vol. 12, European Neuroscience Association.

Victoria Booth et al., A Minimal, Compartmental Model for a Dendritic Origin of Bistability of Motoneuron Firing Patterns, journal, 1995, pp. 299-312, Kluwer Academic Publishers, Boston, MA.

Edmund W. Ballou et al., Measuring dendritic distribution of membrane proteins, journal, 2006, pp. 257-266, Elsevier B.V.

(56) References Cited

OTHER PUBLICATIONS

Anna T. Moritz et al., Facilitation of Somatic Calcium Channels Can Evoke Prolonged Tail Currents in Rat Hypoglossal Motoneurons, journal, 2007, pp. 1042-1047, The American Physiological Society, Bethesda, MD.

David J. Bennett et al., Plateau Potentials in Sacrocaudal Motoneurons of Chronic Spinal Rats, Recorded In Vitro, journal, 2001, pp. 1955-1971, The American Physiological Society, Bethesda, MD.

Janet E. Zengel et al., Membrance Electrical Properties and Prediction of Motor-Unit Type of Medial Gastrocnemius Motorneurons in the Cat, journal, 1985, pp. 1322-1344, The American Physiological Society, Bethesda, MD.

Alan Destexhe et al., Impact of Network Activity on the Integrative Properties of Neocortical Pyramidal Neurons In Vivo, journal, 1999, pp. 1531-1547, The American Physiological Society, Bethesda, MD.

Stephen R. Williams, Spatial compartmentalization and functional impact of conductance in pyramidal neurons, article, Sep. 2004, pp. 961-967, vol. 7, No. 9, Nature Publishing Group.

Steve A. N. Goldstein et al., Potassium Leak Channels and the KCNK Family of Two-P-Domain Subunits, article, Mar. 2001, pp. 175-184, vol. 2, Macmillan Magazines Ltd.

Roger A. Nicoll et al., Functional Comparison of Neurotransmitter Receptor Subtypes in Mammalian Central Nervous System, journal, 1990, pp. 513-565, The American Physiological Society, Bethesda, MD.

Masahito Yamade et al., A Quantitative Golgi study of basal dendrites of hippocampal CA1 pyramidal cells in senile dementia of Alzheimer type, journal/report, 1988, pp. 10-88-1090, Journal of Neurology, Neurosurgery, and Psychiatry.

G. Campbell Teskey et al., Neocortical Kindling is Associated With Opposing Alterations in Dendritic Morphology in Neocortical Layer V and Striatum From Neocortical Layer III, journal, 2005, pp. 1-9, Wiley-Liss, Inc., Alberta, CA.

N. Sousa et al, Reorganization of the Morphology of Hippocampal Neurites and Synapses After Stress-Induced Damage Correlates with Behavioral Improvement, article, 2000, pp. 253-266, Elsevier Science Ltd.

Natalie R. Krenz et al., Changes in the morphology of sympathetic preganglionic neurons parallel the development of autonomic dysreflexia after spinal cord injury in rats, journal, 1998, pp. 61-64, Elsevier Science Ireland Ltd.

Ronald A. J. Can Elburg et al., Impact of Dendritic Topology on Burst Firing in Pyramidal Cells, journal, May 2010, pp. 1-19, vol. 6, Issue 5, van Elburg, van Ooyen.

Jeffrey L. Krichmar et al., Effects of dendritic morphology on CA3 pyramidal cell electrophysiology: a simulation study, journal, 2002, pp. 11-28, Elsevier Science B.V.

Paul F. Pinsky et al., Intrinsic and Network Rhythmogenesis in a Reduced Traub Model for CA3 Neurons, journal, 1994, pp. 39-60, Kluwer Academic Publishers, The Netherlands.

J.D. Clements et al., Cable Properties of Cat Spinal Motoneurons Measured by Combining Voltage Clamp, Current Clamp and Intracellular Staining, journal, 1989, pp. 63-87, Journal of Physiology, Great Britain.

Paul C. Bush et al., Reduced compartmental models of neocortical pyramidal cells, journal, 1993, pp. 159-166, Elsevier Science Publishers B.V.

Eric B. Hendrickson et al., The capabilities and limitations of conductance-based compartmental neuron models with reduced branched or unbranched morphologies and active dendrites, article, 2011, pp. 301-321, The Authors, Atlanta, GA.

Hysell Oviedo et al., Variation of Input—Output Properties along the Somatodendritic Axis of Pyramidal Neurons, The Journal of Neuroscience, May 18, 2005, pp. 4985-4995, Society for Neuroscience, New York.

* cited by examiner

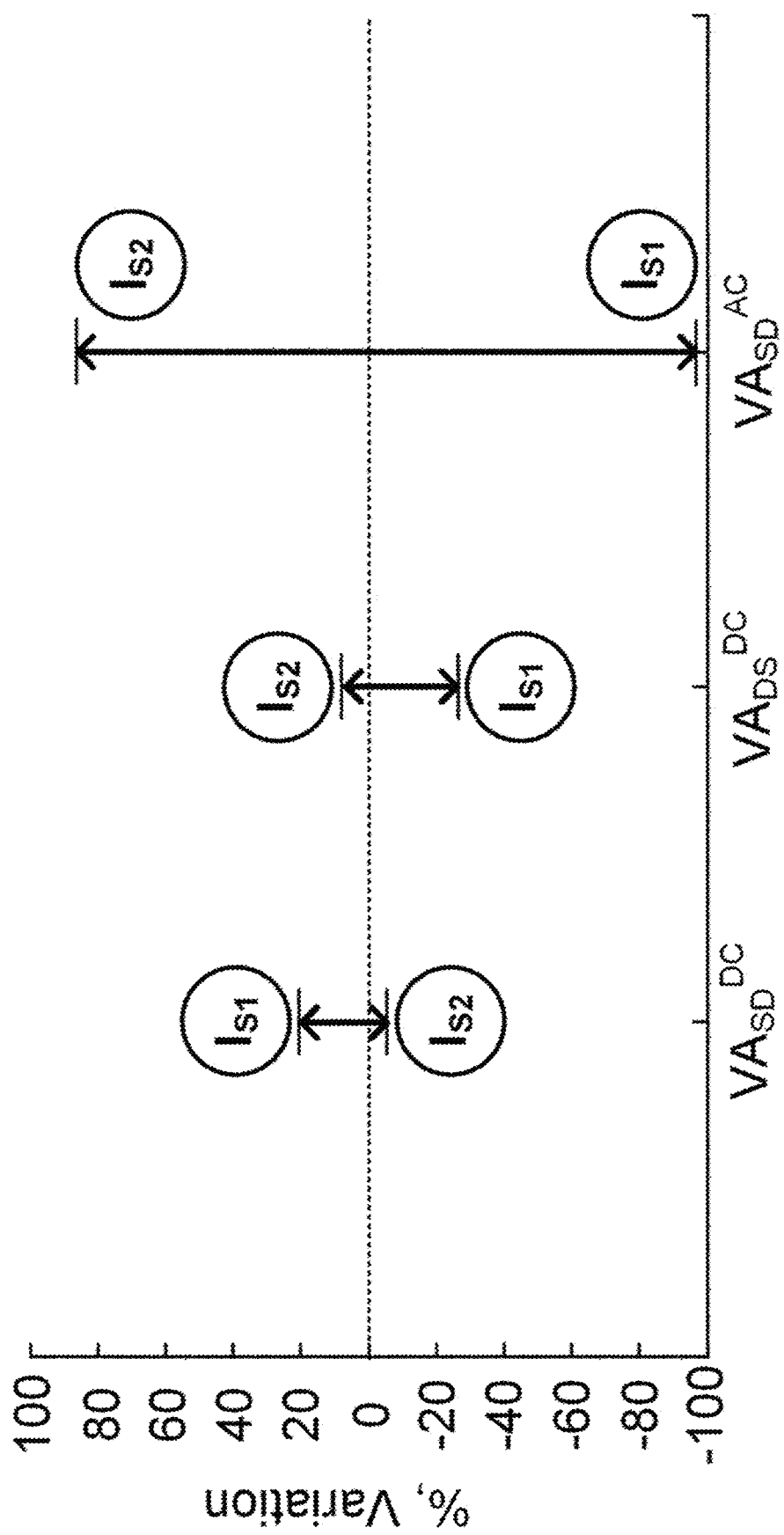

REDUCED MODELING METHOD FOR NEURONS

CROSS-REFERENCE TO RELATED PATENT APPLICATIONS

This patent application claims priority to Korean Application No. 10-2014-0070324, filed Jun. 10, 2014, the entire teachings and disclosure of which are incorporated herein by reference thereto.

BACKGROUND OF THE INVENTION

Field of the Invention

The present invention relates generally to reduced modeling method for neurons and, in more detail, to modeling method which is enabled to analyses neurons in order to reduce real neurons physiologically properly using the relationship between asymmetry in signal propagation between a soma and dendrites and dendritic excitability.

Description of the Related Art

Many neurons in the central nervous system have voltage gated ion channels (VGICs) in their dendrites. The activation of dendritic VGICs is location sensitive, leading to functional impacts on dendritic signaling and firing patterns [London M, Hausser M (2005) Dendritic computation. Annu Rev Neurosci 28: 503-532, Oviedo H, Reyes A D (2005) Variation of input-output properties along the somatodendritic axis of pyramidal neurons. J Neurosci 25: 4985-4995, Gidon A, Segev I (2012) Principles governing the operation of synaptic inhibition in dendrites. Neuron 75: 330-341, Lee R H, Kuo J J, Jiang M C, Heckman C J (2003) Influence of active dendritic currents on input-output processing in spinal motoneurons in vivo. J Neurophysiol 89: 27-39]. Therefore, an accurate understanding of the influence of the dendritic structure on the activation of dendritic VGICs is needed. In other words, dendritic structure influences not only the passive excitability of dendrites but also their "active" excitability (here we use the phrase "dendritic excitability" to refer primarily to the active component involving dendritic VGICs). The activation properties of dendritic VGICs were initially investigated using voltage or current clamp at the cell body. Since a command signal (voltage or current) applied to the soma attenuates along the path of the dendritic trees, due to their cable properties [Rall W (1962) Theory of physiological properties of dendrites. Ann N Y Acad Sci 96: 1071-1092], higher command signals are required to activate more distal VGICs. This effect gives rise to space-clamp as a potential confounding factor for interpretation of dendritic excitability [Bar-Yehuda D, Korngreen A (2008) Space-clamp problems when voltage clamping neurons expressing voltage-gated conductances. J Neurophysiol 99: 1127-1136; Muller W, Lux H D (1993) Analysis of voltage-dependent membrane currents in spatially extended neurons from point-clamp data. J Neurophysiol 69: 241-247]. Many studies using neuron models accounted for this confounding factor by characterizing the degree of signal attenuation from the soma to the dendrites, e.g. using a coupling conductance, as the key determinant for the location dependence of VGIC activation [Carlin K P, Bui TV, Dai Y, Brownstone R M (2009) Staircase currents in motoneurons: insight into the spatial arrangement of calcium channels in the dendritic tree. J Neurosci 29: 5343-5353; Mainen Z F, Sejnowski T J (1996) Influence of dendritic structure on firing pattern in model neocortical neurons. Nature 382: 363-366; Zomorrodi R, Kroger H, Timofeev I (2008) Modeling thalamocortical cell: impact of ca channel distribution and cell geometry on firing pattern. Front Comput Neurosci 2: 5].

However, studies focused on dendritic anatomy have demonstrated a more complex signal attenuation process exists between the soma and dendrites. Both experimental evidence [Hausser M, Spruston N, Stuart G J (2000)Diversity and dynamics 509 of dendritic signaling. Science 290: 739-744] and computational analyses [Segev I, London M (2000) Untangling dendrites with quantitative models. Science 290: 744-750; Rall W, Rinzel J (1973) Branch input resistance and steady attenuation for input to one branch of a dendritic neuron model. Biophys J 13: 648-687] have emphasized that the attenuation of electrical signals in dendrites is asymmetric with respect to propagation direction (i.e. soma to dendrites and vice versa), and is moderated by frequency (direct (DC) or alternating (AC) current). This direction and frequency dependent dendritic signaling has been analyzed using two-port circuit theory [Carnevale N T, Johnston D (1982) Electrophysiological characterization of remote chemical synapses. J Neurophysiol 47: 606-621] and morphoelectrotonic transformation of the anatomy of dendrites [Zador A M, Agmon-Snir H, Segev I (1995) The morphoelectrotonic transform: a graphical approach to dendritic function. J Neurosci 15: 1669-1682]. These studies suggested that a theoretical examination and understanding of dendritic excitability should go beyond the previous qualitative, or phenomenological, representation of DC signal attenuation from the soma to the dendrites. Furthermore, the previous analysis of dendritic signaling between the soma and a single point in the dendrites should be extended to reflect more natural conditions in which the VGICs or synaptic inputs are positioned on many dendrites.

It is widely recognized that propagation of electrophysiological signals between the soma and dendrites of neurons differs depending on direction, i.e. it is asymmetric. How this asymmetry influences the activation of voltage-gated dendritic channels, and consequent neuronal behavior, remains unclear.

Furthermore, the traditional modeling methods for neurons have limitations to model neuron realistically because they were developed in the abstract.

SUMMARY OF THE INVENTION

Accordingly, the present invention has been made keeping in mind the above problems occurring in the prior art, and an object of the present invention is to provide reduced modeling methods reflecting physiologically properties realistically in order to develop mathematical technique which determines experimental model parameter.

In order to accomplish the above object, the present invention provides reduced modeling method for neuron comprising: confirming asymmetry in signal propagation between a soma and dendrites of neuron which is modeled; confirming dendritic excitability of the neuron; identifying relationship between the asymmetry in signal propagation and the dendritic excitability; and determining the reduced modeling method of the neuron using the relationship between the asymmetry in signal propagation and the dendritic excitability.

The relationship between the asymmetry in signal propagation and the dendritic excitability may comprise: increasing in signal attenuation from soma to dendrites increase activation threshold of a persistent inward current (PIC) dispersed over the dendrites (hypo-excitability); and increasing in signal attenuation from dendrites to soma decrease the activation threshold of the PIC dispersed over the dendrites (hyper-excitability).

The asymmetry in the signal propagation may comprise spatial profiles of three voltage attenuation factors, wherein voltage attenuation factors have neuron voltage profiles in response to steady current injected at the soma ($VA_{SD}^{DC}$), action potentials propagating from the initial segment and the soma into the dendrites ($VA_{SD}^{AC}$), and steady synaptic inputs and plateau potential generated by VGICs in the dendrites ($VA_{DS}^{DC}$).

The $VA_{SD}^{DC}$, the $VA_{SD}^{AC}$ and the $VA_{DS}^{DC}$ may be determined using path length ($D_{path}$) from the soma according to equation 1 to 3 respectively as below:

$$VA_{SD}^{DC}(D_{path}) = \exp\left(-\frac{D_{path}}{\lambda_{SD}^{DC}}\right) \quad (1)$$

$$VA_{SD}^{AC}(D_{path}) = \exp\left(-\frac{D_{path}}{\lambda_{SD}^{AC}}\right) \quad (2)$$

$$VA_{DS}^{DC}(D_{path}) = \frac{1}{1 - \exp\left(\frac{-\alpha_1}{\alpha_2}\right) + \exp\left(\frac{D_{path} - \alpha_1}{\alpha_2}\right)}. \quad (3)$$

The asymmetry in the signal propagation may be quantified by a ratio ($VA_{SD}^{DC}/VA_{DS}^{DC}$) of DC voltage between the soma and a single point in the dendrites as below:

$R_{ND}(D_{path}) = R_N * VA_{SD}^{DC}(D_{path})/V_{DS}^{DC}(D_{path})$, wherein the $R_{N, D}$ is input resistance ($R_{N, D}$) at the same site of the dendrites.

In order to accomplish the above object, the present invention also provides reduced modeling method for neuron, comprising: determining voltage attenuation factors which represent properties of signal propagation between dendrites and a soma and is represented as functions of distance from the soma; and determining a plurality of passive parameter at a pre-determined path length using system parameters defined from the anatomical model comprising the voltage attenuation factors at the pre-determined path length.

The voltage attenuation factors may comprise $VA_{SD}^{DC}$ and $VA_{SD}^{AC}$ which are DC and AC component from soma to dendrites respectively, and $VA_{DS}^{DC}$ which is DC component from the dendrites to soma.

The voltage attenuation factors representing signal propagation of the dendrites may be defined as a ratio of voltage at measurement site to voltage at the current injection site in the passive membrane condition.

The $VA_{SD}^{DC}$ may be measured at dendrites for propagation of steady current injected at the soma.

The $VA_{DS}^{DC}$ may be measured for propagation of steady synaptic inputs and persistent inward current generated by voltage gated ion channels (VGICs) that are distributed over all branches of the dendrites at the same distance from the soma.

The $VA_{SD}^{AC}$ may be measured for action potentials propagating from initial segment and the soma into the dendrites.

The $VA_{SD}^{DC}$ and $VA_{SD}^{AC}$ may be fitted by single exponential function with voltage decay constant ($\lambda_{SD}^{DC}$ and $\lambda_{SD}^{AC}$).

The $VA_{SD}^{DC}$ and $VA_{SD}^{AC}$ may be determined by equation 1 and 2 as below:

$$VA_{SD}^{DC}(D_{path}) = \exp\left(-\frac{D_{path}}{\lambda_{SD}^{DC}}\right) \quad (1)$$

-continued $$VA_{SD}^{AC}(D_{path}) = \exp\left(-\frac{D_{path}}{\lambda_{SD}^{AC}}\right). \quad (2)$$

The $VA_{DS}^{SC}$ may be fitted with a modified Boltzmann equation with two parameters $\alpha_1$ and $\alpha_2$, wherein $\alpha_1$ approximately represents the distance at the $VA_{DS}^{DC}=0.5$ and $\alpha_2$ indicates the variation in the slope of the inverse-sigmoid curve of the $VA_{DS}^{DC}$ at $\alpha_1$.

The $VA_{DS}^{DC}$ may be determined by equation 3 as below:

$$VA_{DS}^{DC}(D_{path}) = \frac{1}{1 - \exp\left(\frac{-\alpha_1}{\alpha_2}\right) + \exp\left(\frac{D_{path} - \alpha_1}{\alpha_2}\right)}. \quad (3)$$

The system parameters may comprise the voltage attenuation factors, somatic input resistance of the neuron ($R_N$) and membrane time constant of the neuron ($\tau_m$).

The plurality of passive parameter may be determined at the specific $D_{path}$ from the soma by solving the inverse equations for the system parameters.

The passive parameters may comprise somatic membrane conductance and dendritic membrane conductance ($G_{m, S}$ and $G_{m, D}$), somatic membrane capacitance and dendritic membrane capacitance ($C_{m, S}$ and $C_{m, D}$), and one coupling conductance ($G_C$) between the soma and dendrite.

The determining a plurality of passive parameter may comprise determining the plurality of passive parameter by equation 4 to 8 as below:

$$G_{m,S} = \frac{1 - VA_{DS}^{DC}}{r_N(1 - VA_{SD}^{DC} VA_{DS}^{DC})} \quad (4)$$

$$G_{m,D} = \frac{pVA_{DS}^{DC}(1 - VA_{SD}^{DC})}{(1-p)r_N VA_{SD}^{DC}(1 - VA_{SD}^{DC} VA_{DS}^{DC})} \quad (5)$$

$$G_C = \frac{pVA_{DS}^{DC}}{r_N(1 - VA_{SD}^{DC} VA_{DS}^{DC})} \quad (6)$$

$$C_{m,D} = \frac{1}{\omega(1-p)} \sqrt{\frac{G_C^2}{(VA_{SD}^{AC})^2} - \{G_C + G_{m,D}(1-p)\}^2} \quad (7)$$

$$C_{m,S} = \frac{\tau_m\{p(1-p)\tau_m G_{m,S} G_{m,D} + pG_{m,S}(\tau_m G_C - C_{m,D}) + p^2 G_{m,S} C_{m,D} + (1-p)(\tau_m G_C G_{m,D} - G_C C_{m,D})\}}{p\{(1-p)(\tau_m G_{m,D} - C_{m,D}) + \tau_m G_C\}}, \quad (8)$$

wherein $r_N$ is the input resistance ($R_N$) normalized with the surface area of somatic compartment, ω is the maximum frequency component in an action potential, and p is the ratio of somatic to total surface area of the reduced model.

The method may further comprise determining two-compartmental neuron model consisting of a somatic compartment and a dendritic compartment that are coupled with the single conductance ($G_C$), wherein the somatic compartment has the $G_{m, S}$ and the $C_{m, S}$ as passive dynamics, and the dendritic compartment has the $G_{m, D}$ and the $C_{m, D}$ as passive dynamics.

According to the present invention, a relationship between asymmetry in signal propagation between a soma and dendrites and dendritic excitability is examined and neuron is modeled using the relationship.

According to the present invention, the relationship is represented through voltage attenuation factors, therefore neuron is modeled using the voltage attenuation factors.

This present invention could provide a theoretical basis for physiologically representing the excitability of the dendrite in the reduced neuron models on the physical domain (i.e. $D_{path}$), not on the electrical domain (i.e. length constant, λ) used up to date.

Thereby the identification of voltage attenuation factors governing spatial heterogeneity of dendritic excitability may bridge the gap between the anatomically reconstructed and reduced neuron models.

According to the present invention, technological advancements are achieved in a next generation information processing field such as bio-neural network simulation algorithms, a rehabilitation field such as a neural-machine interface technique to recover ataxia and an advanced complement, a medical equipment development field such as bio-neural network diagnosis by measuring nerve signaling from bio-neural system, and new medicine examination field.

BRIEF DESCRIPTION OF THE DRAWINGS

The above and other objects, features and advantages of the present invention will be more clearly understood from the following detailed description taken in conjunction with the accompanying drawings, in which:

FIGS. 4A, 4B, 4C, 4D, 4E and 4F show sensitivity of cellular excitability to the VA factors;

DESCRIPTION OF THE PREFERRED EMBODIMENTS

Figure 1A:
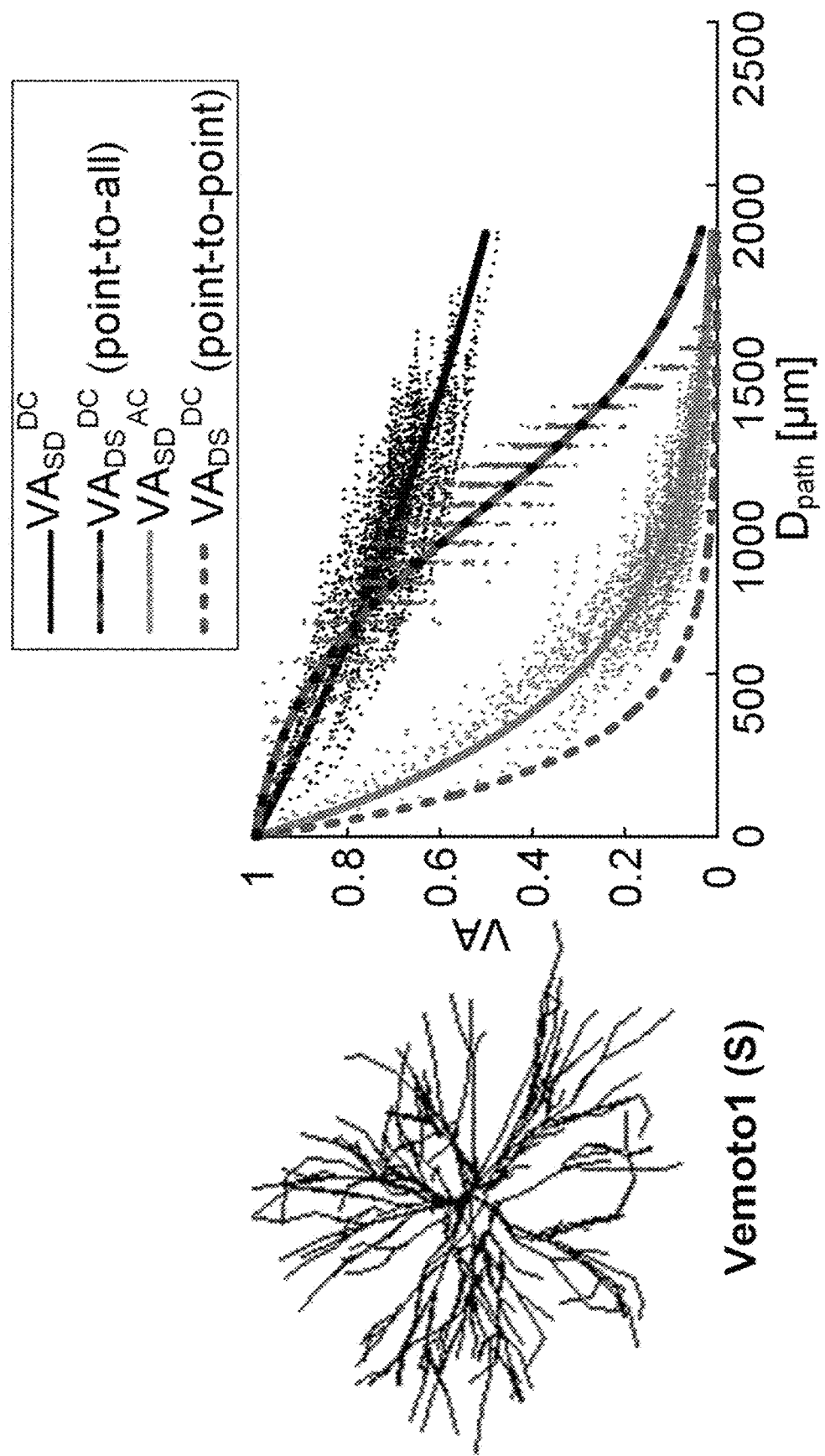
FIGS. 1A, 1B, 1C, 1D, 1E, and 1F show characterization of voltage attenuation property of the dendrites.
Figure 1B:
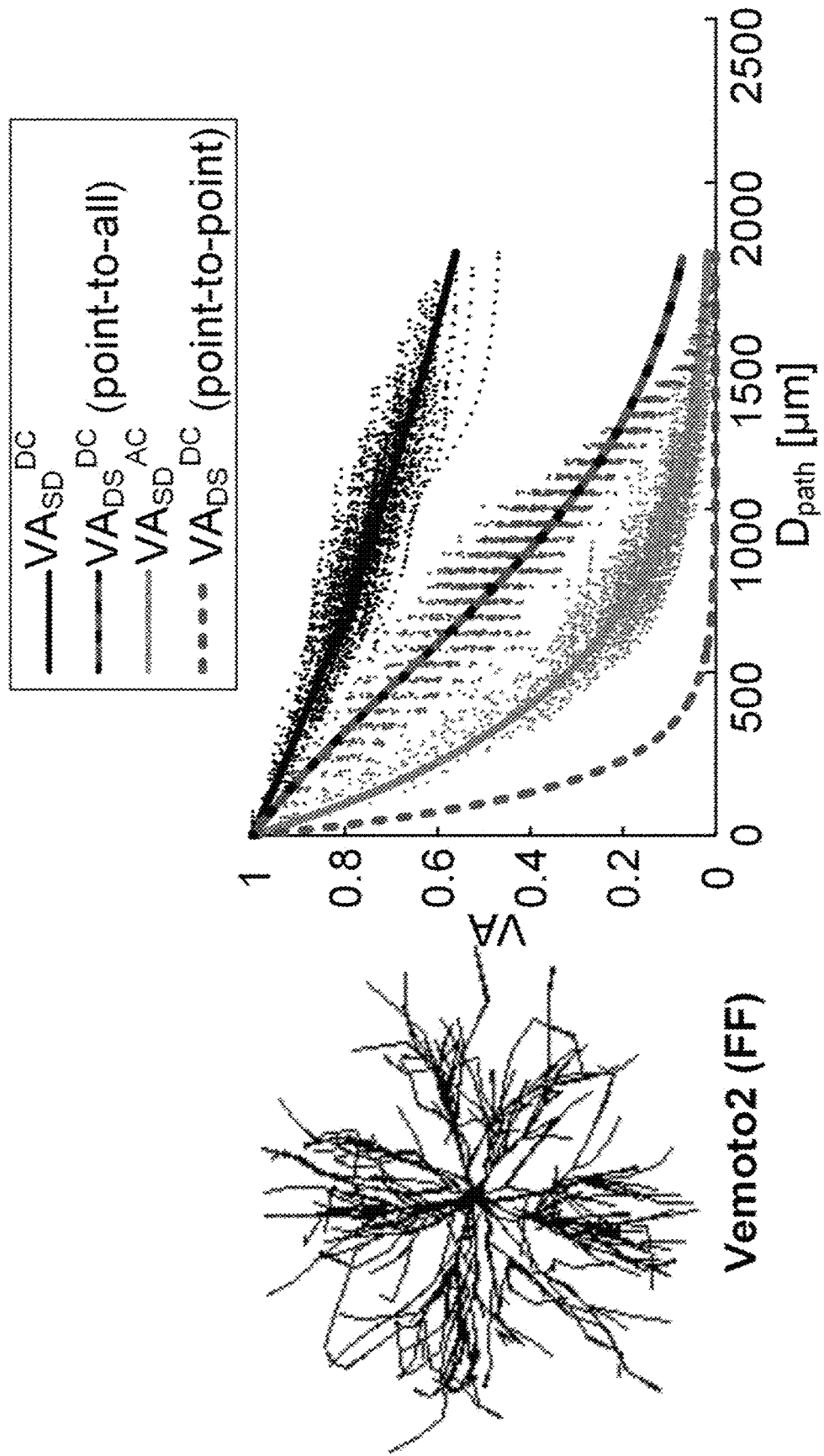
Figure 1C:
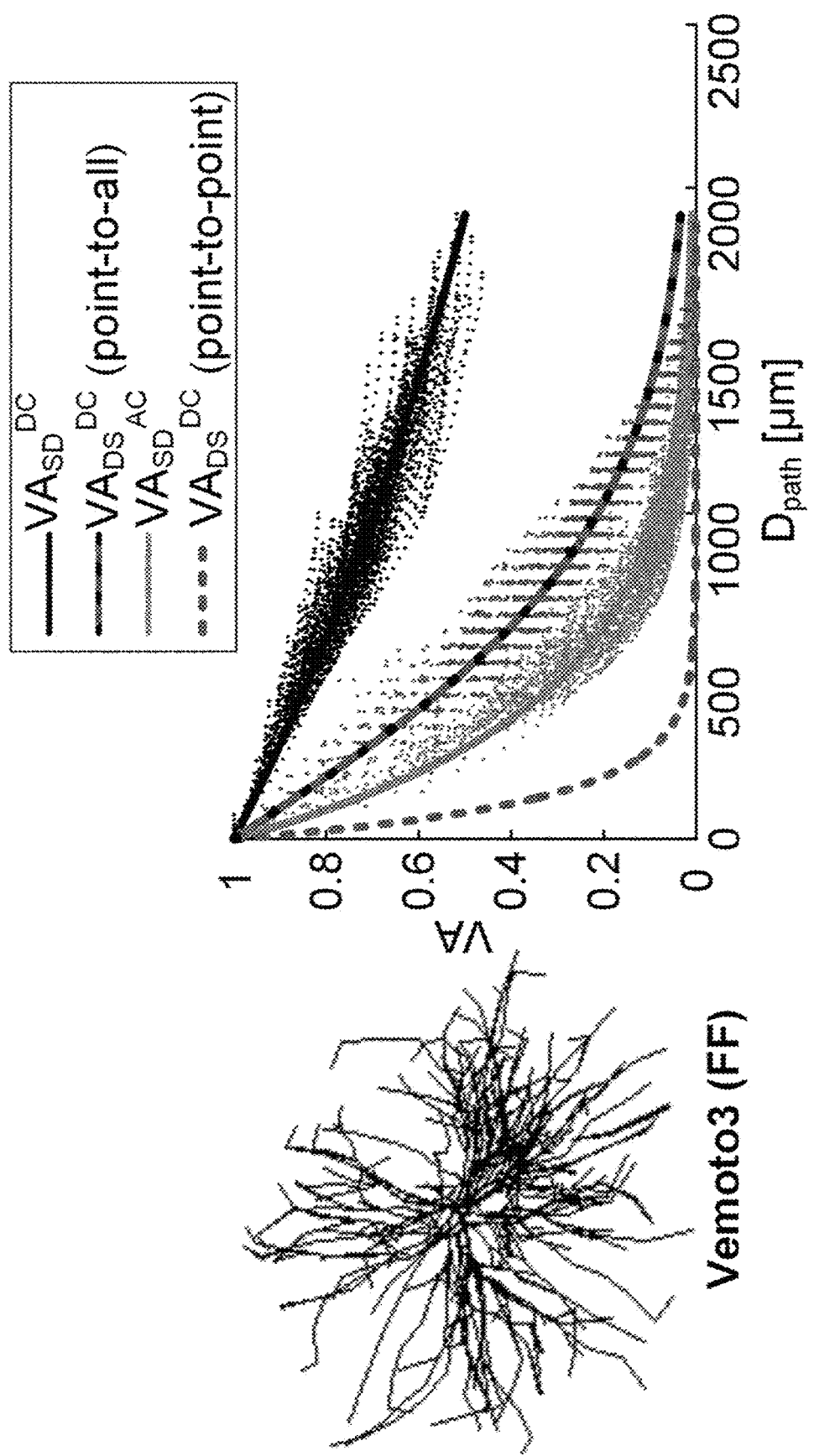
Figure 1D:
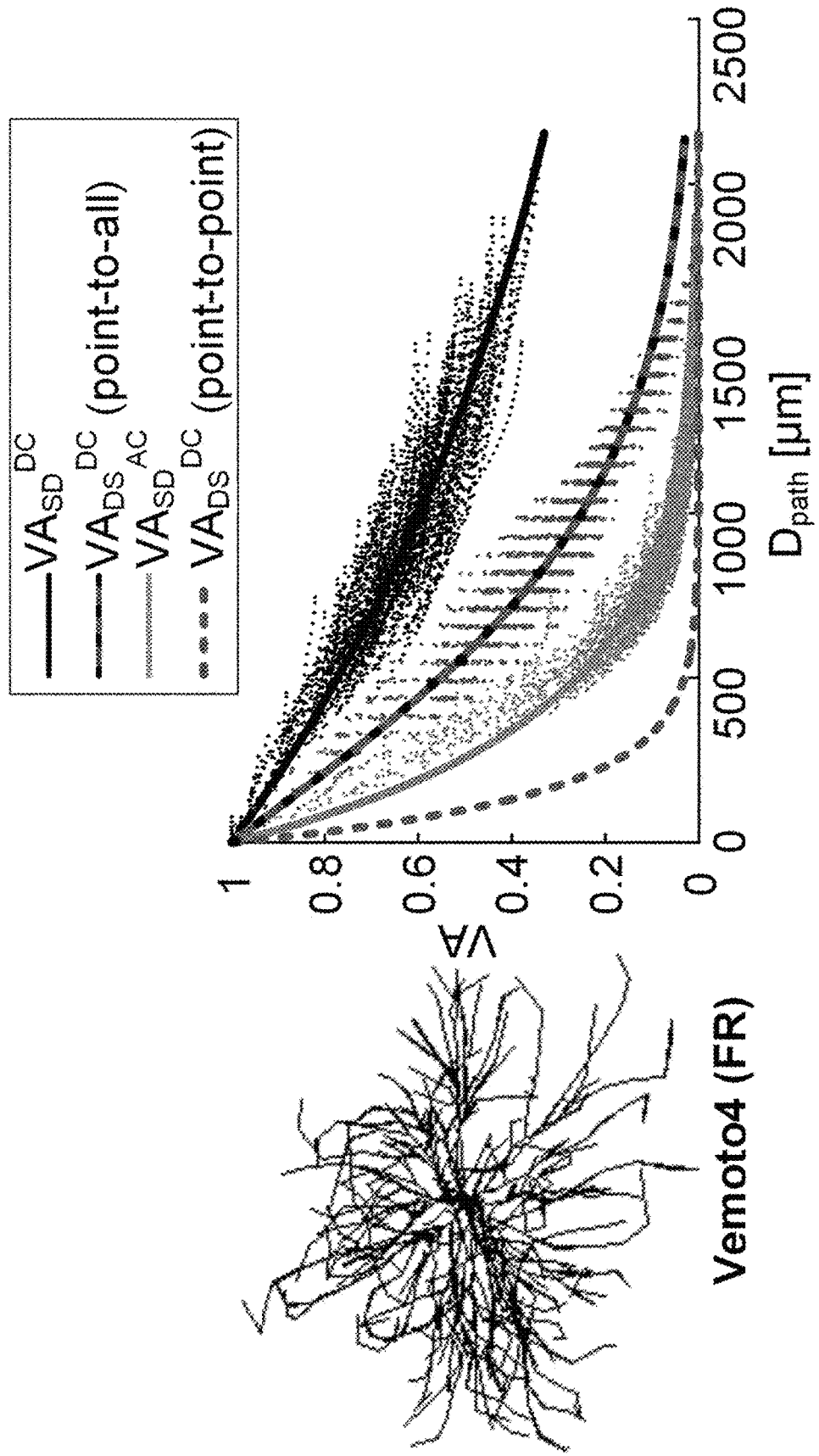

The inventors of the present invention first compare the dependency of dendritic signaling on the direction and frequency among different types of primary neurons across the central nervous system.

Based on the consistent characteristics of this asymmetry across neuron types, the inventors of the present invention then chose one of these types, the spinal motoneuron, to provide the basis for development of a reduced modeling approach that allows us to systematically examine the influence of the direction and frequency dependent dendritic signaling, to identify the relationship between asymmetric signal propagation and dendritic excitability.

Specifically the inventors of the present invention elucidate whether the complex signaling properties of the dendrites are essential to physiologically represent dendritic excitability and how changes in these signaling properties affect normal patterns of activation of voltage sensitive channels in the dendritic tree.

Based on the analysis of asymmetry in several types of neurons, the inventors of the present invention developed a new methodology for reducing a fully reconstructed motoneuron model to a two-compartment representation that preserved asymmetric signal propagation.

The reduced models of the present invention use dendritic excitability and asymmetry of signal propagation. In the present invention, asymmetry of signal propagation is presented by persistent inward current (PIC) dispersed over the dendrites, thus the reduced models of the present invention accurately replicated the dendritic excitability and the dynamics of the anatomical model involving a persistent inward current (PIC) dispersed over the dendrites.

The reduced models of the present invention were used to understand the relationship between asymmetric signal propagation and dendritic excitability. The inventors of the present invention found that increases in signal attenuation from soma to dendrites increased the activation threshold of a PIC (hypo-excitability), whereas increases in signal attenuation from dendrites to soma decreased the activation threshold of a PIC (hyper-excitability).

These effects were so strong that reversing the asymmetry in the soma-to-dendrite vs. dendrite-to-soma attenuation reversed the correlation between PIC threshold and distance of this current source from the soma. It is important to maintain the normal asymmetry in dendritic signaling not only for normal physiological function of the cells but also for biophysically realistic simulations of dendritic excitability.

Hereinafter, embodiments of the present invention will be described in detail with reference to the attached drawings. Those skilled in the art will appreciate that various modifications are possible, and the present invention is not limited to the following embodiment. Furthermore, the embodiment of the present invention aims to help those with ordinary knowledge in this art more clearly understand the present invention. The terms and words used for elements in the description of the present invention have been determined in consideration of the functions of the elements in the present invention. The terms and words may be changed depending on the intention or custom of users or operators, so that they should not be construed as limiting elements of the present invention.

Method

Preparation of Neuron Anatomy

The morphological data of six cat spinal α-motoneurons (Vemoto1-6 in Burke's archive), one rat hippocampal CA3 pyramidal cell (2189201 in Claiborne's archive), one rat neocortical L5 pyramidal cell (p21 in Dendritica's archive), and one rat cerebellum Purkinje cell (p19 in Dendritica's archive) was downloaded from http://NeuroMorpho.Org [Ascoli GA (2006) Mobilizing the base of neuroscience data: the case of neuronal morphologies. Nat Rev Neurosci 7: 318-324] and translated into the NEURON simulation environment v 6.1.1 [Hines M L, Carnevale N T (1997) The NEURON simulation environment. Neural Comput 9: 1179-1209] using Import3D tool. For individual imported motoneurons, the initial segment/axonal hillock was added to the soma after correcting the size of the cell body to the dimension previously reported [Kim H, Major L A, Jones K E (2009) Derivation of cable parameters for a reduced model that retains asymmetric voltage attenuation of reconstructed spinal motor neuron dendrites. J Comput Neurosci 27: 321-336, Cullheim S, Fleshman J W, Glenn L L, Burke R E (1987) Membrane area and dendritic structure in type-identified triceps surae alpha motoneurons. J Comp Neurol 255: 68-81].

Assignment of Passive Membrane Properties

The values for the specific membrane resistivity ($R_m$) of the motoneurons and resulting electrotonic properties were fully addressed in our previous study [Kim H, Major L A, Jones K E (2009) Derivation of cable parameters for a reduced model that retains asymmetric voltage attenuation of reconstructed spinal motor neuron dendrites. J Comput Neurosci 27: 321-336], assuming uniform cytoplasmic resistivity ($R_a$=70 Ω·cm) and specific membrane capacitance ($C_m$=1 μF/cm$^2$) [20]. The same $R_m$ (225 Ω·cm$^2$ at the soma and 11 KΩ·cm$^2$ at the dendrites), $R_a$ and $C_m$ of the motoneuron (i.e. Vemoto6) were used for three anatomically reconstructed neurons in the brain: hippocampal pyramidal, neocortical pyramidal and cerebellar Purkinje cell.

Generation of Voltage Attenuation Curve and Voltage Decay Constant

The voltage attenuation (VA) factor representing signal propagation of the dendrites was defined as a ratio of voltage at the measurement site to voltage at the current injection site in the passive membrane condition [Rall W, Rinzel J (1973) Branch input resistance and steady attenuation for input to one branch of a dendritic neuron model. Biophys J 13: 648-687, Carnevale N T, Johnston D (1982) Electrophysiological characterization of remote chemical synapses. J Neurophysiol 47: 606-621]. Both direct (DC) and alternating current (AC) were taken into account for physiological current components flowing between the soma and the dendrites: DC for steady current stimulation at the soma, tonic synaptic inputs, persistent currents at the dendrites, and AC for action potentials at the soma. Three VA factors, two for the somatofugal direction with somatically injected DC ($VA_{SD}^{DC}$) and 250 Hz-AC ($VA_{SD}^{AC}$) input and one ($VA_{DS}^{DC}$) for the somatocentric direction with simultaneous DC inputs to all points in the dendrites at the same distance from the soma, were calculated in the passive dendrites of the anatomically reconstructed neurons using the Impedance class tools in NEURON software [Hines M L, Carnevale N T (1997) The NEURON simulation environment. Neural Comput 9: 1179-1209].

The $VA_{DS}^{DC}$ was measured specifically for the propagation of steady synaptic inputs and persistent inward current generated by VGICs that are distributed over all branches of the dendrites at the same distance from the soma. The amount of current injection for the $VA_{DS}^{DC}$ was differentially supplied to individual points in the dendrites in proportion to the surface area of dendritic segment where each point was involved. The AC frequency of 250 Hz was calculated from the average spike width of 2 ms (or period=4 ms) for motoneurons [Coombs J S, Eccles J C, Fatt P (1955) The electrical properties of the motoneurone membrane. J Physiol 130: 291-325]. The $VA_{SD}^{AC}$ for the AC signals with lower frequencies (<250 Hz) has been shown to be well conserved in our reduced modeling framework [Kim H, Jones K E (2012) The retrograde frequency response of passive dendritic trees constrains the nonlinear firing behaviour of a reduced neuron model. PLoS One 7: e43654.]. The individual VA data was plotted as a function of path length (i.e. $D_{path}$) from the soma.

To quantify the rate of attenuation with the distance, the $VA_{SD}^{DC}$ and $VA_{SD}^{AC}$ were fitted by single exponential function with voltage decay constant ($\lambda_{SD}^{DC}$ and $\lambda_{SD}^{AC}$) whereas the $VA_{DS}^{DC}$ was fitted with a modified Boltzmann equation with two parameters ($\alpha_1$ and $\alpha_2$) where $\alpha_1$ approximately represents the distance at the $VA_{DS}^{DC}$=0.5 and $\alpha_2$ indicates the variation in the slope of the inverse-sigmoid curve of the $VA_{DS}^{DC}$ at $\alpha_1$ (see FIGS. 1A, 1B, 1C, 1D, 1E, and 1F for detailed shape). The parameter values of individual fitting equations were determined using the nonlinear regression function (i.e. nlinfit) in MATLAB.

$$VA_{SD}^{DC}(D_{path}) = \exp\left(-\frac{D_{path}}{\lambda_{SD}^{DC}}\right) \quad (1)$$

$$VA_{SD}^{AC}(D_{path}) = \exp\left(-\frac{D_{path}}{\lambda_{SD}^{AC}}\right) \quad (2)$$

$$VA_{DS}^{DC}(D_{path}) = \frac{1}{1 - \exp\left(\frac{-\alpha_1}{\alpha_2}\right) + \exp\left(\frac{D_{path} - \alpha_1}{\alpha_2}\right)} \quad (3)$$

The four voltage decay constants ($\lambda_{SD}^{DC}$, $\lambda_{SD}^{AC}$ and $\alpha_1$ & $\alpha_2$ in equation (1)-(3)) specified for Vemoto6 were used to determine the values of three VA factors for the reduced models.

The default values of the VA factors for the reduced model of the present invention were specified at the $D_{path}$ 106 of 600 μm, which is an average of the distance interval (300-850 μm) previously reported for the distribution of PIC channels to produce experimentally observed nonlinear firing patterns in the anatomical model [Elbasiouny S M, Bennett D J, Mushahwar V K (2005) Simulation of dendritic CaV1.3 channels in cat lumbar motoneurons: spatial distribution. J Neurophysiol 94: 3961-3974, Bui T V, Ter-Mikaelian M, Bedrossian D, Rose P K (2006) Computational estimation of the distribution of L-type Ca(2+) channels in motoneurons based on variable threshold of activation of persistent inward currents. J Neurophysiol 95: 225-241].

Reduced Neuron Model

A conductance-based, two-compartmental neuron model is used consisting of a somatic compartment and a dendritic compartment that are coupled with a single conductance. The passive dynamics of the reduced neuron model is determined by the five passive parameters: two conductances ($G_{m,S}$ and $G_{m,D}$) for the soma and dendrite, two capacitances ($C_{m,S}$ and $C_{m,D}$) for the soma and dendrite, and one coupling conductance ($G_C$) between the soma and dendrite. The unique feature of our reduce modeling approach is that all five passive parameters of the reduced model are analytically determined from the five system parameters (somatic input resistance ($R_N$), membrane time constant ($\tau_m$) $VA_{SD}^{DC}$ ($D_{path}$) $VA_{SD}^{AC}$ ($D_{path}$) and $VA_{DS}^{DC}$ ($D_{path}$)) empirically measurable from real cells. The five passive parameters of the reduced model were uniquely determined for the VA factors specified at the distance from the soma by solving the inverse equations, $$G_{m,S} = \frac{1 - VA_{DS}^{DC}}{r_N(1 - VA_{SD}^{DC}VA_{DS}^{DC})} \quad (4)$$

$$G_{m,D} = \frac{pVA_{DS}^{DC}(1 - VA_{SD}^{DC})}{(1-p)r_N VA_{SD}^{DC}(1 - VA_{SD}^{DC}VA_{DS}^{DC})} \quad (5)$$

$$G_C = \frac{pVA_{DS}^{DC}}{r_N(1 - VA_{SD}^{DC}VA_{DS}^{DC})} \quad (6)$$

$$C_{m,D} = \frac{1}{\omega(1-p)}\sqrt{\frac{G_C^2}{(VA_{SD}^{AC})^2} - \{G_C + G_{m,D}(1-p)\}^2} \quad (7)$$

$$C_{m,S} = \frac{\tau_m\{p(1-p)\tau_m G_{m,S}G_{m,D} + pG_{m,S}(\tau_m G_C - C_{m,D}) + p^2 G_{m,S}C_{m,D} + (1-p)(\tau_m G_C G_{m,D} - G_C C_{m,D})\}}{p\{(1-p)(\tau_m G_{m,D} - C_{m,D}) + \tau_m G_C\}} \quad (8)$$

where $r_N$ is the input resistance ($R_N$) normalized with the surface area of the somatic compartment; ω is the maximum frequency component in an action potential; p is the ratio of somatic to total surface area of the reduced model.

In the present invention, the somatic surface area (315759.2 µm2) of the reduced model represents total accumulated surface area from the soma up to $D_{path}$=600 µm in the anatomically reconstructed motoneuron (i.e. Vemoto6). The $r_N$ and p were calculated from the $R_N$ (1.29 MΩ) and total surface area (641786.9 µm2) of the Vemoto6. The default values of $r_N$ (0.407 Ω·m2), $\tau_m$ (7.2 ms), p (0.492), and ω (2π×250 Hz calculated from the period of 4 ms assuming the spike width of 2 ms) were set to be constant at all distances (i.e. $D_{path}$). The system equations and derivations of forward/inverse equations for the reduced model have been fully addressed in the present invention.

Assignment of Active Membrane Properties

A fast twitch and fatigue resistant (FR)-type motoneuron (Vemoto6) of six anatomical models was chosen for the comparison with the reduced model since its input-output properties associated with the distribution of Ca PIC channels in its dendrites were fully analyzed in the previous study [Elbasiouny S M, Bennett D J, Mushahwar V K (2005) Simulation of dendritic CaV1.3 channels in cat lumbar motoneurons: spatial distribution. J Neurophysiol 94: 3961-3974]. The same types and kinetics of voltage gated ion channels and excitatory synapse were used for both the anatomical and reduced motoneuron model (see [Fleshman J W, Segev I, Burke R B (1988) Electrotonic architecture of type-identified alpha-motoneurons in the cat spinal cord. J Neurophysiol 60: 60-85] for details of equations). Briefly, action potentials were generated by various active currents: $I_{Na,f}$, $I_{Na,p}$, $I_{K, Dr}$, $I_{Ca,N}$, $I_{K(Ca)}$ at the soma and $I_{Na,f}$, $I_{Na,p}$, $I_{K, Dr}$ at the initial segment/axonal hillock in the anatomical model, and $I_{Na,f}$, $I_{Na,p}$, $I_{K, Dr}$, $I_{Ca,N}$, $I_{K(Ca)}$ at the somatic compartment of the reduced model. Plateau potentials were produced by currents ($I_{Ca,L}$) mediated by L-type $Ca^{2+}$ channels in the dendrites of both models. In the absence of the $I_{Ca,L}$, the active channel densities ($G_{Na,f}$ [mS/cm$^2$], $G_{Na,p}$ [mS/cm$^2$], $G_{K, Dr}$ [mS/cm$^2$], $G_{Ca,N}$ [mS/cm$^2$] and $G_{K(Ca)}$ [mS/cm$^2$]) responsible for spike generation were adjusted to have the same height (i.e. 92.3 mV) of an action potential and afterhyperpolarization (AHP) properties (i.e. duration of 98.5 ms and depth of 3.1 mV) at the same rheobase current (i.e. 10.5 nA) in both reduced and anatomical model. $G_{Ca,L}$ [mS/cm$^2$] for $I_{Ca,L}$ in the dendrite of the reduced model was determined to fit the peak current (i.e. −22 nA) measured in the anatomical model during triangular voltage clamp simulations bile blocking all active currents at the soma [Lee R H, Heckman C J (1999) Paradoxical effect of QX-314 on persistent inward currents and bistable behavior in spinal motoneurons in vivo. J Neurophysiol 82: 2518-2527].

Stimulation Protocols

The somatic input-somatic output relation was evaluated by applying slowly ascending and descending voltage (duration of 20 sec with peak of 30 mV starting from −70 mV) and current (duration of 10 sec with peak of 20 nA starting from 0) clamp to the soma. The dendritic input-somatic output relation was investigated while slowly increasing and decreasing maximum conductance (i.e. $G_{syn}$) of excitatory synaptic receptors in the dendrites in a triangular form (duration of 20 sec with peak of 1.2 mS/cm$^2$ for the anatomical and 0.12 mS/cm$^2$ for the reduced case starting from 0). The peak of the $G_{syn}$ in the reduced case was adjusted to match the same onset timing (5 ms) and peak value (−13.6 mV) of the plateau potential as the anatomical case. The smaller $G_{syn}$ in the reduced case resulted from the larger surface area of the dendrite for Ca PIC channels compared to the anatomical case.

Result

Three Voltage Attenuation Parameters to Characterize Dendritic Signaling in Neurons Signal propagation of the dendrites was characterized in fully reconstructed neuron models by three voltage attenuation (VA) factors: two for the soma-to-dendrite direction with DC ($VA_{SD}^{DC}$) and AC($VA_{SD}^{AC}$) input to the soma, and one ($VA_{DS}^{DC}$) for the dendrite-to-soma direction with simultaneous DC inputs to all points in the dendrites at the same distance from the soma.

The three VA factors define neuron voltage profiles in response to steady current injected at the soma ($VA_{SD}^{DC}$), action potentials propagating from the initial segment and soma into the dendrites ($VA_{SD}^{AC}$), and steady synaptic inputs and plateau potential generated by VGICs in the dendrites ($VA_{DS}^{DC}$).

FIGS. 1A, 1B, 1C, 1D, 1E, and 1F show characterization of voltage attenuation property of the dendrites. In FIG. 1A-1E, morphologies of the motoneurons in the left column and the three voltage attenuation (VA) factors measured at all distances ($D_{path}$) from the soma ($VA_{SD}^{DC}$ in black, $VA_{SD}^{AC}$ in gray and $VA_{DS}^{DC}$ in purple) in the right column. A single exponential function ($\exp(-D_{path}/\lambda)$) was used to fit the $VA_{SD}^{DC}$ (λ=2678.7, 3085.6, 2763.7, 1945.5 and 2156.4 for A-E) and $VA_{SD}^{AC}$ (λ=420.1, 437.1, 402.3, 373.1 and 464.7 for A-E), and a modified Boltzmann equation $(1/[1-\exp(-\alpha_1/\alpha_2)+\exp((D_{path}-\alpha_1)/\alpha_2)])$ for $VA_{DS}^{DC}$ ($\alpha_1$ & $\alpha_2$=1020.8&307.7, 635.2&439.5, 327.9&469.6, 374.2&504.8 and 861.9&268.3 for A-E).

Note that purple solid lines represents the $VA_{DS}^{DC}$ between the soma and all points in the dendrites at the same distance (i.e. point-to-all) whereas purple dotted lines (exp$(-D_{path}/\lambda)$ where λ=225, 143.6, 118.5, 144, 193.7 for A-E) for the $VA_{DS}^{DC}$ between the soma and a single point along the path of all individual dendritic trees from the soma (i.e. point-to-point).

Figure 1E:
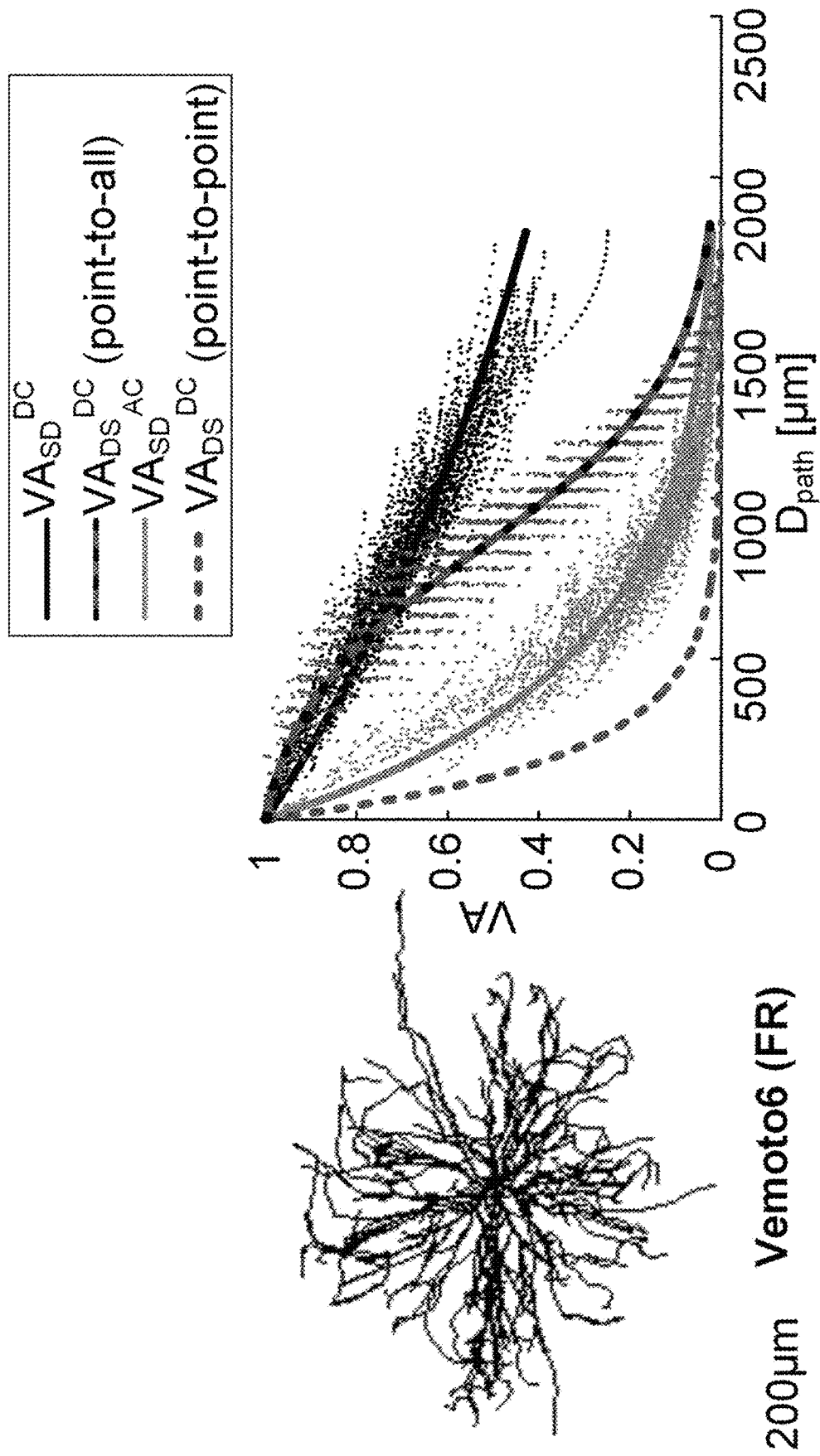
Figure 1F:
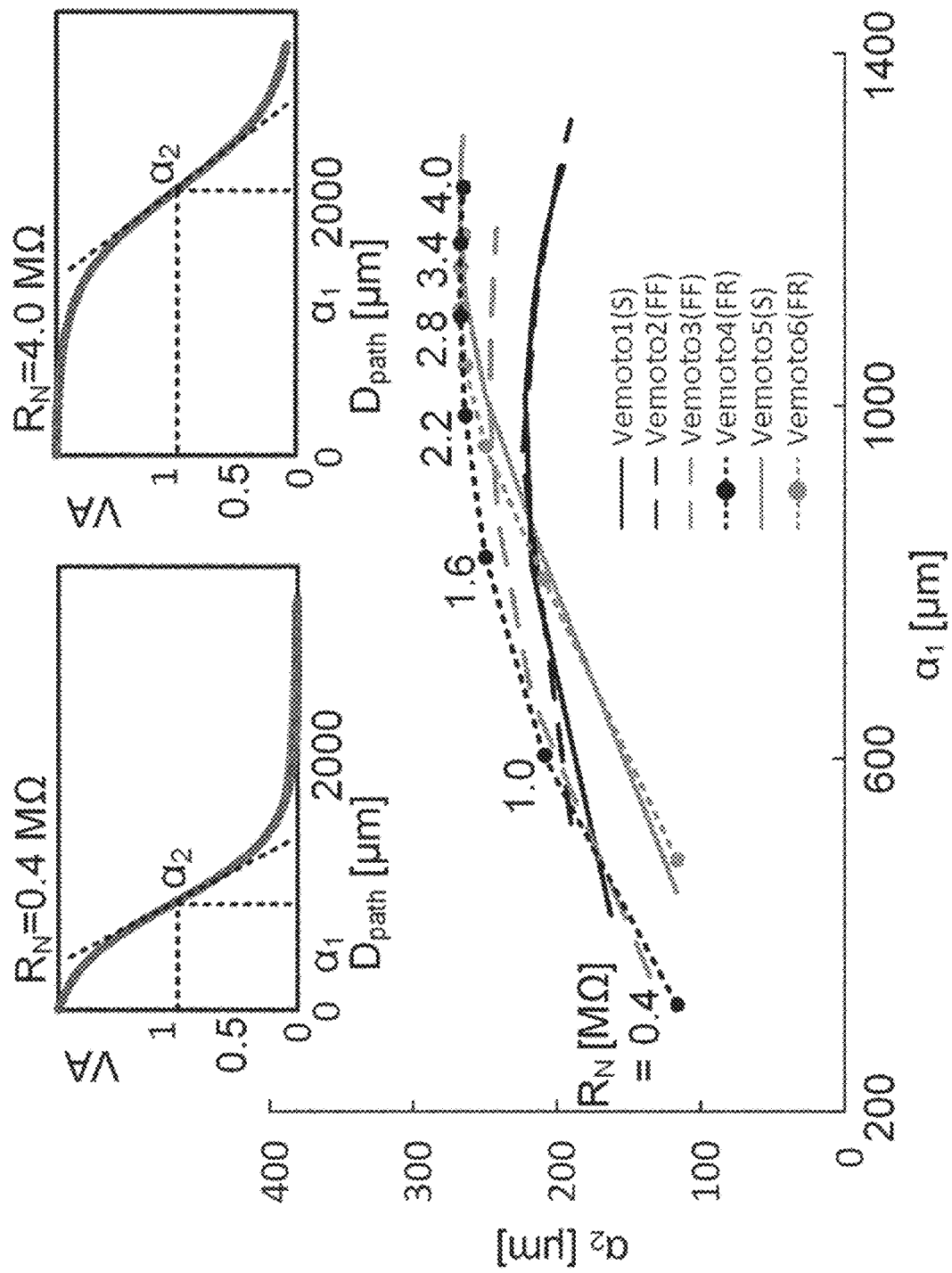

In FIG. 1F, the $VA_{DS}^{DC}$ was measured in six type identified anatomically reconstructed motoneurons while varying the input resistance ($R_N$) from 0.4 to 4.0 MΩ. The $\alpha_1$ (the distance at which the $VA_{DS}^{DC}$ dropped to 50%) parameter was more sensitive to changes in $R_N$ compared with $\alpha_2$ parameter (a measure of the slope of the curve at $\alpha_1$). The insets show examples of the $VA_{DS}^{DC}$ curves at extreme $R_N$ values of 0.4 and 4.0 MΩ. Note that the distribution of points ($\alpha_1$, $\alpha_2$) at the same $R_N$ is not type specific (e.g. gray and black filled circles for FR-type motoneurons). S, FR and FF indicate slow twitch, fast twitch and fatigue resistant, and fast twitch and fast fatigable motoneuron type respectively.

FIGS. 1A-1E show voltage attenuation as a function of distance from the soma ($D_{path}$) in the five (i.e. Vemoto1-4 and 6) type-identified anatomically reconstructed spinal MNs. Each point in this figure shows the voltage attenuation at a single point in a dendritic branch at the indicated path distance. In all five anatomical MN models, the spatial profile of the individual VA factors was distinguishably different indicating the direction and frequency dependency of the dendritic signaling. The different dependencies of individual VA factors on the distance stem from the unbalance in electrical load between the soma and dendrites due to the highly branching structure of the dendrites and the low-pass filtering effect due to the cable properties. The vertical alignment of the data for the $VA_{DS}^{DC}$ results from spatial sampling at a resolution of 50 µm. The $VA_{DS}^{DC}$ data were fit to an inverse sigmoid curve (solid purple lines in FIGS. 1A and 1E), rather than the single-exponential curve (dashed purple line) previously fit to $VA_{DS}^{DC}$ when this parameter was computed between the soma and a single point in the dendrites [Kim H, Major L A, Jones K E (2009) Derivation of cable parameters for a reduced model that retains asymmetric voltage attenuation of reconstructed spinal motor neuron dendrites. J Comput Neurosci 27: 321-336]. The difference in DC voltage attenuation from the dendrites to the soma when calculated with the new approach was obvious in all five anatomical MN models and resulted from the summation of multiple inputs at the soma originating from the separate dendritic branches.

The data from the other two voltage 214 attenuation parameters were well fit by single exponential curves. The equations fitting individual VA data were used to calculate the values of three VA factors for the reduced MN models. The spatial profile of the two VA factors from the soma to the dendrites was consistent across different types (slow twitch (S), fast twitch and fatigue-resistible (FR), fast twitch and fatigable (FF)) of MN models whereas the VA factor from the dendrites to the soma appeared to be related to the MN types. The S- or FR-type MN model with high input resistance (e.g. Vemoto1 (1.9 MΩ) or Vemoto6 (1.25 MΩ)) tended to be much more slowly attenuated with the distance showing the inverse sigmoid profile compared to the FF- or FR-type MN models with low input resistance (e.g. Vemoto2-3 (0.7-0.8 MΩ) or Vemoto4 (0.97 MΩ)).

Thus, the inventor of the present invention further analyzed six type-identified anatomically reconstructed MNs to evaluate how $VA_{DS}^{DC}$ generalized to a population of MNs with widely varying morphological and electrical characteristics (FIG. 1F). The inventor of the present invention changed the specific membrane resistivity so that all anatomical models had the same input resistance ($R_N$) at the soma, and recalculated and fit the $VA_{DS}^{DC}$ data to the inverse sigmoid curve to find the coefficients $\alpha_1$ and $\alpha_2$. The $\alpha_1$ parameter was more sensitive to changes in $R_N$ compared with $\alpha_2$ parameter.

All six MN morphologies had similar relationships between $R_N$ and changes in $\alpha_1$ & $\alpha_2$ suggesting that the differences in morphology of the 6 models did not play a major role in $VA_{DS}^{DC}$ behavior. The evaluation of $VA_{SD}^{DC}$ and $VA_{SD}^{AC}$ for a population of MNs was presented in our previous studies [Kim H, Jones K E (2012) The retrograde frequency response of passive dendritic trees constrains the nonlinear firing behaviour of a reduced neuron model. PLoS One 7: e43654, Kim H, Major L A, Jones K E (2009) Derivation of cable parameters for a reduced model that retains asymmetric voltage attenuation of reconstructed spinal motor neuron dendrites. J Comput Neurosci 27: 321-336].

All these results suggest that the voltage attenuation properties in the motoneurons might not be specific to the type-related morphology of motoneurons, but a generic property of the branched architecture of dendritic trees.

Reduced Motoneuron Model Incorporating VA Factors for Dendritic Excitability

Spinal MNs were chosen for our evaluation of the relationship between the signal attenuation properties and dendritic excitability because they have large, highly branching dendrites and VGICs that generate strong persistent inward currents (PICs) [26]. The influence of PICs on MN firing patterns is profound and has been thoroughly investigated in various species including turtle [Hounsgaard J, Kiehn O (1989) Serotonin-induced bistability of turtle motoneurones caused by a nifedipine-sensitive calcium plateau potential. J Physiol 414: 265-282], rat [Li Y, Bennett D J (2003) Persistent sodium and calcium currents cause plateau potentials in motoneurons of chronic spinal rats. J Neurophysiol 90: 857-869], mouse [Meehan C F, Sukiasyan N, Zhang M, Nielsen J B, Hultborn H (2010) Intrinsic properties of mouse lumbar motoneurons revealed by intracellular recording in vivo. J Neurophysiol 103: 2599-2610] and cat [Lee R H, Heckman C J (1998)Bistability in spinal motoneurons in vivo: systematic variations in 614 persistent inward currents. J Neurophysiol 80: 583-593].

Figure 2A:
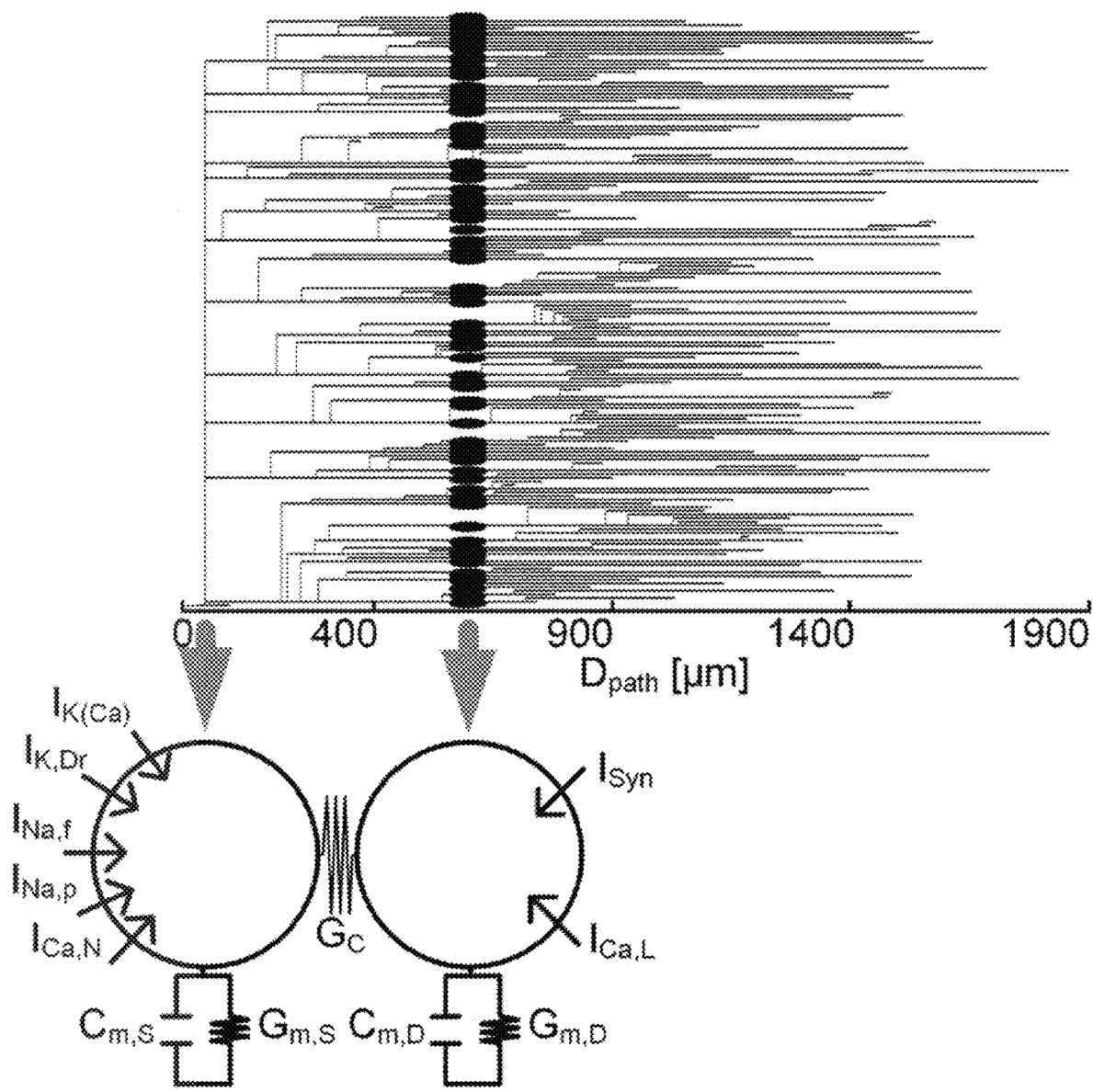
FIGS. 2A, 2B, 2C, 2D, 2E, 2F, 2G, 2H, and 2I show comparison of the anatomical (blue) and reduced (red) MN model.

FIGS. 2A, 2B, 2C, 2D, 2E, 2F, 2G, 2H, and 2I show comparison of the anatomical (blue) and reduced (red) MN model. FIG. 2A shows reduction of anatomical dendrites. A dendrogram (upper panel) of a MN (i.e. vemoto6 in Methods) with path length ($D_{path}$) from the soma and two compartments (bottom panel) of the reduced model representing the soma/initial segment/axonal hillock (indicated by left arrow) and all points in the narrow band (e.g. mean of 600 μm and standard deviation of 4 μm, right arrow) of dendrites of its original cell. Note that membrane potentials at individual points in the dendrites of the anatomical model were averaged for the purpose of comparison to the reduced model. FIGS. 2B-2E show passive dynamics. All five passive parameters ($G_{m,\ S}$=0.143 mS/cm$^2$, $G_{m,\ D}$=0.131 mS/cm$^2$, $C_{m,\ S}$=1.058 mS/cm$^2$, $C_{m,\ D}$=0.915 mS/cm$^2$, $G_C$=0.211 mS/cm$^2$) of the reduced model were analytically determined to retain the five system properties measured from the anatomical model: input resistance ($R_N$=1.29 MΩ) and membrane time constant ($\tau_m$=7.2 ms) obtained by peeling analysis at the soma, and three voltage attenuation factors ($VA_{SD}^{DC}$=0.76, $VA_{DS}^{DC}$=0.75, $VA_{SD}^{AC}$=0.27) at $D_{path}$=600 μm. (B). Time course of membrane potential (Vm) in response to the step current ($I_{soma}$) injected to the soma for calculating $R_N$. (C). The semilog plot (solid lines) of transient voltage response at the soma to brief current pulse with smaller amplitude for anatomical than reduced case for $\tau_m$ and τ1 (equalizing time constant) equivalent to the inverse of slope of linear regression (dotted) line fitting the tail of each curve. (D). Time courses of Vm for $VA_{SD}^{DC}$ from the soma (solid lines) to dendrites (dotted lines) and $VA_{DS}^{DC}$ in the opposite direction, in response to DC input (bottom panel) to the soma (solid line) and dendrites (dotted line). (E). Time course of Vm normalized with its amplitude for $VA_{SD}^{AC}$ from the soma (solid line) to dendrites (dotted line), in response to somatically injected AC current ($I_{soma}$) with the frequency of 250 Hz. (F), (G). PIC activation with the addition of $I_{Ca,L}$ to the dendrites of both models. (F). Time course of effective PIC($I_{PIC}$, upper panel) obtained by subtracting leak ($I_{Leak}$) from total current ($I_{Total}$) injected for following the triangular voltage-clamp (Vm, middle panel) at the soma, and $I_{Total}$-Vm relationship (bottom panel). (G). Time course of Vm (upper panel) at the soma (solid lines) and dendrites (dotted lines) in response to triangular current clamp at the soma ($I_{soma}$, middle panel), and Vm-$I_{soma}$ relationship (bottom panel). Arrows indicate the ascending and descending phase of triangular voltage and current clamp. Maximum conductance ($G_{Ca,L}$) for $I_{Ca,L}$ was 1.37 mS/cm$^2$ for the anatomical and 0.124 mS/cm$^2$ for the reduced case. (H), (I). Cellular excitability with the addition of $I_{Na,f}$, Na,p, $I_{K,\ Dr}$, $I_{Ca,N}$ and $I_{K(Ca)}$ to the soma of both models. (H). Instantaneous firing rates (F, upper panel), time course of Vm (blue & red for the soma, and gray for the dendrite) in response to triangular current stimulation ($I_{soma}$) to the soma, and F-$I_{some}$ curve (bottom panel). Maximum conductances for the active currents in the anatomical case were $G_{Na,f}$=0.71 [S/cm$^2$], $G_{K,\ Dr}$=0.23 [S/cm$^2$], $G_{Ca,N}$=0.01 [S/cm$^2$], $G_{K(Ca)}$=0.0258 [S/cm$^2$] at the soma, $G_{Na,f}$=2.7 [S/cm$^2$], $G_{Na,p}$=0.033*10-3 [S/cm$^2$], $G_{K,\ Dr}$=0.17 [S/cm$^2$]at the initial segment and axon hillock, and $G_{Ca,L}$=1.37 [mS/cm$^2$] in the dendrites. For the reduced model, $G_{Na,f}$=26.75 [mS/cm$^2$], $G_{Na,p}$=0.00086 [mS/cm$^2$], $G_{K,\ Dr}$=6.2 [mS/cm$^2$], $G_{Ca,N}$=0.008 [mS/cm$^2$], $G_{K(Ca)}$=0.54 [mS/cm$^2$] at the soma and $G_{Ca,L}$=0.124 [mS/cm$^2$] at the dendrite. (I). F, Vm (blue & red for the soma, and gray for the dendrite) in response to triangular variation of the maximum conductance ($G_{syn}$) for the synaptic receptors positioned at all points at $D_{path}$=600 μm, and F-$G_{syn}$ curve. Arrows indicate the ascending and descending phase of $G_{syn}$.

To explicitly evaluate the influence of the three VA factors on the location dependence of dendritic excitability, the anatomically reconstructed MN was reduced using our recently developed two-compartment model that analytically retained the VA factors of its original cell as well as whole cell properties measured at the soma such as input resistance ($R_N$) and system time constant ($\tau_m$) [Kim H, Major L A, Jones K E (2009) Derivation of cable parameters for a reduced model that retains asymmetric voltage attenuation of reconstructed spinal motor neuron dendrites. J Comput Neurosci 27: 321-336] (FIG. 2A). The systematic comparison between the full anatomical model and the reduced model was conducted in two steps. Firstly, all levels of input/output relations were compared at $D_{path}$=600 μm with respect to: the passive membrane properties, the dendritic excitability with PIC channels in the dendrites, and the cellular excitability for firing output at the soma. Then, we constructed multiple two-compartment models and matched their excitability for $D_{path}$ values along the dendrites of the full model.

Figure 2B:
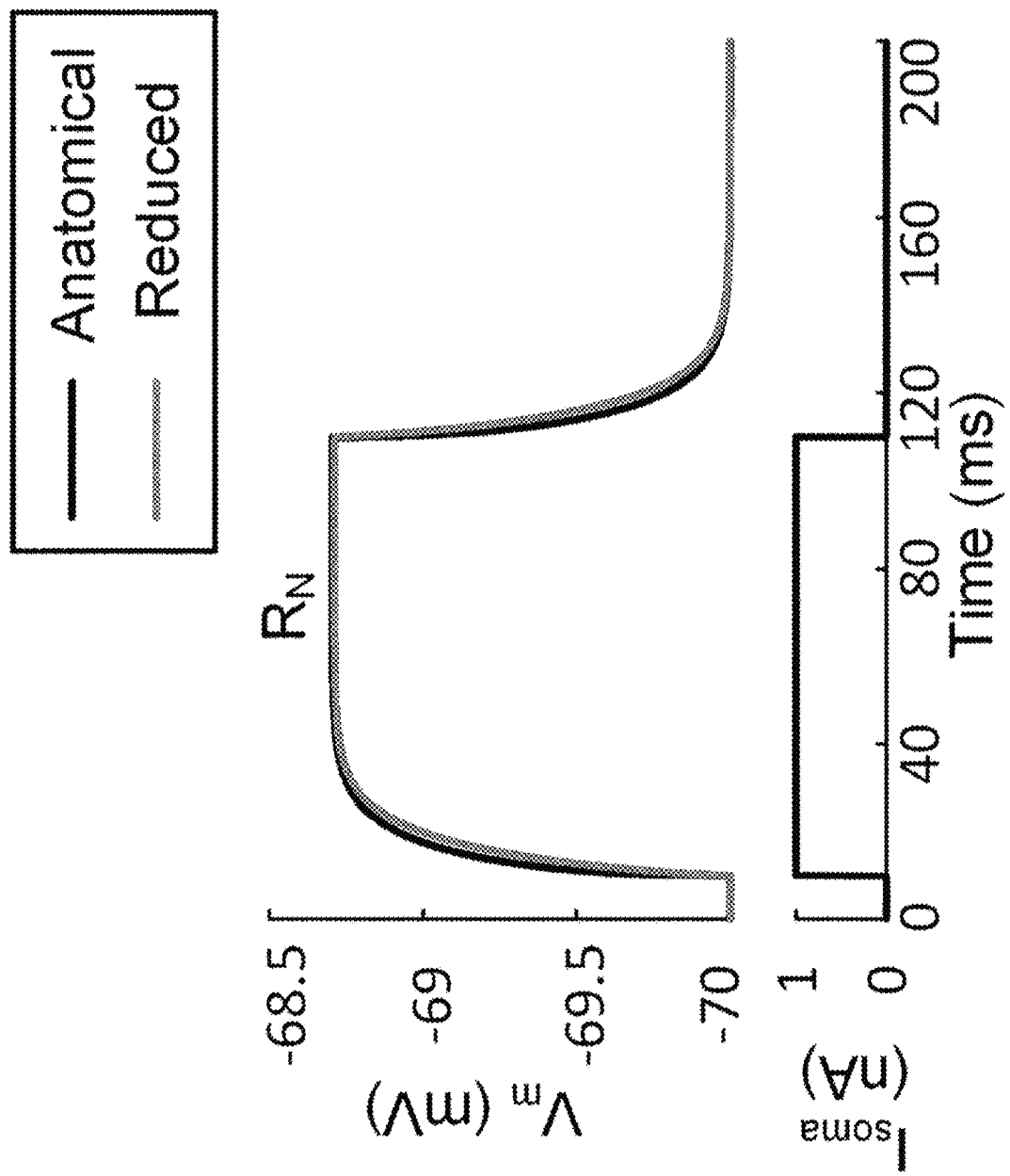
Figure 2C:
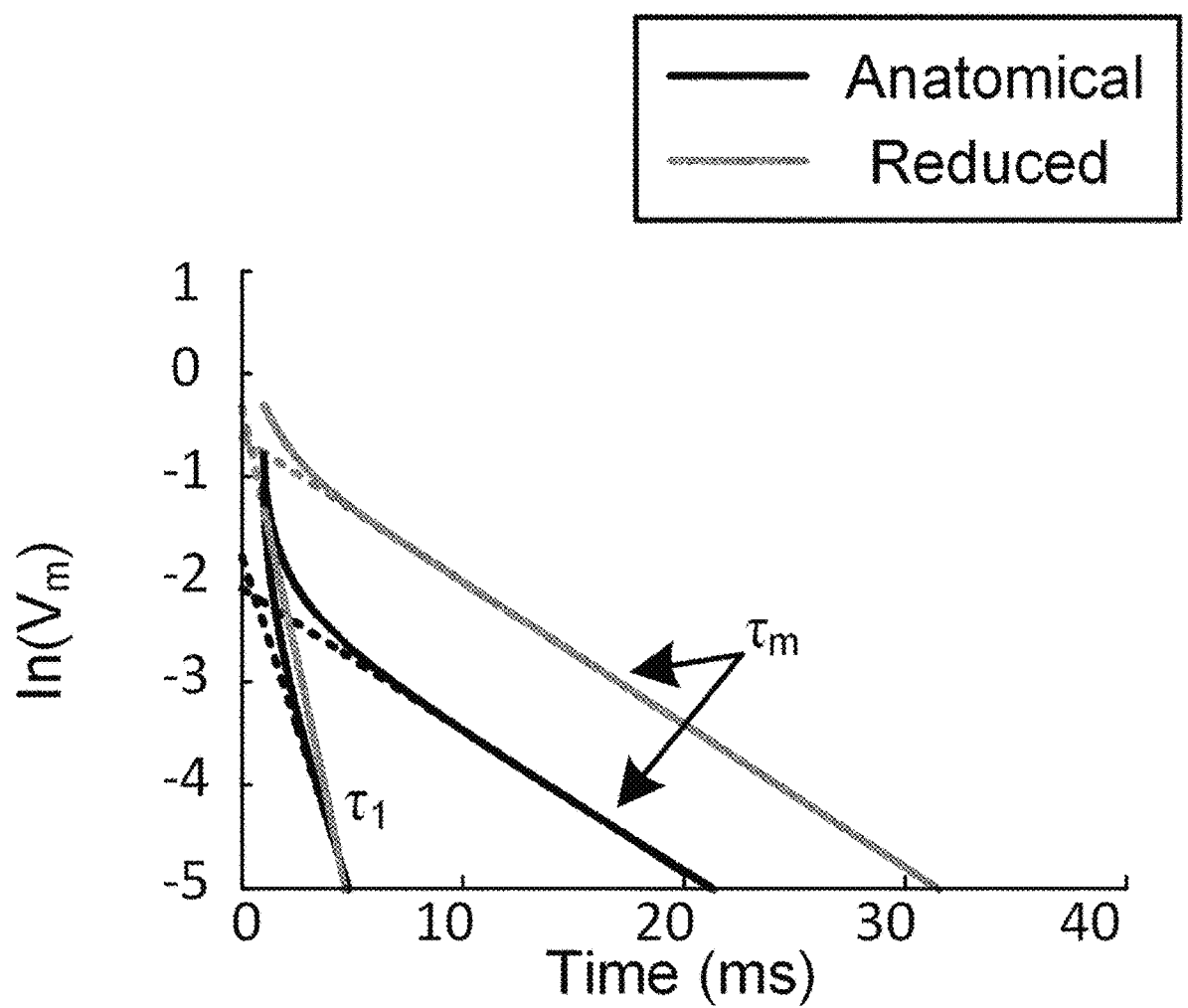
Figure 2D:
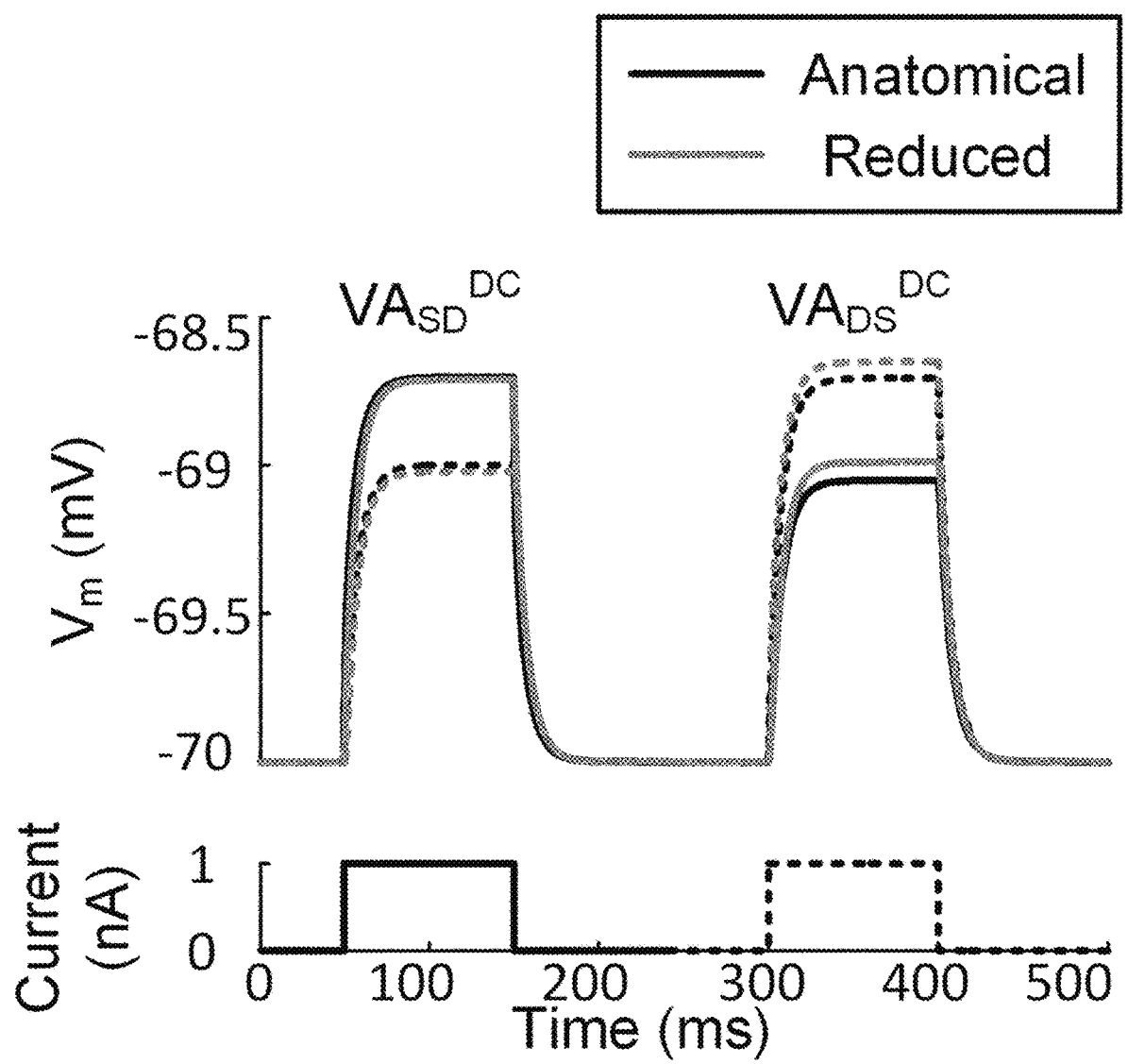
Figure 2E:
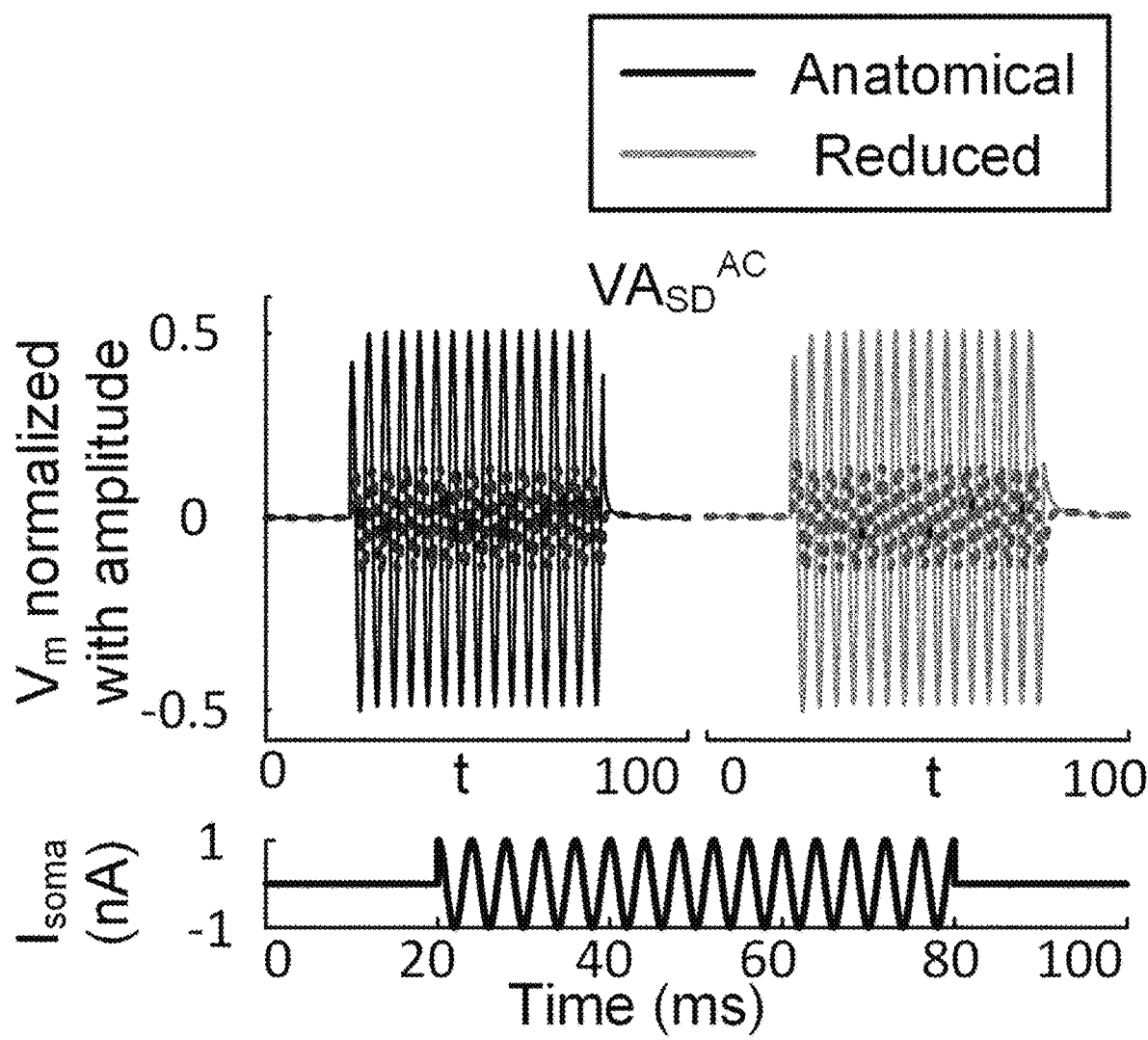
Figure 2F:
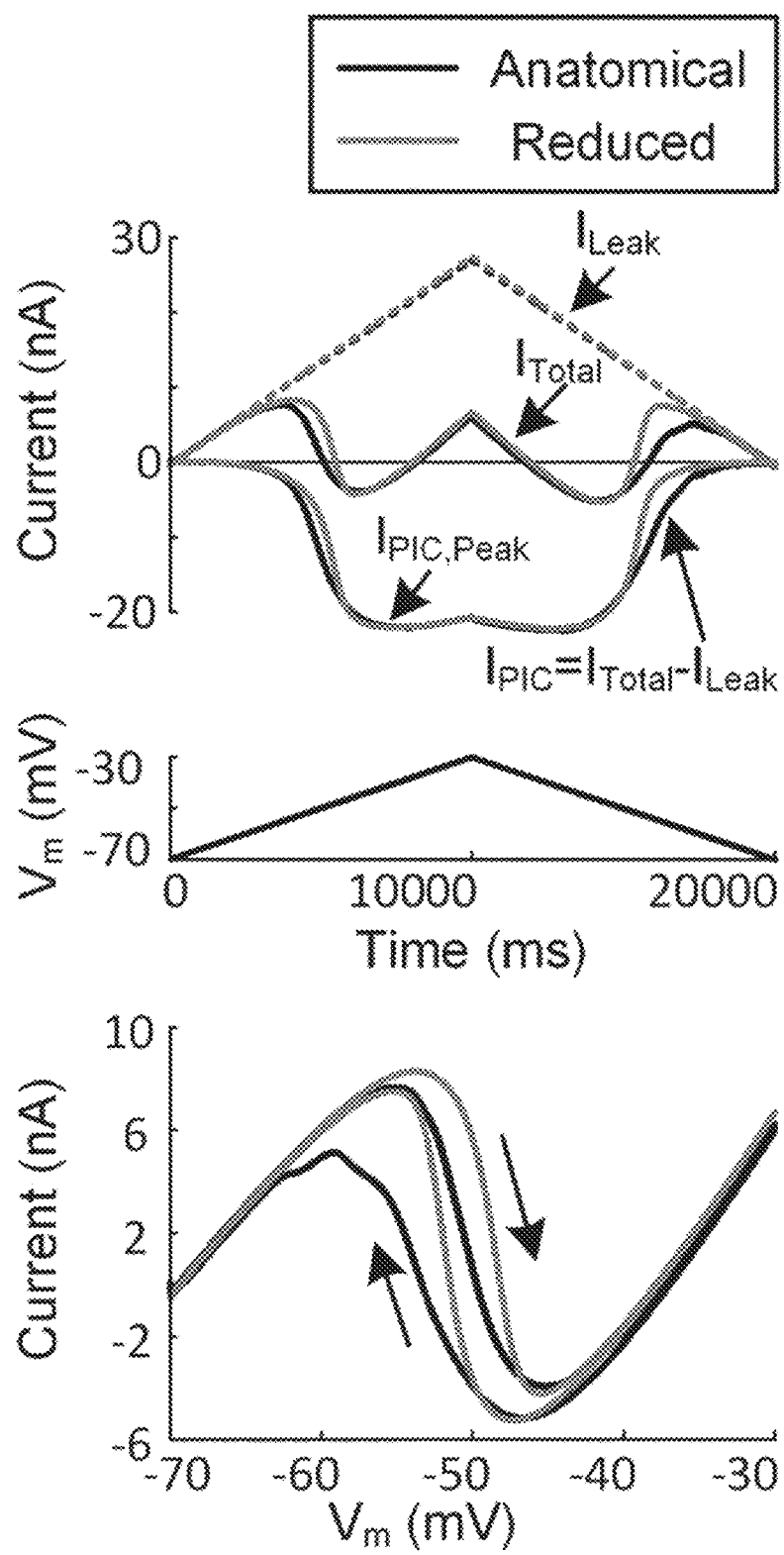

Comparison of passive dynamics of the reduced and full models. The five system parameters (i.e. $R_N$, $T_m$, and $VA_{SD}^{DC}$, $VA_{DS}^{DC}$ and $VA_{SD}^{AC}$ for $D_{path}$=600 μm) used to solve for the passive properties of the reduced model, were sufficient to replicate the desired passive membrane features of the anatomical model (FIGS. 2B and 2C). The time course of depolarization and repolarization in response to the long lasting step current at the soma was very similar in both cases (FIG. 2B)), despite the slight difference in the second time constant (or equalizing time constant, τ1 in FIG. 2C). For the purpose of comparison, brief current pulse with smaller amplitude was applied to the soma for the anatomical (blue) than reduced (red) case resulting in the downward shift of the voltage response for the anatomical case in FIG. 2C. The somatic and dendritic membrane potentials measured for the calculation of $VA_{SD}^{DC}$ were identical, whereas those for the $VA_{DS}^{DC}$ were slightly larger by about 0.09% in the reduced model compared to the anatomical model at steady state (FIG. 2D). The similarity of dendritic depolarization in the two models, by the same dendritically injected current, indicates that the input resistance at the dendrite of the reduced model captures the input resistance of the complex dendritic network of the anatomical model at the $D_{path}$=600 μm. The amplitude ratio (i.e. $VA_{SD}^{AC}$) between somatic and dendritic membrane potential in response to 250 Hz-AC input to the soma was same between two models (FIG. 2E).

Figure 2G:
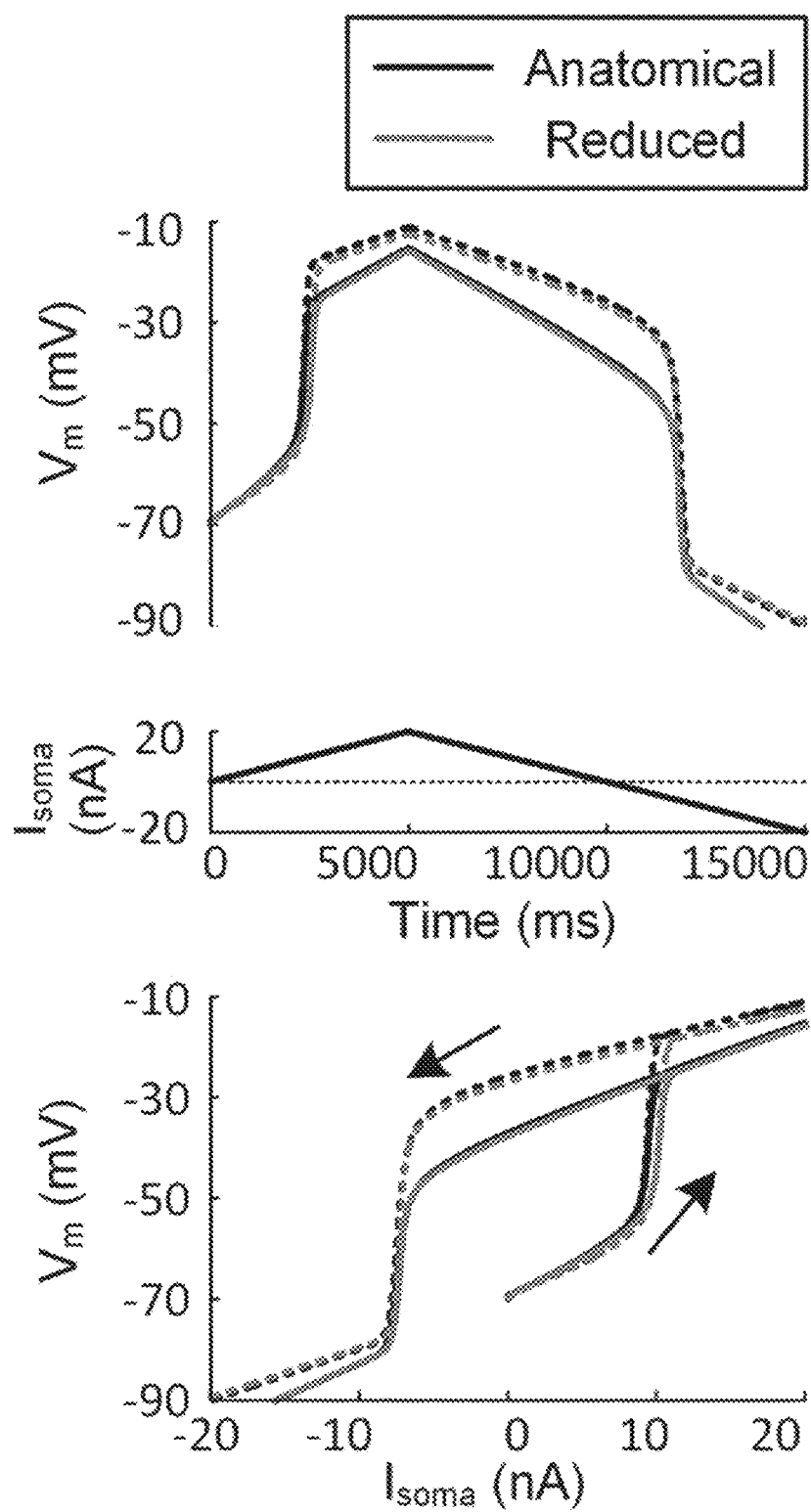
Figure 2H:
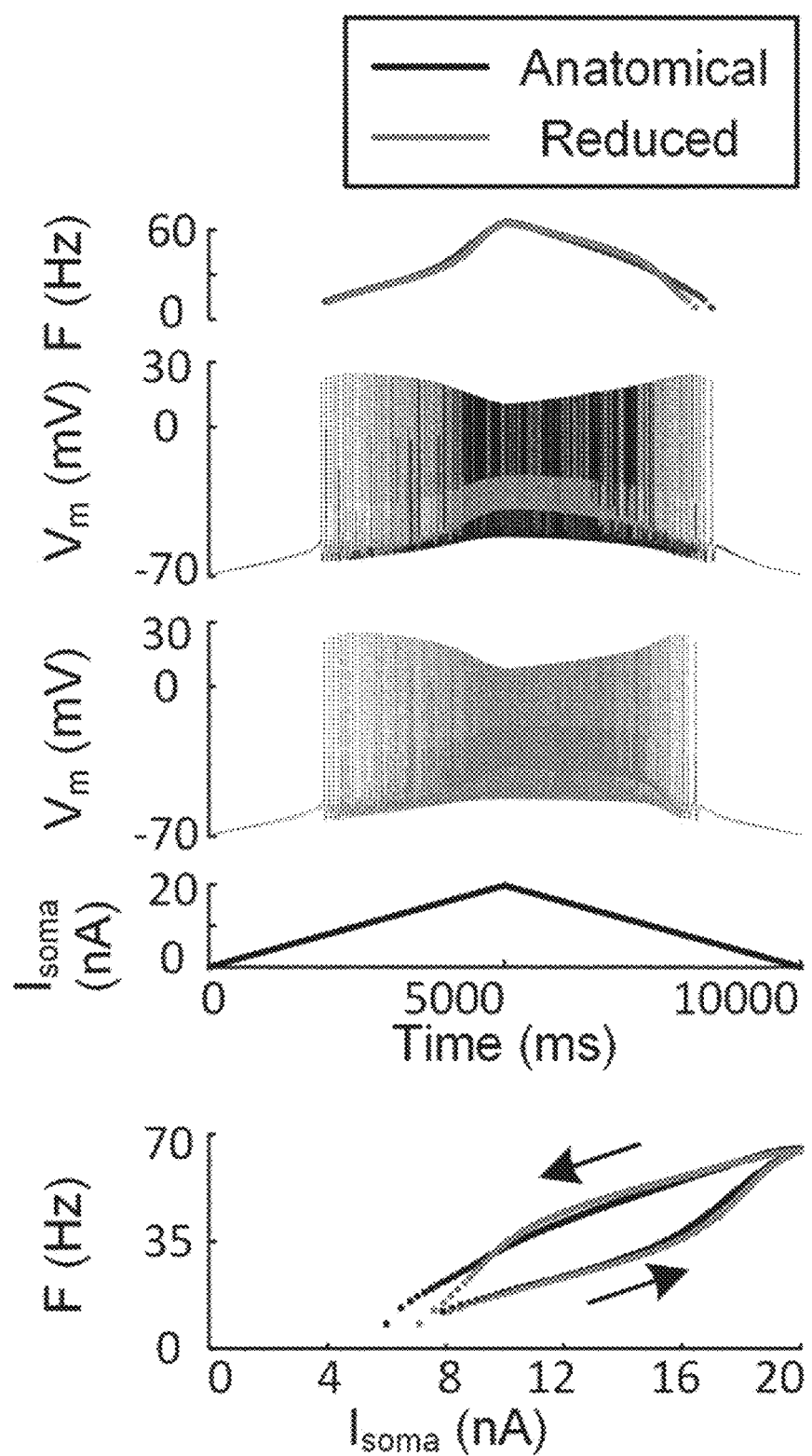

Comparison of dendritic PIC activation. The next comparison was for dendritic PIC activation during either slow-ramp voltage or current clamp applied to the soma, while blocking all active currents generated at the soma. In this way, we could isolate the influence of the DC signal attenuation (i.e. $VA_{SD}^{DC}$ and $VA_{DS}^{DC}$) on the PIC activation from that of the AC signal attenuation (i.e. $VA_{SD}^{AC}$). The maximum conductance of the Ca channels in the dendrite of the reduced model was fit to the peak current measured in the anatomical model during triangular voltage clamp simulations ($I_{PIC}$, Peak in FIG. 2F). During the rising phase of triangular voltage clamp the two models produced similar N-shaped dynamics of the total current ($I_{Total}$, top panel in FIG. 2F). The consequence of PIC activation was a long lasting depolarization (plateau potential, top panel in FIG. 2G) at both soma and dendrites during the triangular current stimulation to the soma. The delayed offset of the PIC during the falling phase of voltage clamp relative to the rising phase of voltage clamp resulted in hysteresis of the current/voltage relationships (bottom panels in FIGS. 2F and 2G). A difference between two models was the earlier onset and slower offset of the PIC in the anatomical dendrites, probably due to the variance in the input resistance of individual dendritic branches at the $D_{path}$ of 600 μm. However, this difference was negligible in current clamp conditions during activation of the plateau potential (FIG. 2G).

Figure 2I:
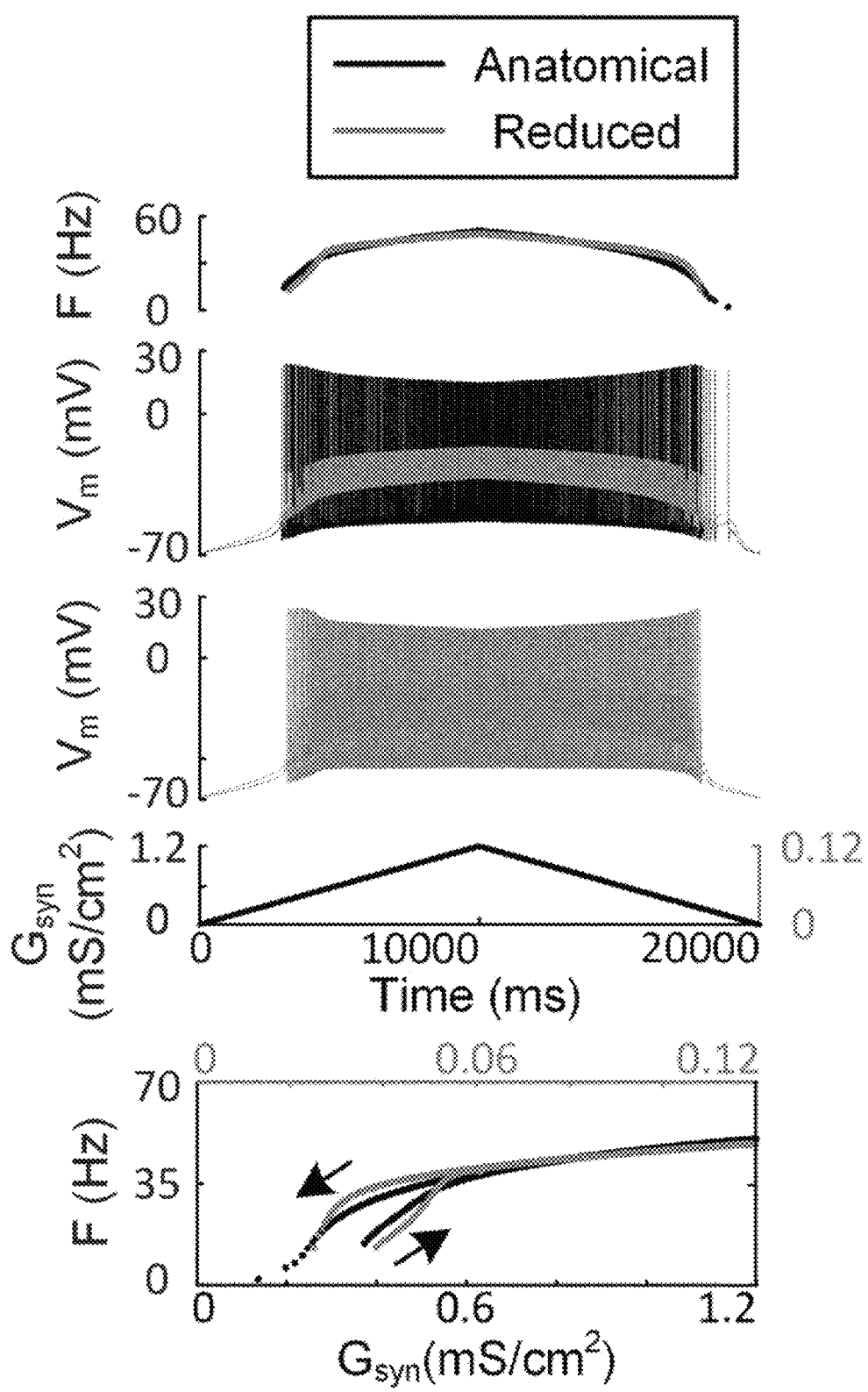
Figure 3A:
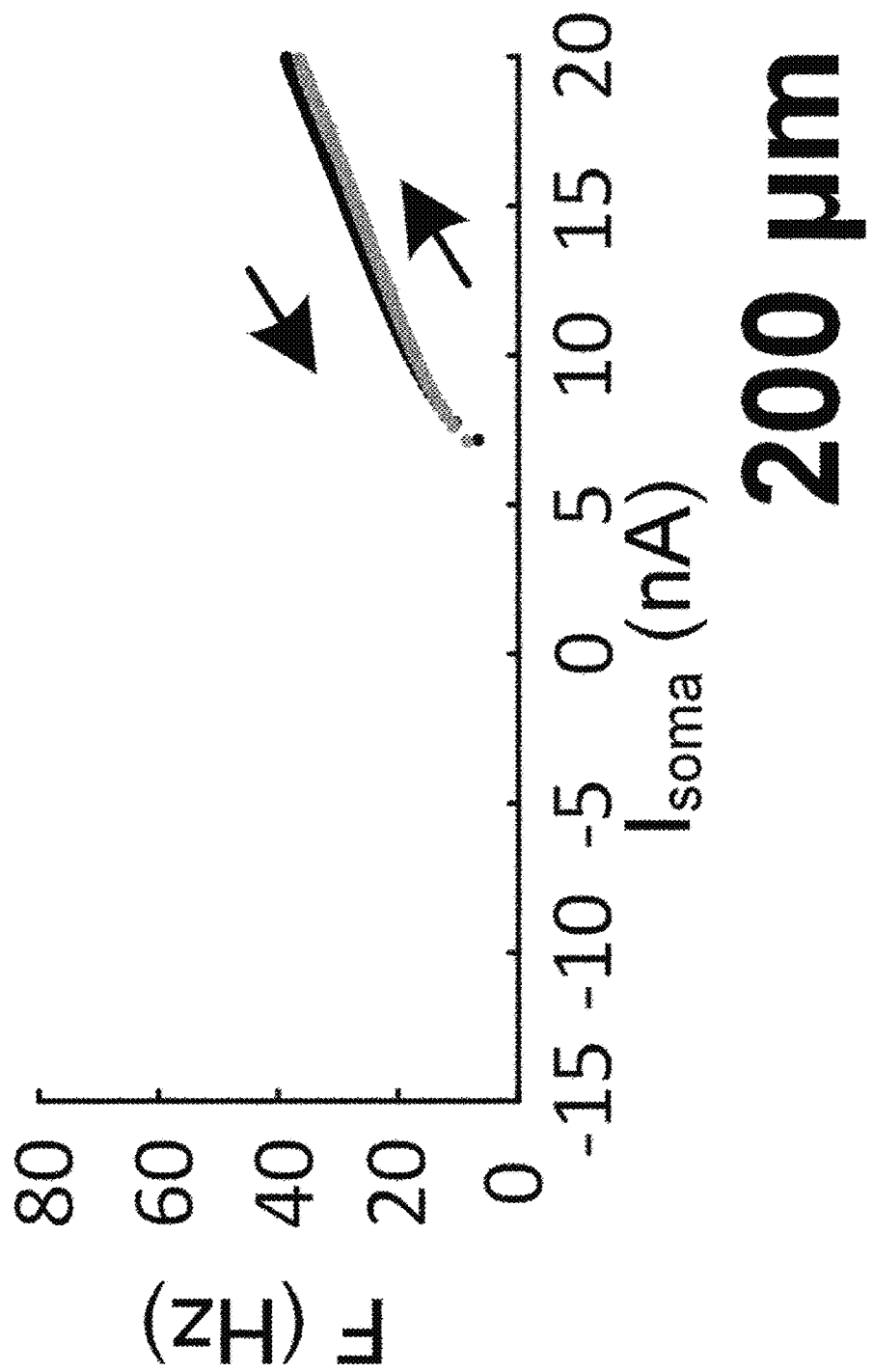
FIGS. 3A, 3B, 3C, 3D, 3E, 3F, 3G, and 3H show cellular excitability of the anatomical (blue) and reduced (red) model with different locations of PIC channels in the dendrites.
Figure 3B:
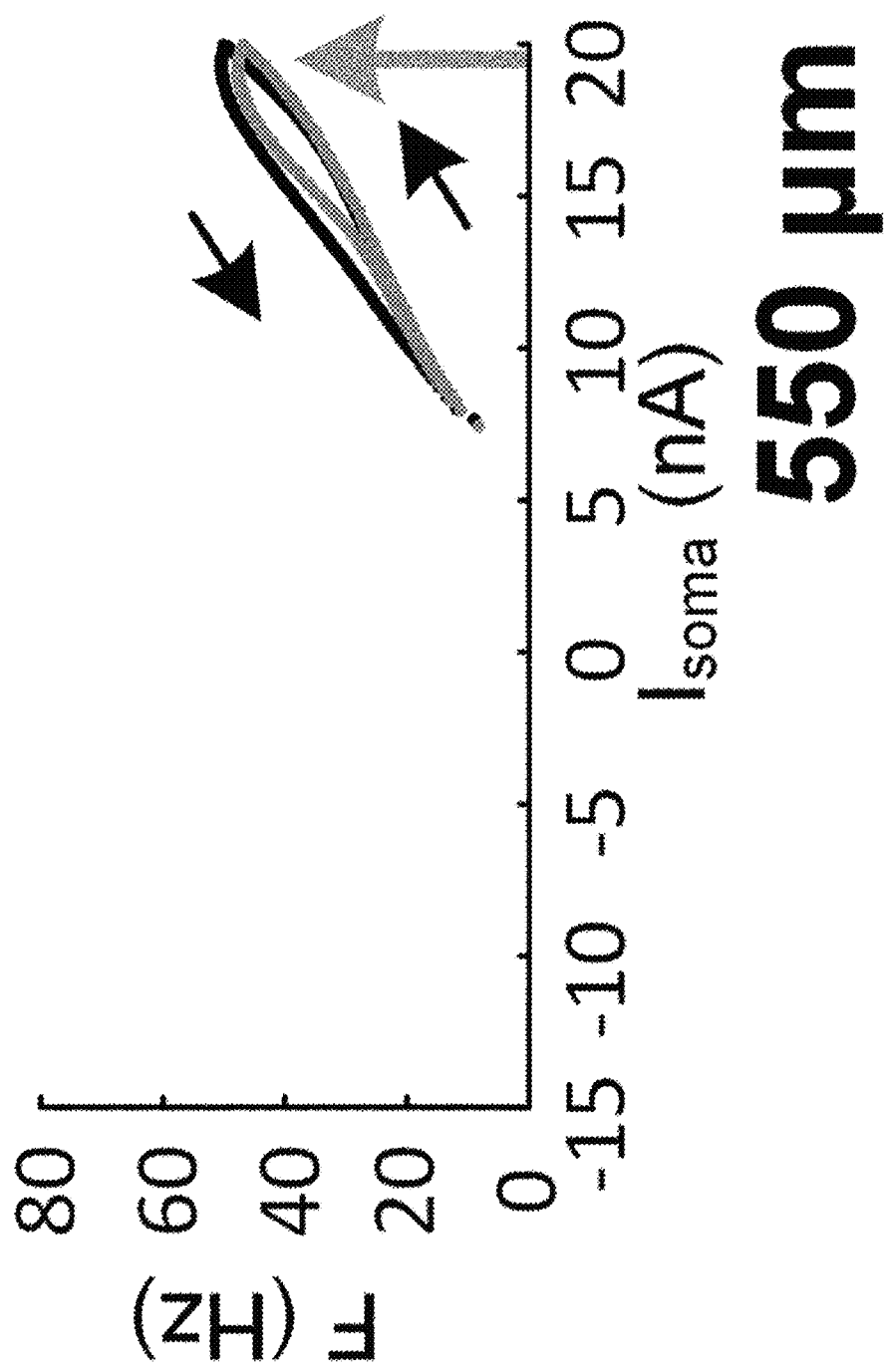
Figure 3C:
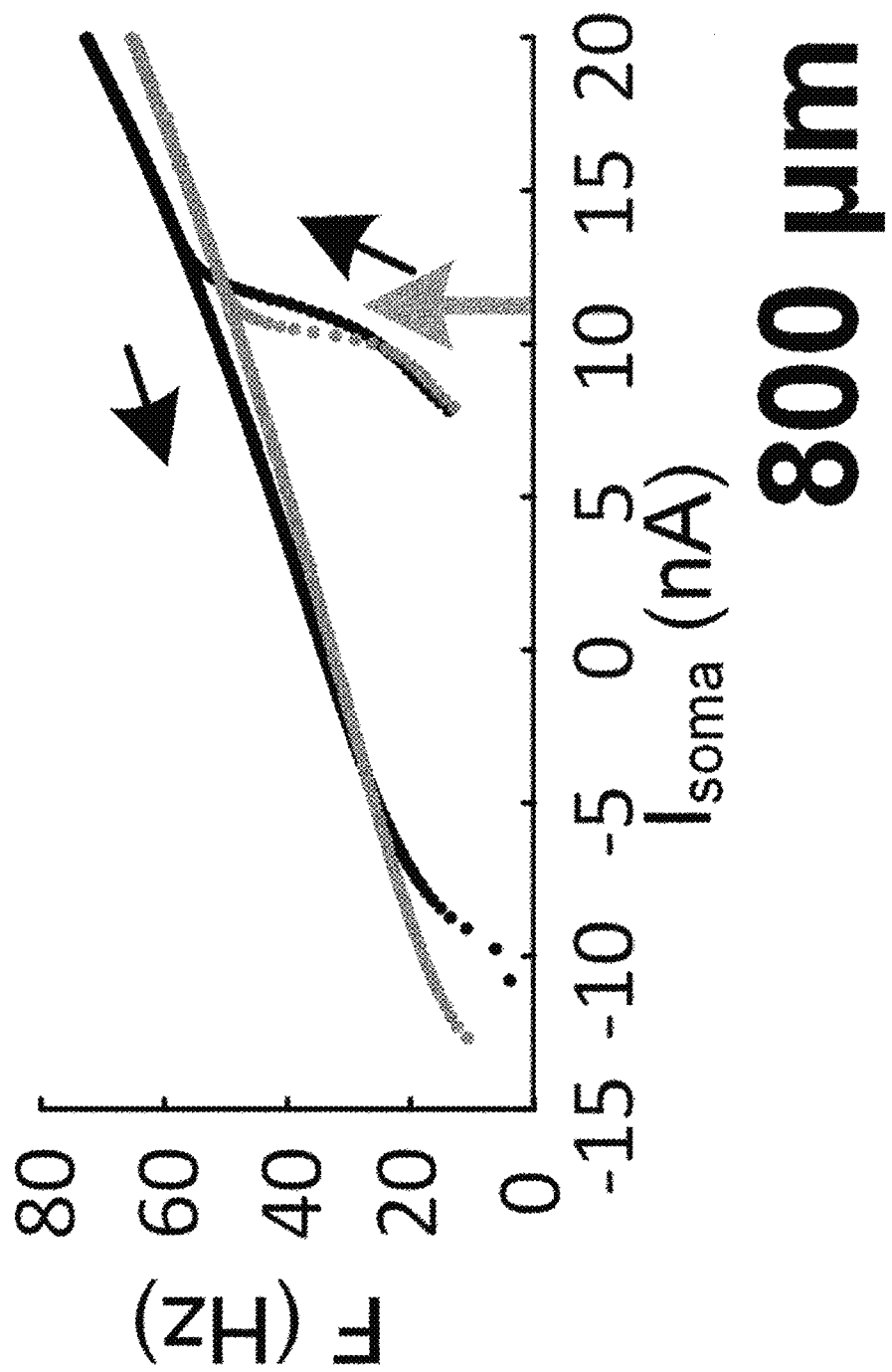
Figure 3D:
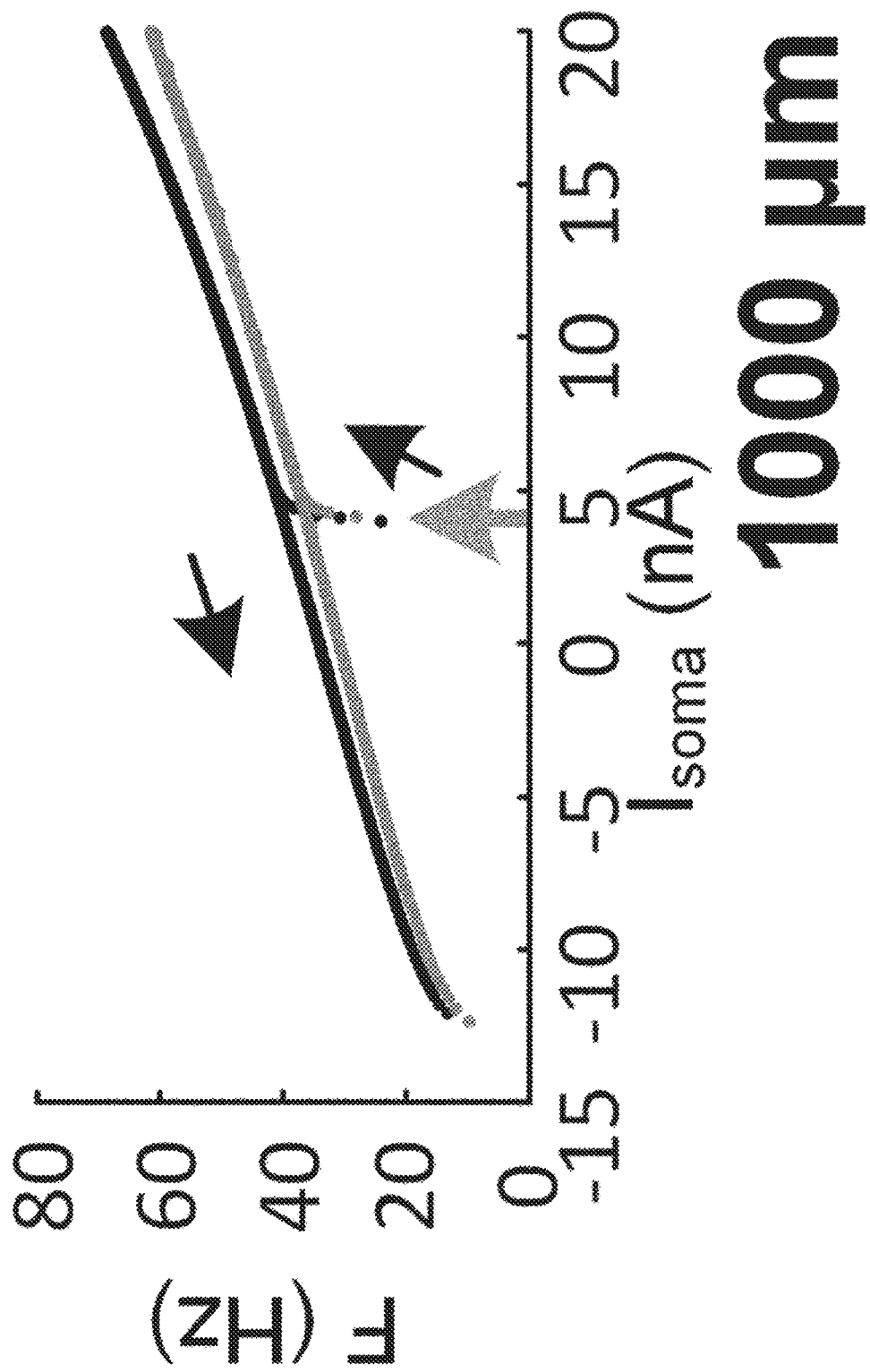
Figure 3E:
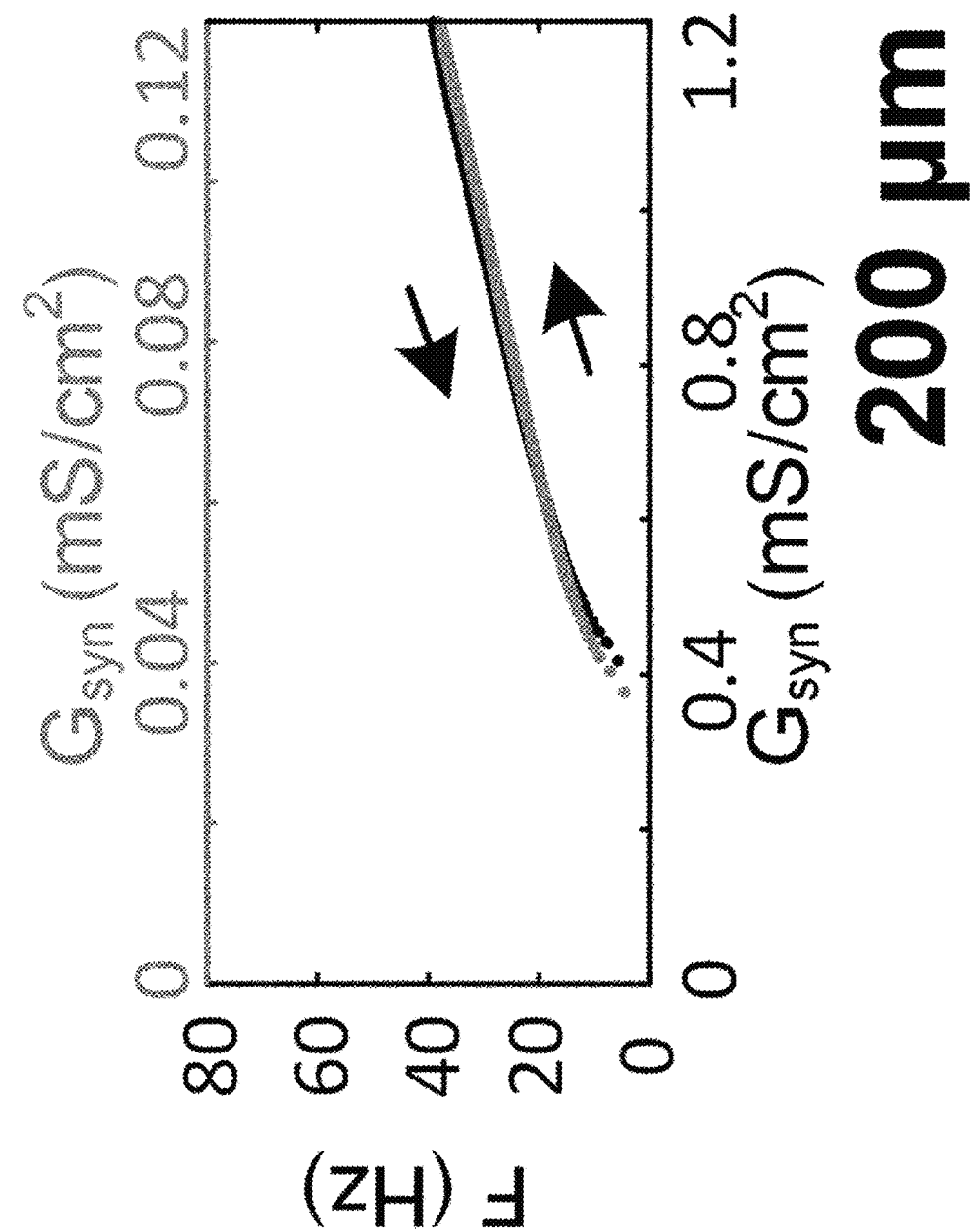
Figure 3F:
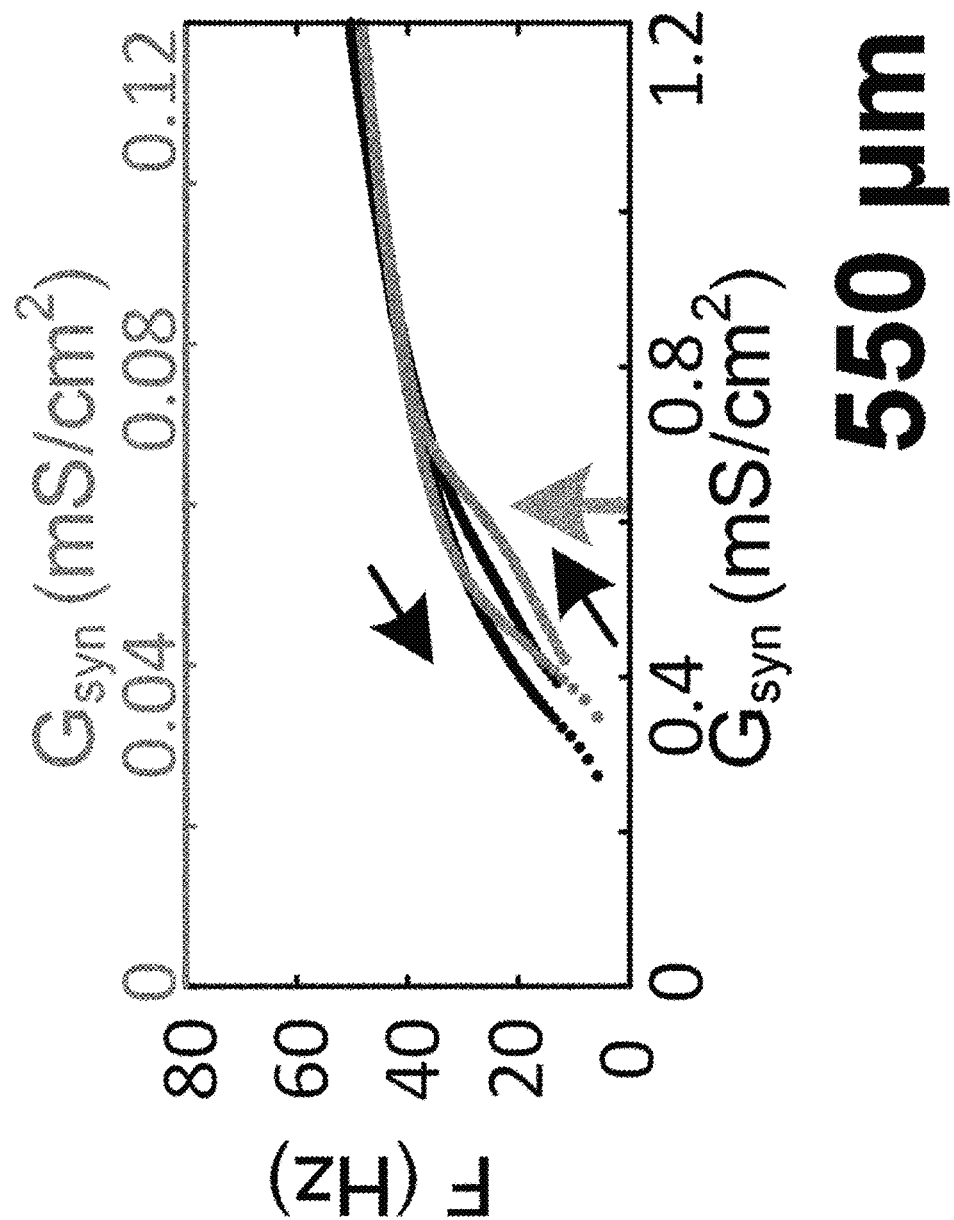
Figure 3G:
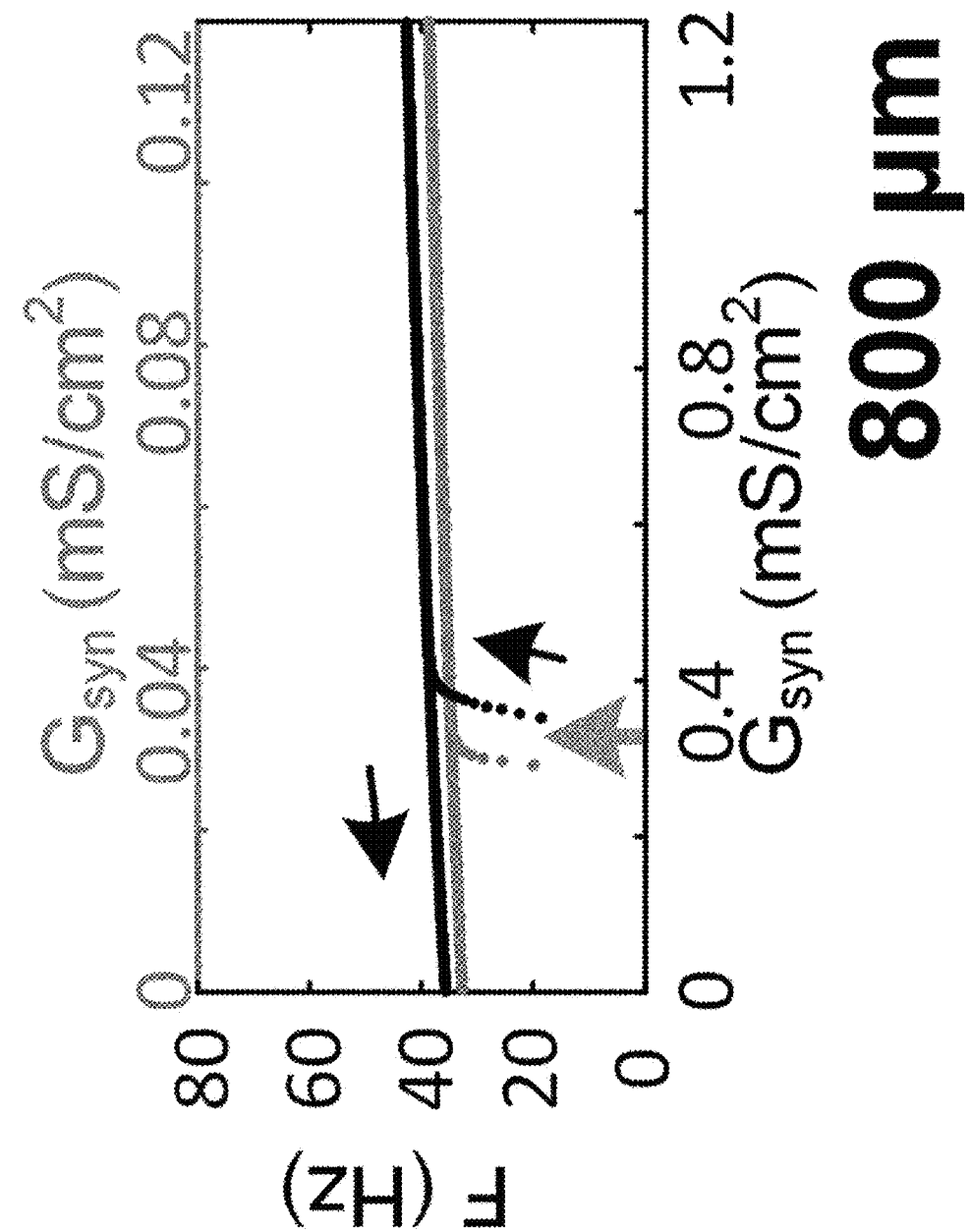
Figure 3H:
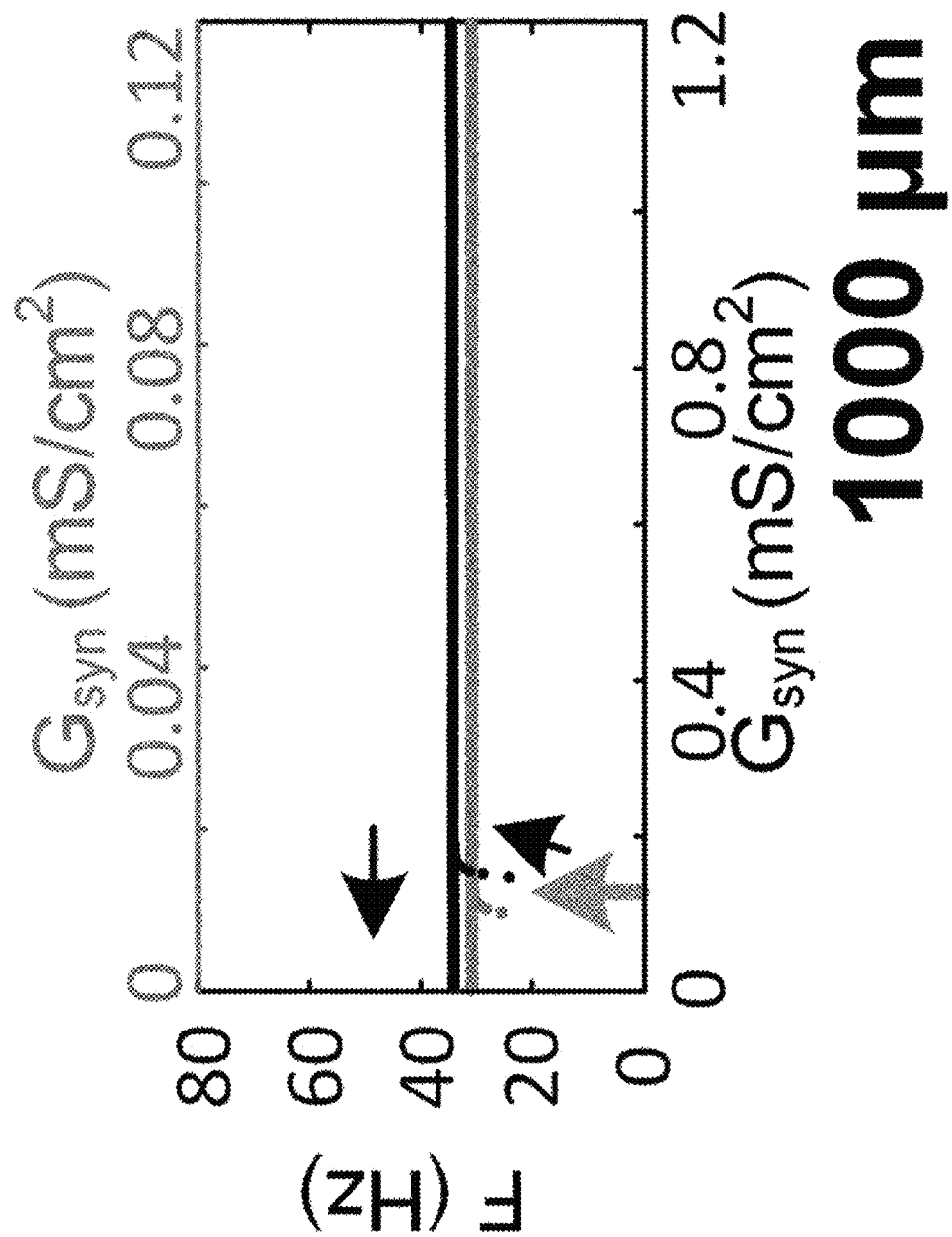

Comparison of firing responses. Because the activation of PIC channels in the dendrites is influenced by action potentials propagating into the dendrites [Kim H, Jones K E (2012) The retrograde frequency response of passive dendritic trees constrains the nonlinear firing behaviour of a reduced neuron model. PLoS One 7: e43654], we compared firing patterns in response to the triangular current stimulation to the soma between the anatomical and reduced models. In the presence of Ca PIC channels, the two models showed similar nonlinear firing behavior (bottom panel in FIG. 2H), i.e. counter-clockwise hysteretic frequency-current (F-$I_{soma}$) relationship with sustained firing below the current threshold for spike initiation. The firing rate at the end of the descending phase of the current injection is greater for the anatomical model because the slower offset of the PIC results in more inward current. Overall there was a good match of firing rate behavior in the two models. FIG. 2I shows that the reduced model also matched the full model even in the case where tonic synaptic inputs interacted with PIC channels in the dendrites [Bennett D J, Hultborn H, Fedirchuk B, Gorassini M (1998) Synaptic activation 550 of plateaus in hindlimb otoneurons of decerebrate cats. J Neurophysiol 80: 2023-2037]. The amplitude of membrane potentials at the soma and dendrites was similar between the two models during the triangular changes in $G_{syn}$. Consistent with the relationship with somatically injected current (bottom panel in FIG. 2I), the anatomical model had the faster onset of the PIC channels and longer duration of sustained firing below the threshold for the spiking than the reduced model.

Comparison of the effects of varying the distance for PIC location. The above results only applied to the case where the PIC channels were localized to 600 microns from the soma in both the full and reduced models. The inventors of present invention next varied the location of the ion channels that generate the PIC. For each location, a new two-compartment model was created and matched to the passive properties ($R_N$, $T_m$ and three VAs) of the anatomical model. This required location dependent alterations in the VA parameters of the reduced models. The PIC channel density of both models was adjusted to maintain a constant peak of $I_{PIC}$ determined at the $D_{path}$=600 μm [Lee R H, Heckman C J (1999) Paradoxical effect of QX-314 on persistent inward currents and bistable behavior in spinal motoneurons in vivo. J Neurophysiol 82: 2518-2527].

FIGS. 3A, 3B, 3C, 3D, 3E, 3F, 3G, and 3H show cellular excitability of the anatomical (blue) and reduced (red) model with different locations of PIC channels in the dendrites. In FIGS. 3A-3H, the neuron models and stimulation protocols were same as those used in FIGS. 2H-2I except for variation of PIC channel location in the dendrites. FIGS. 3A-3D show firing rates (F) in response to triangular current stimulation to the soma ($I_{soma}$). FIGS. 3E-3H show firing rates (F) in response to triangular variation of maximum conductance ($G_{syn}$) of excitatory synaptic receptors in the dendrites. In FIGS. 3A-3H, the direction of black arrows indicates the ascending and descending phase of triangular current stimulation and change in $G_{syn}$. The gray arrows indicate the current and $G_{syn}$ threshold for activating plateau potentials at different distances from the soma. Note the negative relation between the distance and input threshold. At different locations in the dendrites, the three VA factors were $VA_{SD}^{DC}$={0.91, 0.77, 0.69, 0.63}, $VA_{DS}^{DC}$={0.96, 0.79, 0.57, 0.38} and $VA_{SD}^{AC}$={0.65, 0.31, 0.18, 0.12}; the density of Ca PIC channels were $G_{CaL}$={1.14, 1.27, 1.95, 4.1 mS/cm$^2$} in the anatomical and {0.11, 0.122, 0.132, 0.189 mS/cm$^2$} in the reduced model; the passive parameter values of the reduced model were $G_{m, S}$={0.078, 0.132, 0.174, 0.2 mS/cm$^2$}, $G_{m, D}$={0.179, 0.143, 0.1, 0.07 mS/cm$^2$}, $G_C$={0.918, 0.244, 0.114, 0.06 mS/cm$^2$}, $C_{m, S}$={0.609, 1.077, 1.211, 1.302 µF/cm$^2$}, $C_{m, D}$={1.239, 0.903, 0.764, 0.62 µF/cm$^2$}. Parameter values in the parentheses are in the order of increasing distance from 200 to 1000 µm.

In general, the reduced model was able to predict the overall firing pattern of the anatomical model at all distances from the soma during either somatic current stimulation or synaptic input (FIGS. 3A-3H). As the PIC channels moved towards the dendritic terminals, both threshold current and synaptic conductance for the activation of plateau potential decreased (gray arrows in FIGS. 3A-3H). These results indicate that the more distant the location of the PIC channels in the dendrites, the more "excitable" the cell is.

Dependency of Dendritic Excitability on the VA Factors

The results of the previous section showed that systematic changes in the VA factors for the two compartment models allowed representation of the spatial variation in the threshold for activating plateau potentials along the path of the complex MN dendrites. Therefore, we next used the two-compartment models to evaluate how the VA factors influence dendritic excitability. To achieve this, a sensitivity analysis of the effect of the VA factors on dendritic PIC activation was conducted for PIC channels located at different distances from the soma.

Figure 4A:
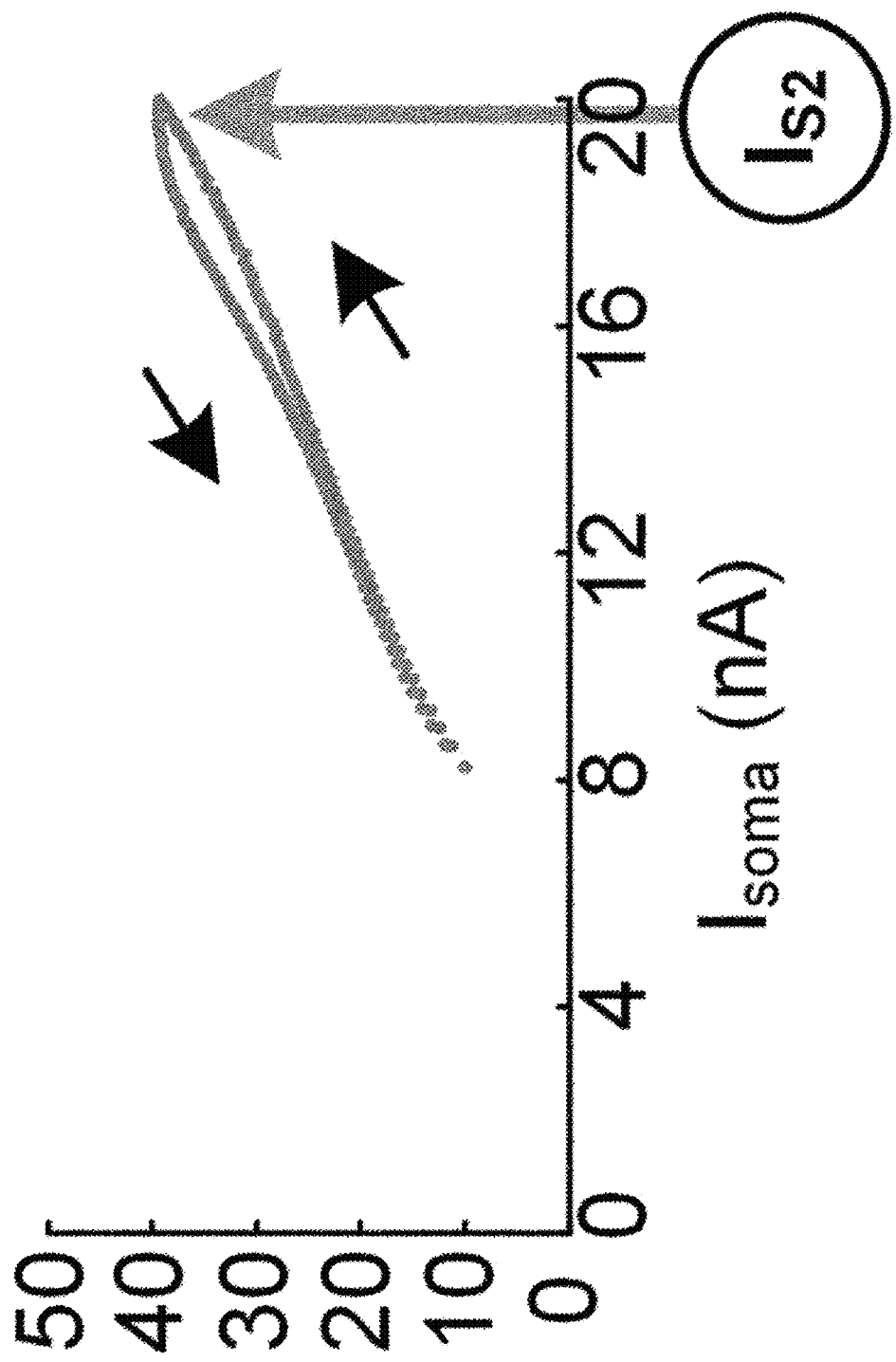
Figure 4B:
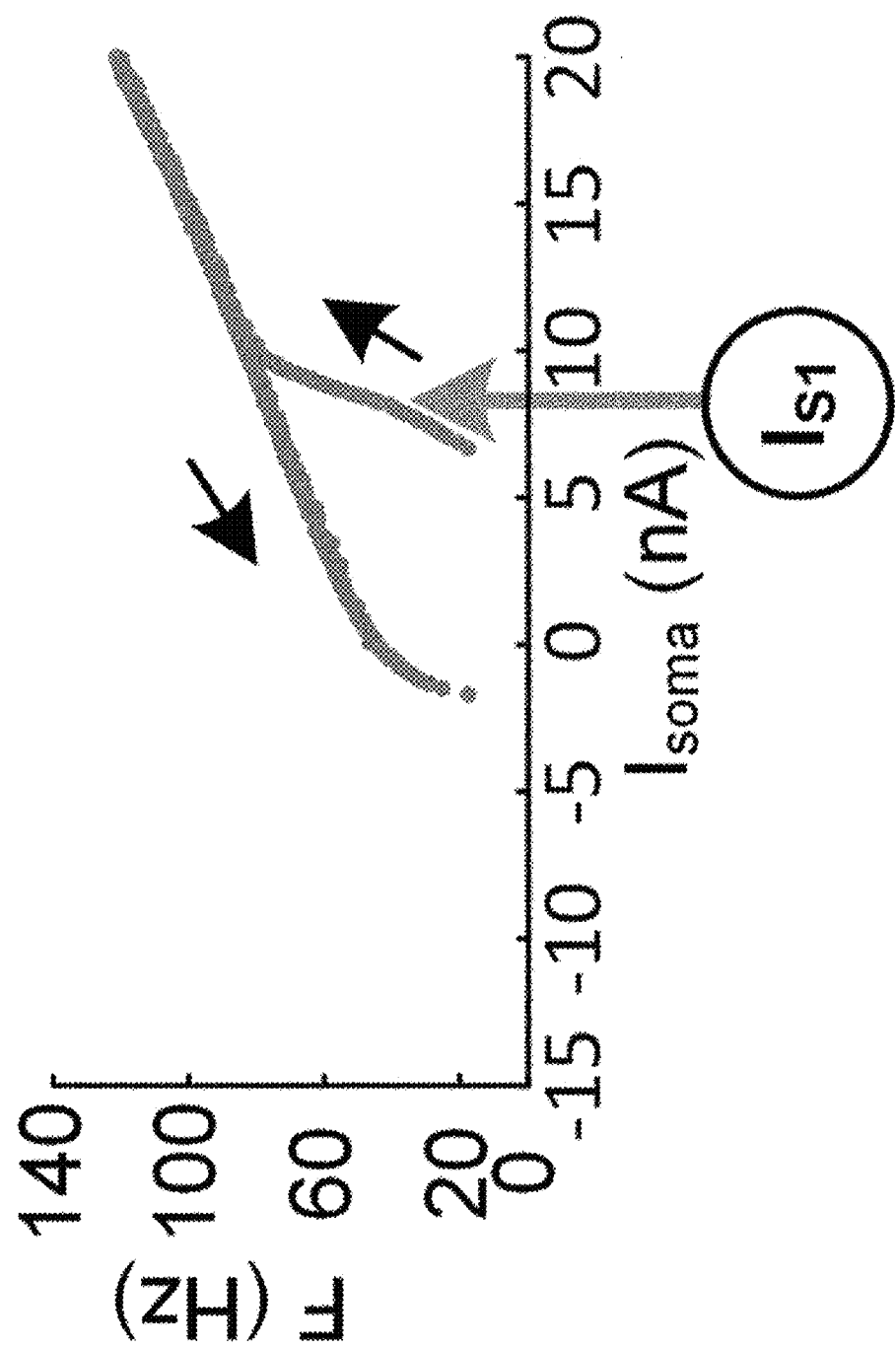
Figure 4C:
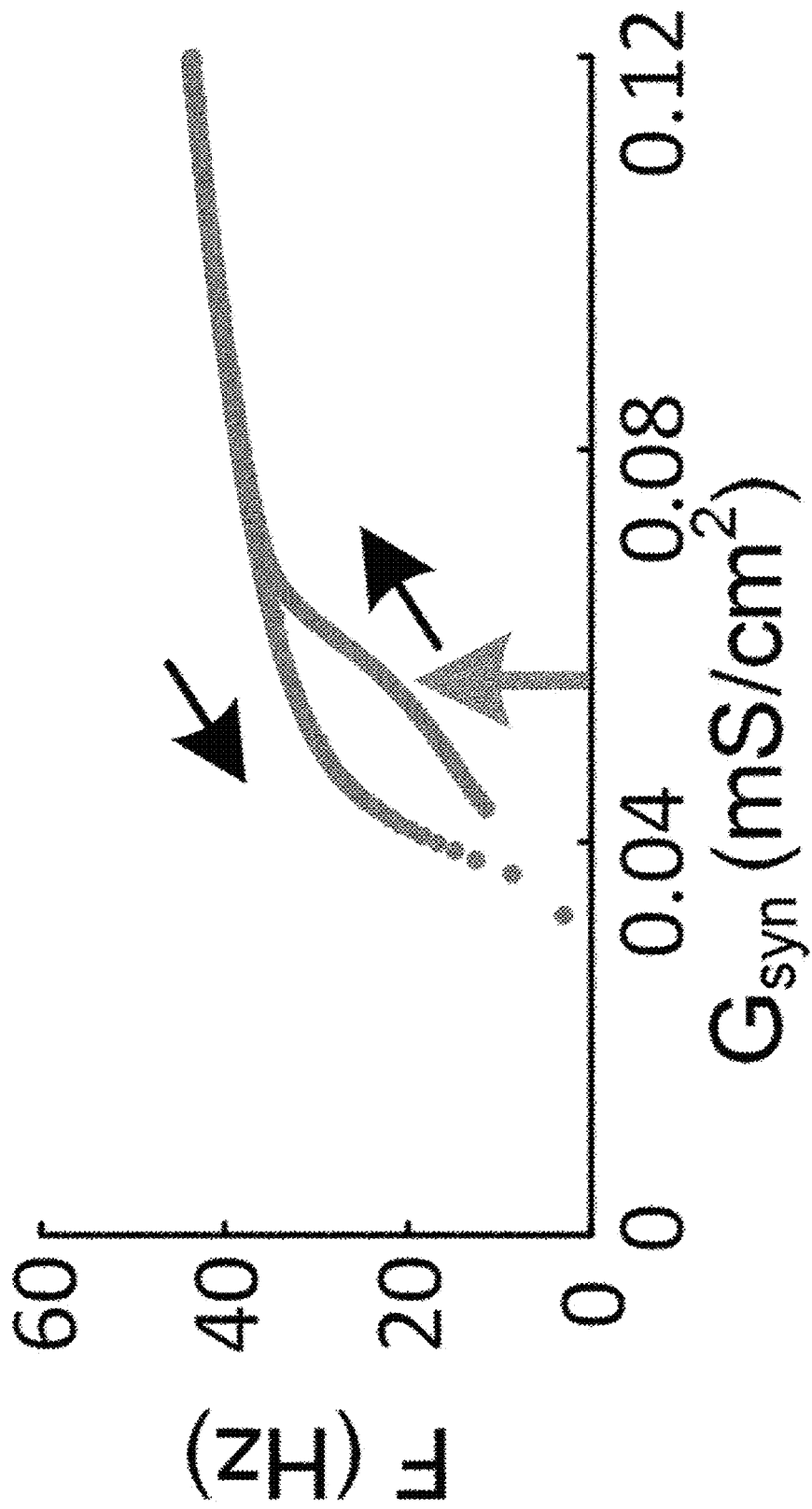
Figure 4D:
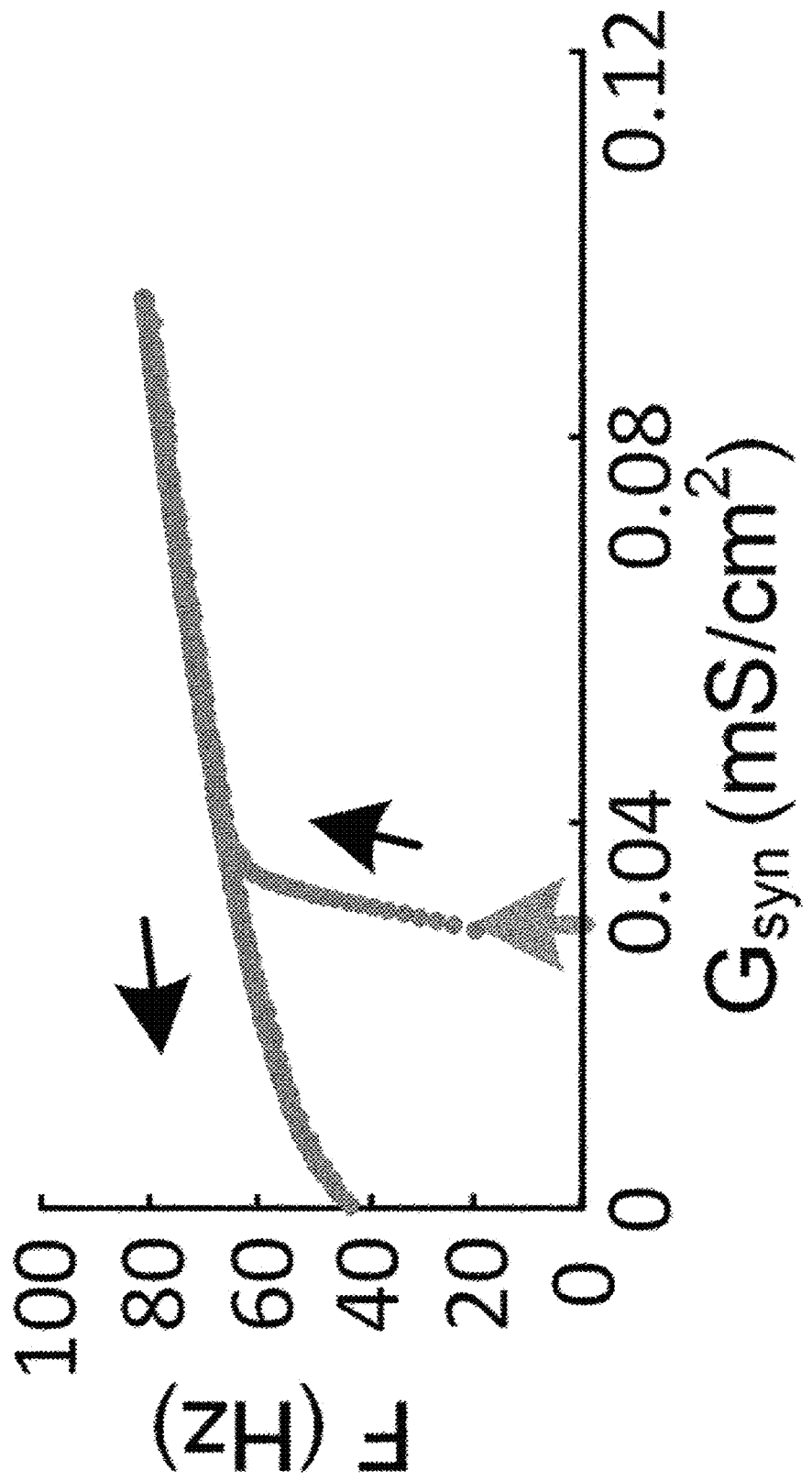
Figure 4F:
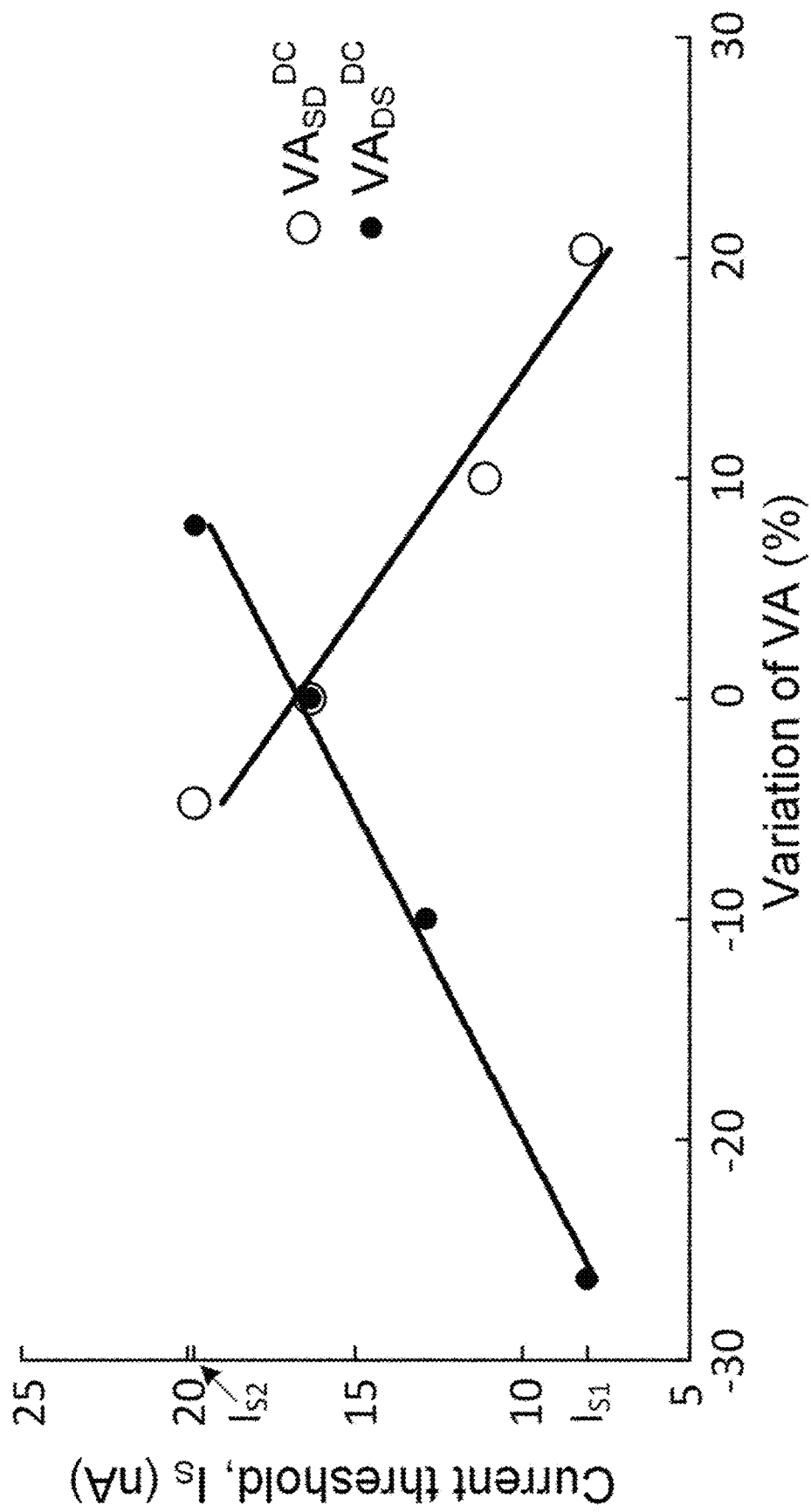

FIGS. 4A, 4B, 4C, 4D, 4E, and 4F show sensitivity of cellular excitability to the VA factors. Using the same reduced model and ramp stimulation protocols used in FIGS. 2H and 2I, F-$I_{soma}$ and F-$G_{syn}$ relationships were simulated while varying individual VA factors independently. FIGS. 4A and 4B show curves with $VA_{SD}^{DC}$ decreased by 4.7% and increased by 20.4% from its original value (0.76). Circled letters, $I_{S1}$ (8.1 nA) and $I_{S2}$ (19.8 nA), on vertical gray lines indicate decreased and increased current threshold for initiating firing acceleration as a result of changing the $VA_{SD}^{DC}$. Black arrows indicate the rising and falling phase of triangular current stimulation to the soma. FIGS. 4c and 4D show F-$G_{syn}$ curves with $VA_{SD}^{DC}$ changed by the same variation (%) as applied to FIGS. 4A and 4B. Vertical gray arrows indicate increased (about 0.055 mS/cm$^2$, left column) and decreased (about 0.029 mS/cm$^2$, right column) threshold-$G_{syn}$ for the firing acceleration as a result of varying the $VA_{SD}^{DC}$. Black arrows indicate the rising and falling phase of triangular change in $G_{syn}$ at the dendrite. FIG. 4E shows the percent variation in individual VA factors ($VA_{SD}^{DC}$, $VA_{DS}^{DC}$, $VA_{SD}^{AC}$) to produce the firing acceleration at either $I_{S1}$ or $I_{S2}$. 0% represents the original values of VA factors and minus sign in the ordinate indicates the decrease in VA factor values. FIG. 4F shows relationship of threshold current (IS) for the firing acceleration and the percent variation in DC VA factors. Data points were fitted to a linear regression line.

Sensitivity of cellular excitability to the VA factors. Triangular currents were injected at the soma to generate frequency-current curves and the threshold for PIC activation was estimated from the acceleration in firing. When $VA_{SD}^{DC}$ was decreased by 4.7% from its original value (0.76), a high threshold was detected at 19.8 nA and labeled $I_{S2}$ (FIG. 4A). Similarly, when $VA_{SD}^{DC}$ was increased by 20.4%, a low current threshold for this acceleration was detected at 8.1 nA and labeled $I_{S1}$ (FIG. 4B). A shift from $I_{S2}$ to $I_{S1}$ represents a hyperpolarizing shift of the threshold, indicating an increase in excitability. The sensitivity of each of the three voltage attenuation factors was inferred by measuring the amount of variation required to alter the acceleration in firing between $I_{S1}$ and $I_{S2}$.

The inventors of the present invention inferred high sensitivity to a VA factor when small variations were required to achieve the target thresholds. The threshold for the firing acceleration was more sensitive to changes in the DC than AC VA factors (FIG. 4E). Variation of the DC VA factors changed the threshold targets in opposite directions. Increasing the attenuation from the dendrites to the soma by decreasing $VA_{DS}^{DC}$ resulted in an increase in excitability. In contrast, increasing the attenuation in the opposite direction, $VA_{SD}^{DC}$, produced a decrease in excitability. Therefore, we conclude that $VA_{SD}^{DC}$ is positively correlated, whereas $VA_{DS}^{DC}$ is negatively correlated with excitability (FIG. 4F). The slope of the regression lines indicates that current threshold is most sensitive to voltage attenuation from the soma to the dendrites. The relatively modest effects of changes in $VA_{SD}^{AC}$ also increase excitability.

Similar effects of varying individual voltage attenuation factors were found in the case where the PIC was activated by synaptic conductances applied to the dendrites (FIGS. 4C and 4D). The three voltage attenuation factors showed the same correlations with excitability to synaptic input as current input to the soma. That is, increases in $VA_{SD}^{DC}$ increased excitability, whereas increases in $VA_{DS}^{DC}$ or $VA_{SD}^{AC}$ decreased excitability.

Role for the VA factors in the spatial profile of dendritic excitability. The inventors of the present invention next explored how the voltage attenuation factors affected the relationship between PIC location along the dendrites and its threshold for activation.

FIGS. 5A, 5B, 5C, 5D, 5E, 5F, 5G, and 5H show spatial dependence of cellular excitability on $VA_{DS}^{DC}$ and $VA_{SD}^{AC}$. In FIGS. 5A-5H, all simulation conditions were identical to those used in FIGS. 4A-4F except for systematically varying the values of the $VA_{DS}^{DC}$ and $VA_{SD}^{AC}$. Note the inverse order of firing patterns with increasing distance compared to the physiological case (FIGS. 3A-3H). FIGS. 5A-5D show F-$I_{soma}$ relationships. FIGS. 5E-5H show F-$G_{syn}$ relationships. The direction of black arrows indicates the ascending and descending phase of triangular current stimulation and change in $G_{syn}$. The gray arrows indicate the current and $G_{syn}$ threshold for activating plateau potentials at different distances from the soma. At different locations, the $VA_{DS}^{DC}$ and $VA_{SD}^{AC}$ were {0.47, 0.6, 0.78, 0.876} and {0.65, 698 0.31, 0.18, 0.5}. The passive parameter values of the reduced model were $G_{m, S}$={0.228, 0.183, 0.117, 0.067 mS/cm$^2$}, $G_{m, D}$={0.019, 0.079, 0.181, 0.276 mS/cm$^2$}, $G_C$={0.099, 0.135, 0.204, 0.234 mS/cm$^2$}, $C_{m, S}$={1.644, 1.387, 0.766, 1.617 µF/cm$^2$}, $C_{m, D}$={0.134, 0.499, 1.373, 0.352 µF/cm$^2$}. Parameter values in the parentheses are in the order of increasing distance from 200 to 1000 µm.

When all three VA factors were constrained to biophysical values obtained from simulations with the anatomical MN model (FIG. 1A), moving the PIC location close to the soma resulted in an increase in PIC activation threshold: the closer the PIC, the greater the current (either injected or synaptic) required to activate it (FIGS. 3A-3H). In the present analysis, we held $VA_{SD}^{DC}$ at its physiological values for each PIC distance and varied $VA_{DS}^{DC}$ and $VA_{SD}^{AC}$. The results of these changes were striking in that the spatial order of the PIC activation observed in the physiological case (FIGS. 3A-3H) could be inverted, as illustrated in FIGS. 5A-5H. That is, PIC threshold activation shifted to lower values as its location was moved closer to the soma.

Figure 5A:
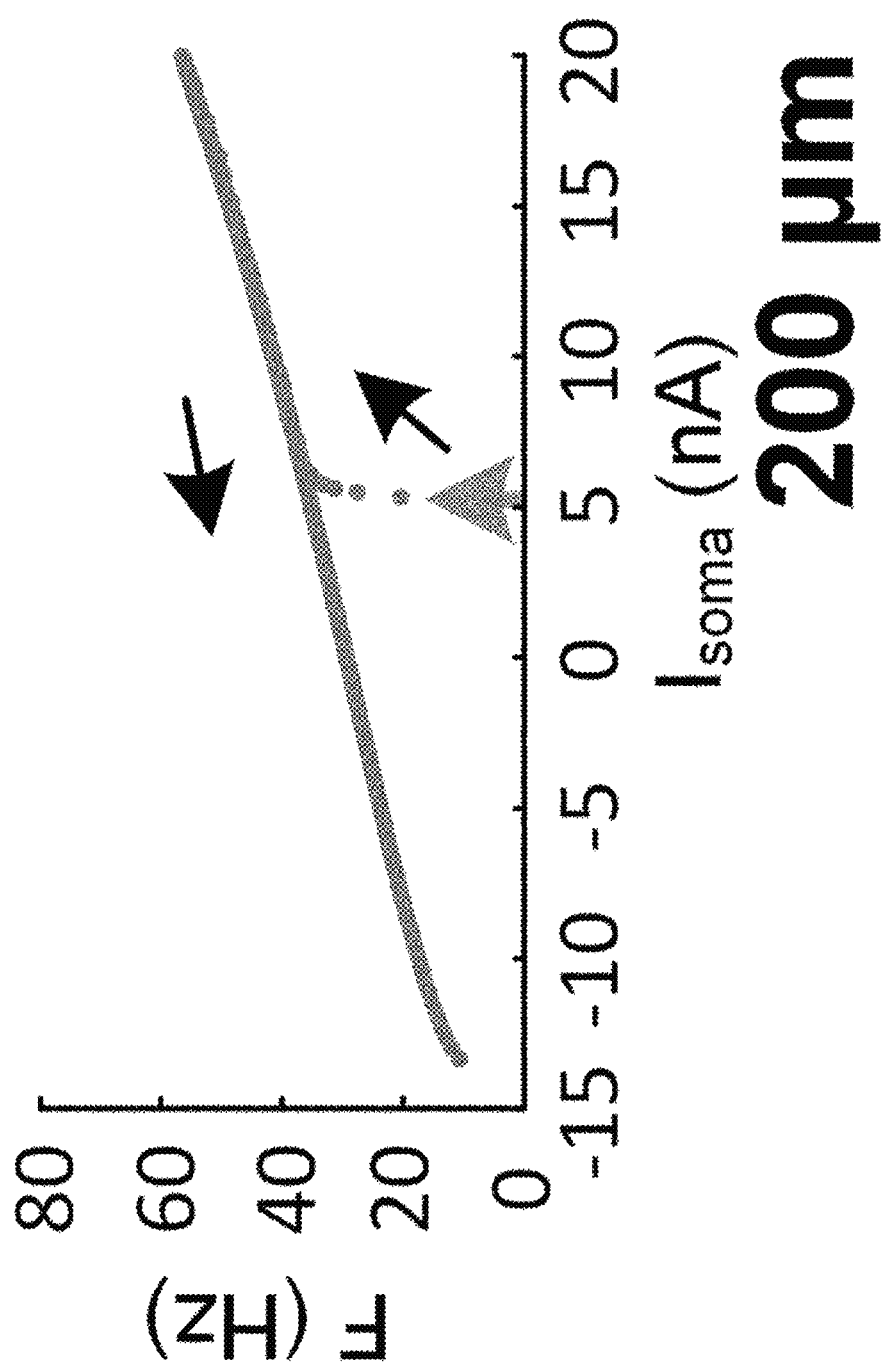
FIGS. 5A, 5B, 5C, 5D, 5E, 5F, 5G and 5H show spatial dependence of cellular excitability on $VA_{DS}^{DC}$ and $VA_{SD}^{AC}$.
Figure 5B:
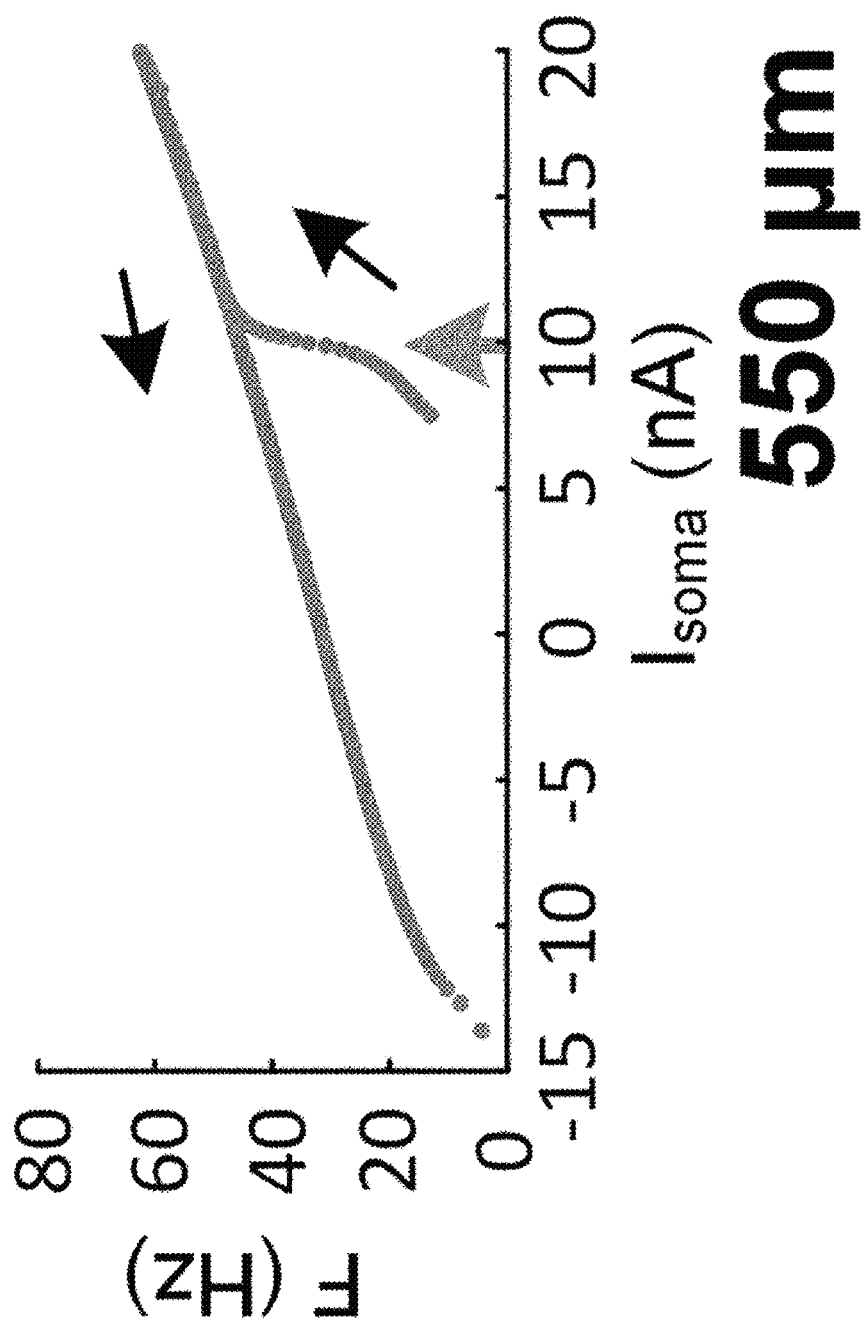
Figure 5C:
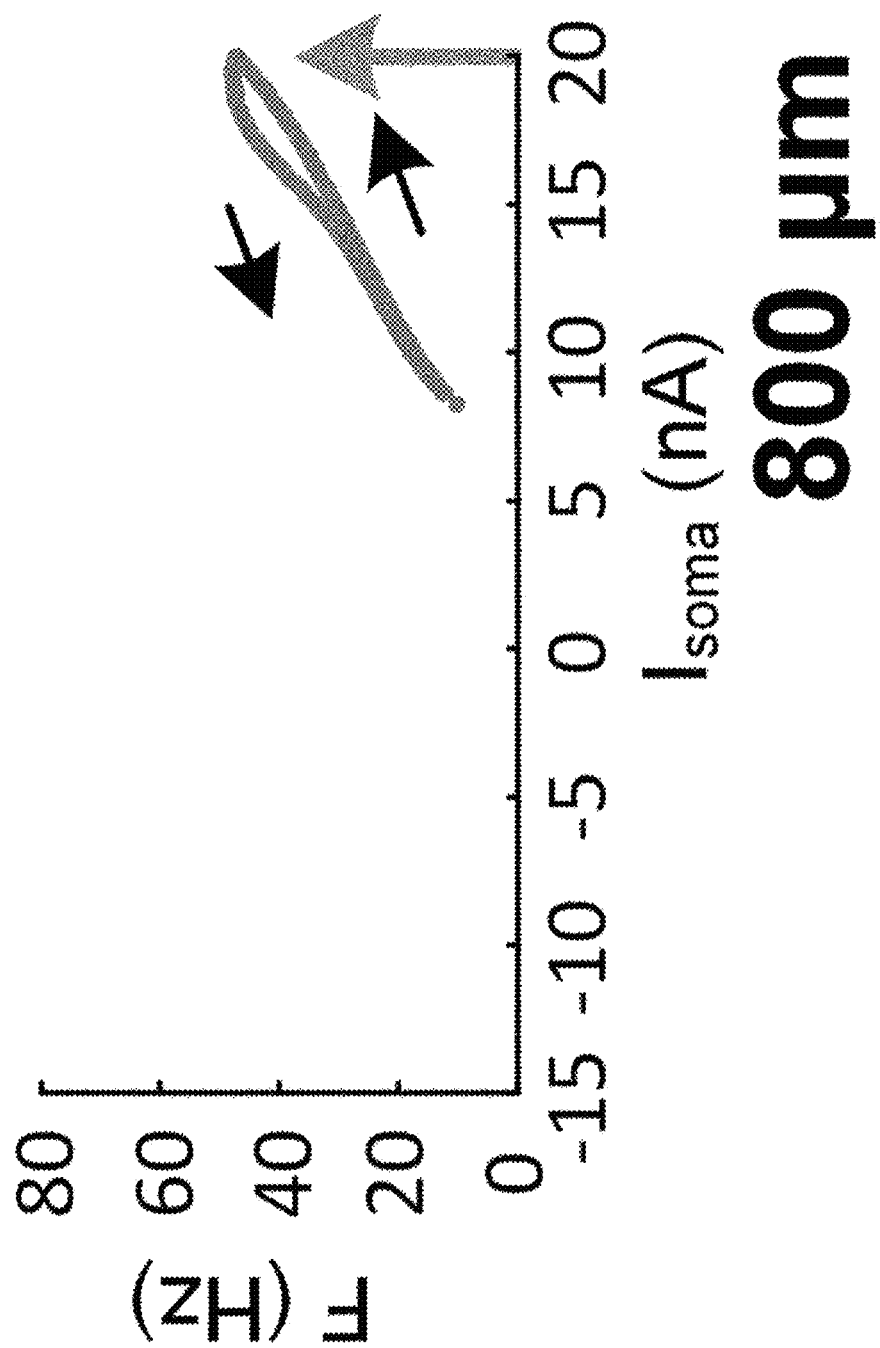
Figure 5D:
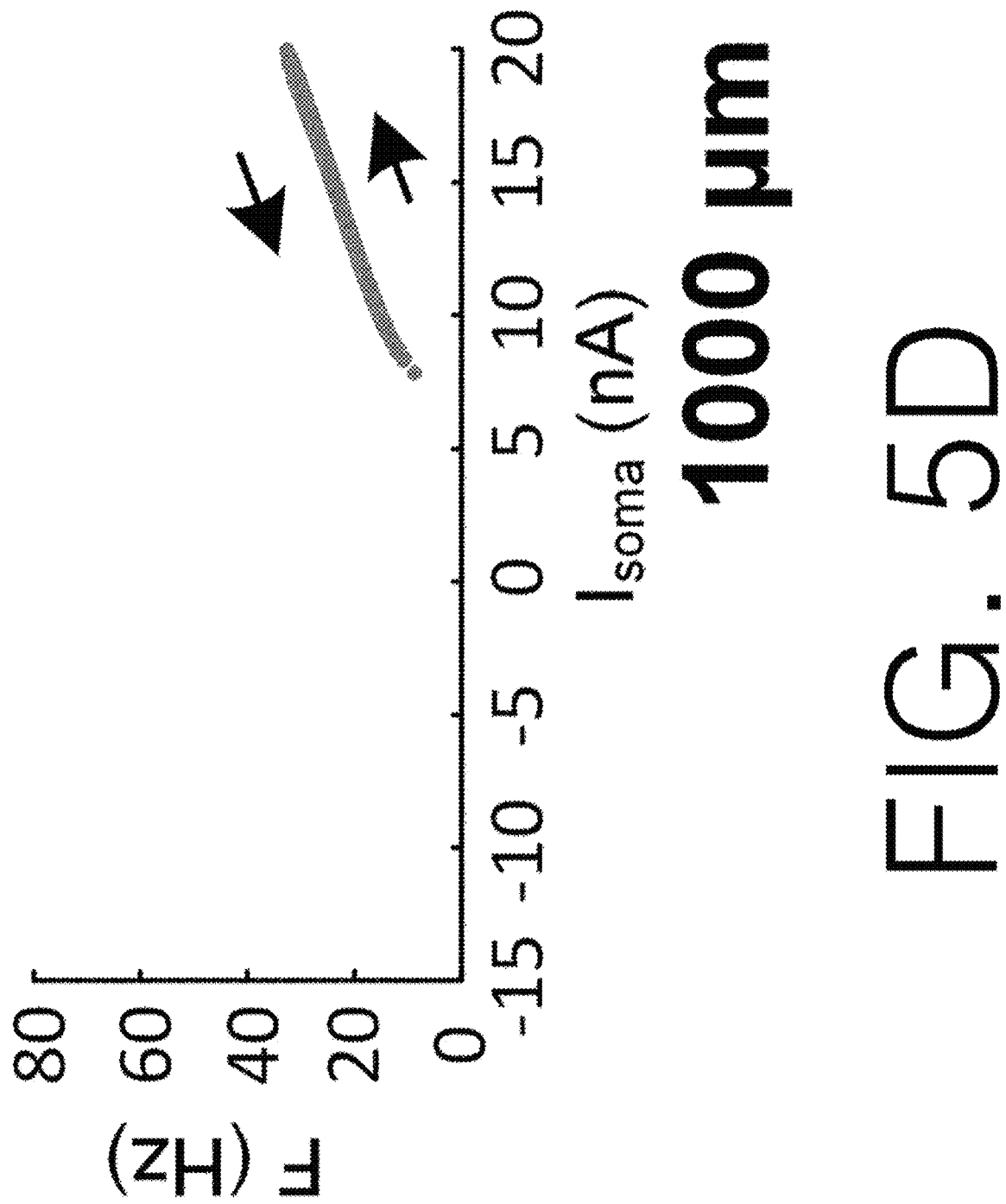
Figure 5E:
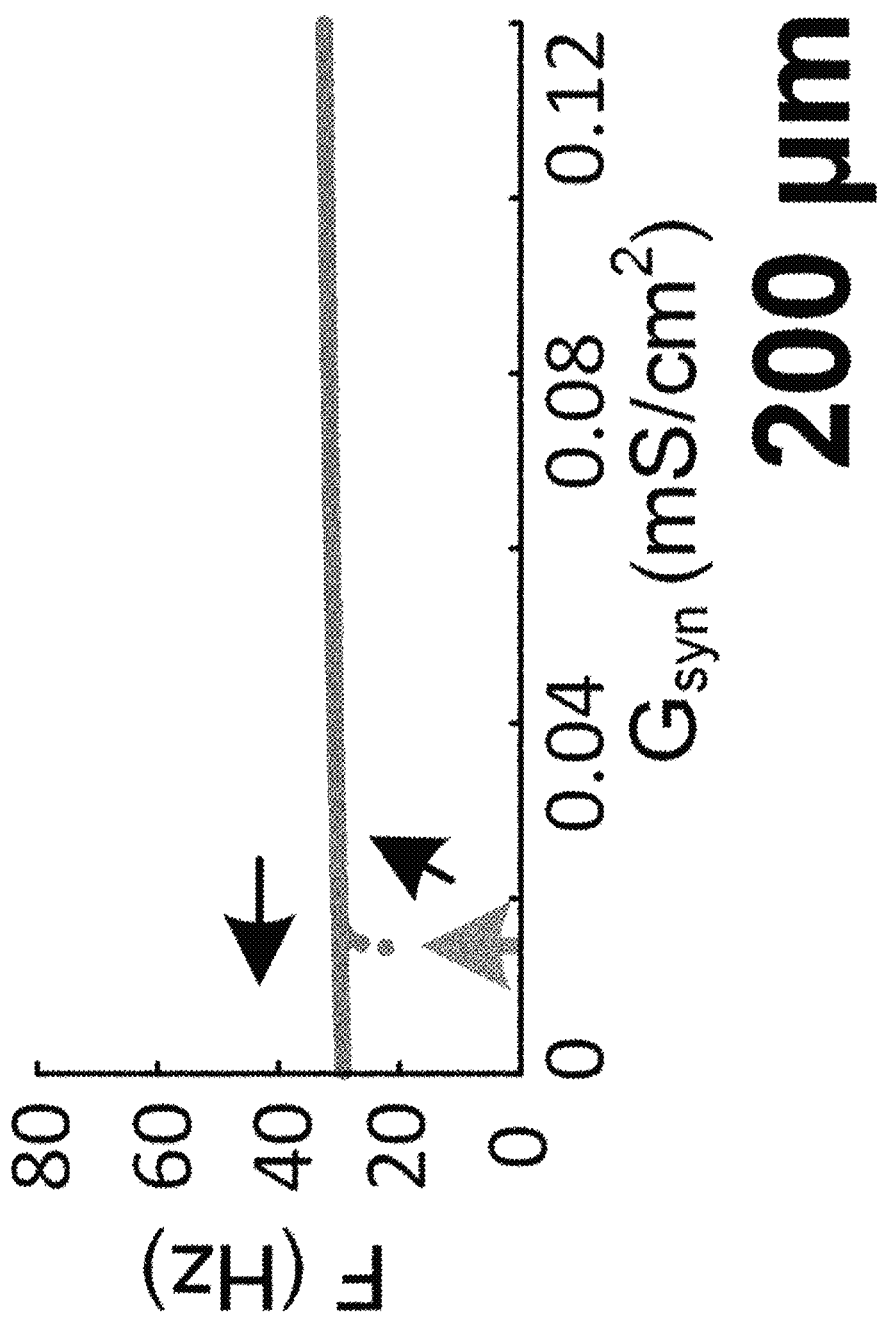
Figure 5F:
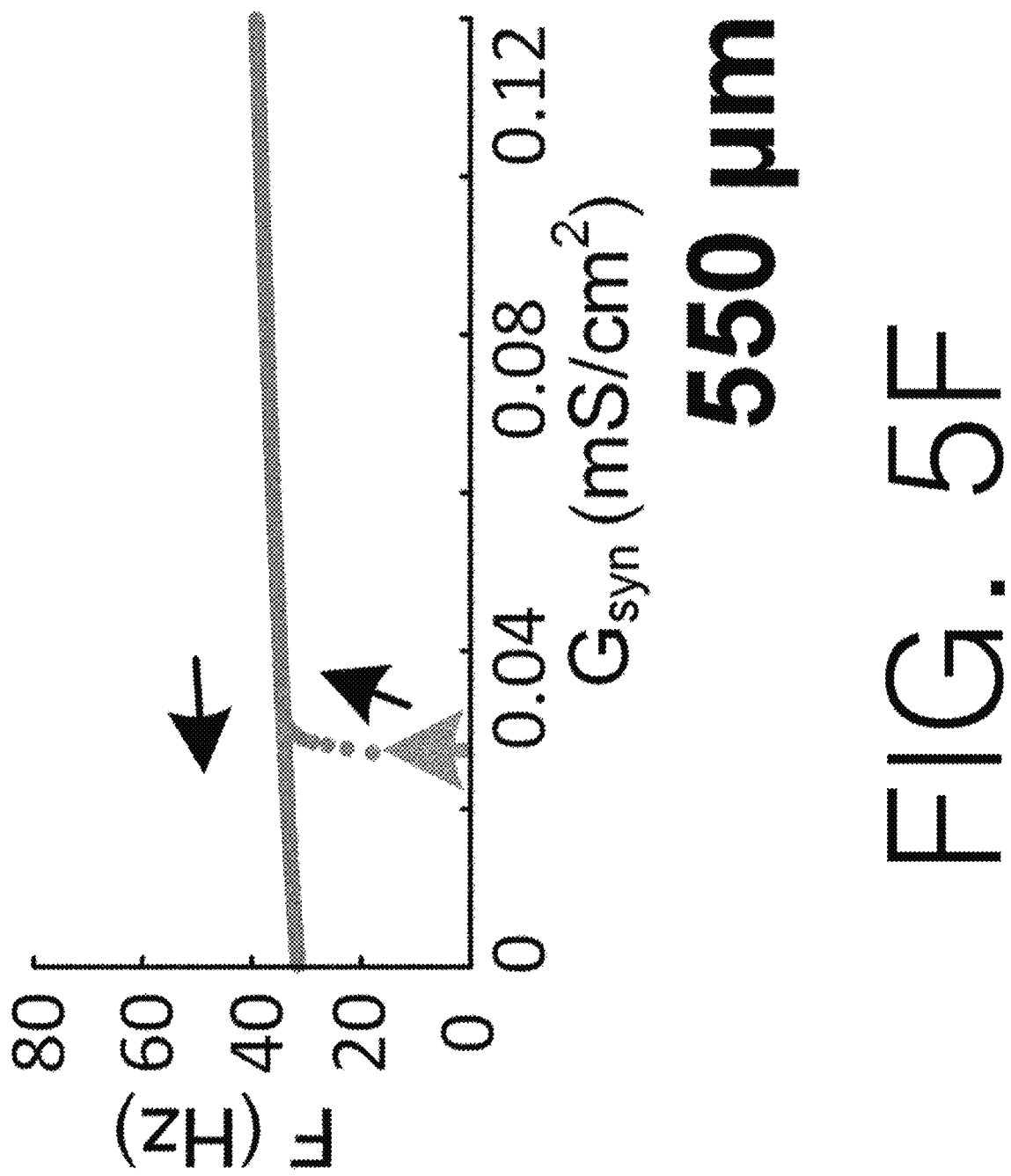
Figure 5G:
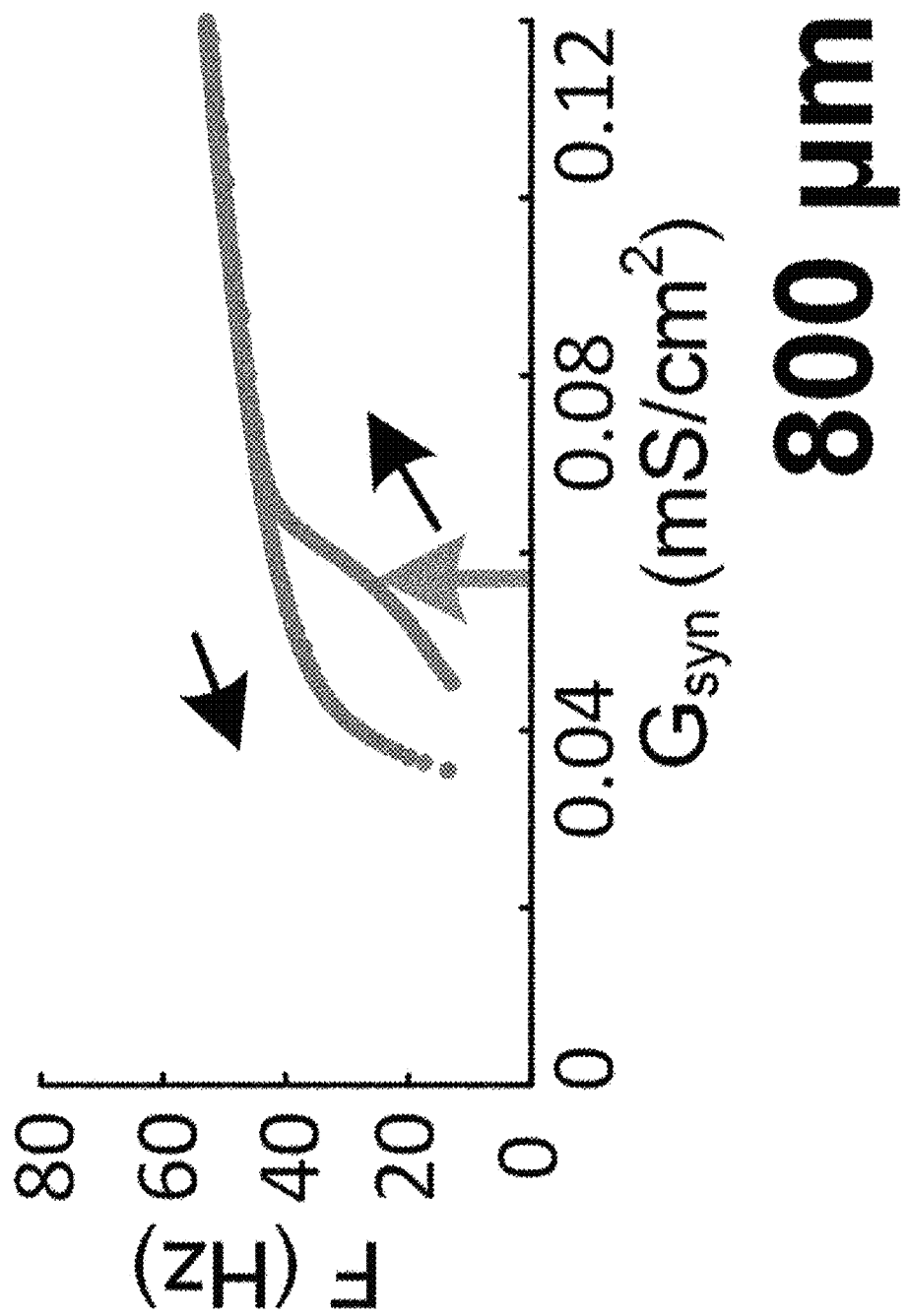
Figure 5H:
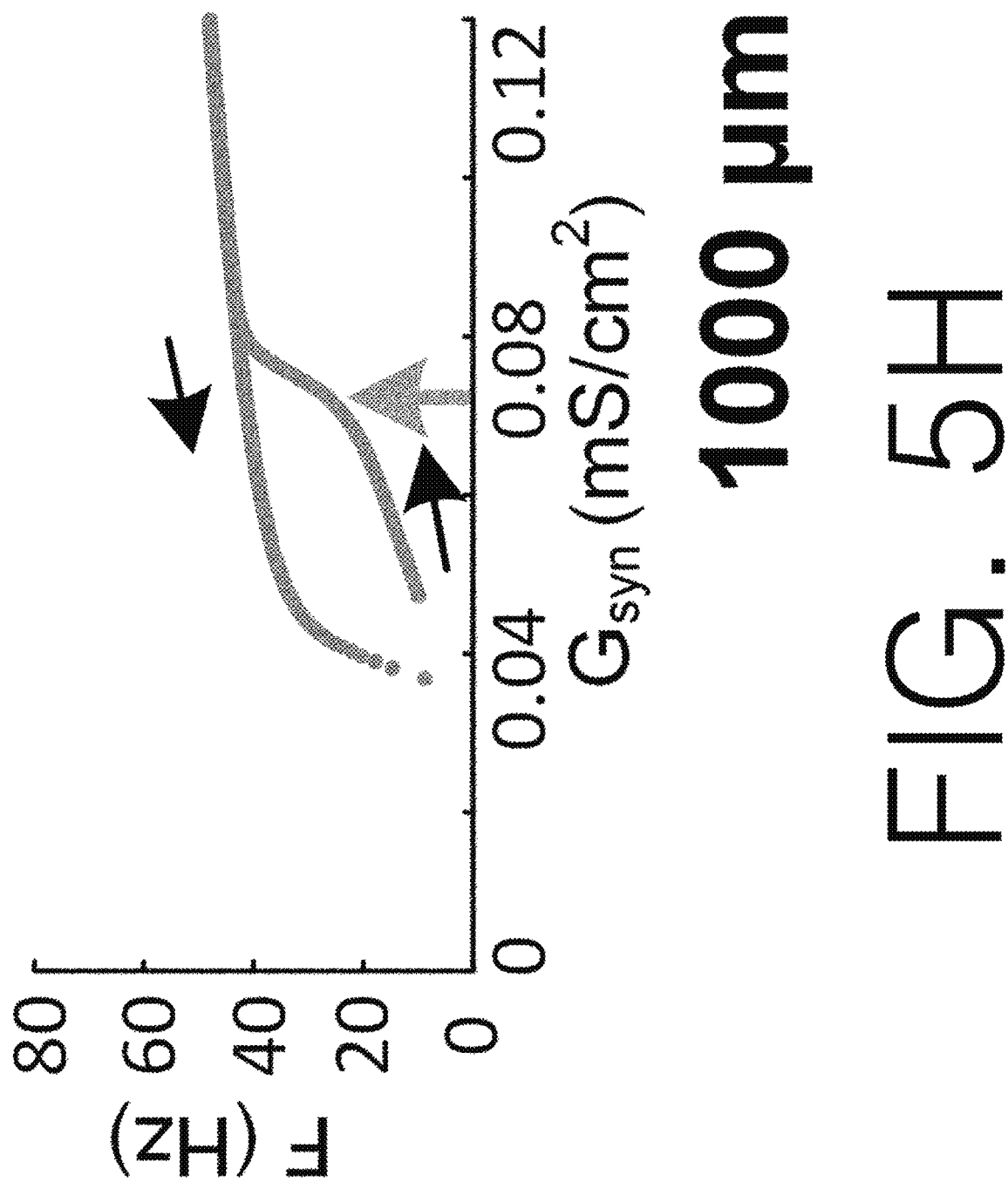

As a result, variations in $VA_{DS}^{DC}$ and $VA_{SD}^{AC}$ could be found to match the firing patterns when all three VA factors were constrained to their physiological ranges (FIGS. 3A-3H) with the PIC at non-physiological locations. For instance, the F-$I_{soma}$ curve at $D_{path}$=1000 µm in the physiological case (FIGS. 3D and 3H) could be reproduced at $D_{path}$=200 µm by decreasing only the $VA_{DS}^{DC}$ from 0.96 to 0.47 (FIGS. 5A and 5E), whereas the increase in both the $VA_{DS}^{DC}$ (0.63 0.876) and $VA_{SD}^{AC}$ (0.12 0.5) could lead to the same F-$I_{soma}$ curve at $D_{path}$=200 µm of the physiological case (FIG. 3A) at $D_{path}$=1000 µm (FIG. 5D). The strong dependency of the PIC activation and associated firing patterns on the VADCDC and $VA_{SD}^{AC}$, at all positions in the dendrites, indicates that all three voltage attenuation factors are necessary for biophysically realistic simulations of dendritic excitability.

Discussion

The high dimensionality of dendritic systems has made it challenging to get insights into whether and how the complex (directional and frequency-dependent) dendritic signaling contributes to the activation of voltage gated ion channels in dendrites. We have demonstrated using realistically reduced MN models that the asymmetry in voltage attenuation between the soma and the dendrites plays an essential role in determining the spatial activation pattern of voltage sensitive dendritic channels and associated somatic firing output. Our results also showed that voltage attenuation properties in several different types of neurons have an asymmetric profile that is remarkably similar to that in spinal MNs, suggesting that the essential role of this asymmetry for normal function may apply widely in neurons. All these results support the conclusion that the biophysically based asymmetry in signal propagation of the dendrites should be maintained in reduced models of neurons to physiologically represent the dendritic excitability.

Interaction of Voltage Attenuation Factors with Dendritic Excitability

The asymmetry of the dendritic signaling has been quantified by a ratio ($VA_{SD}^{DC}/VA_{DS}^{DC}$) of DC voltage attenuation factors between the soma and a single point in the dendrites [Kim H, Jones K E (2011) Asymmetric electrotonic coupling between the soma and dendrites alters the bistable firing behaviour of reduced models. J Comput Neurosci 30: 659-674]. This asymmetry index has been theoretically shown to be proportional to input resistance ($R_{N, D}$) at the same site of the dendrites, leading to the equation: $R_{N, D}(D_{path})=R_N*VA_{SD}^{DC}(D_{path})/VA_{DS}^{DC}(D_{path})$ [Kim H, Jones K E (2011) Asymmetric electrotonic coupling between the soma and dendrites alters the bistable firing behaviour of reduced models. J Comput Neurosci 30: 659-674].

In the present invention, the $VA_{DS}^{DC}$ was characterized between the soma and all points of the dendrites at the same distance. Our further analysis confirmed that the input resistance predicted with the equation well matched that measured directly from the anatomical model (FIG. 6).

Figure 6:
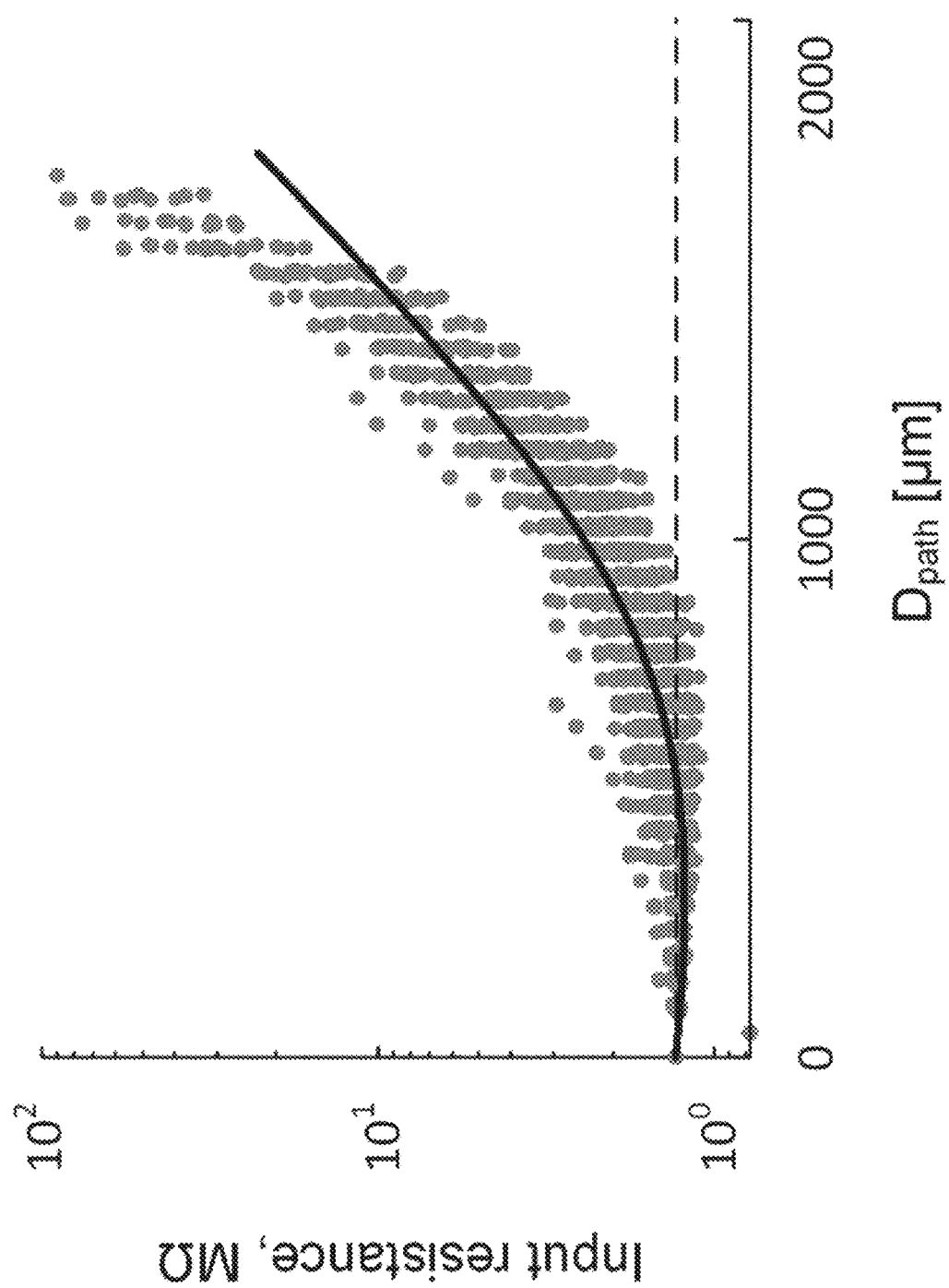
FIG. 6 shows dependence of input resistance on DC VA factor at dendrites.

FIG. 6 shows dependence of input resistance at the dendrites on the DC VA factors. In FIG. 6 input resistance ($R_{N, D}$, gray dots) was measured at individual points of the motoneuron dendrites at the same distance with respect to the total current injected to the dendrites (see the stimulation protocol used for the $VA_{DS}^{DC}$). The measured $R_{N, D}$ was superimposed by the $R_{N, D}$ (black line) that was predicted from fitting curves to the DC VA data using the equation ($R_{N, D}(D_{path})=R_N*VA_{SD}^{DC}(D_{path})/VA_{DS}^{DC}(D_{path})$ where $R_N$ is input resistance at the soma ($D_{path}$=0)). Note the agreement between the predicted and measured input resistance in the dendrites. The poor fit at the distal distance was attributed to the error between the $VA_{DS}^{DC}$ data and its fitting curve (see FIG. 1A). Our further analysis confirmed that the input resistance predicted with the equation well matched that measured directly from the anatomical model (FIG. 6).

This result indicates that in the case of 'point-to all points' the complex distribution of $R_{N, D}$ in the dendrites could also be captured by the same equation as for the case of 'point-to-point'. Based on this equation, the inverse relationship between the input threshold for plateau potential and the distance (FIG. 5A-5H) may be explained by the decreasing $R_{N, D}$ due to the increase in the $VA_{DS}^{DC}$ while holding the $VA_{SD}^{DC}$ in a physiological range. All these results indicate the direct influence of the DC VA properties on the activation of VGICs in the dendrites via determining the input resistance of the dendrites.

In the present invention, the attenuation of AC signals has been considered only for the propagation from the soma to the dendrites assuming the tonic synaptic inputs to the dendrites. The reason for that was not only due to the limitation of the current reduced modeling approach (see Methods), but also the impact of back-propagating action potentials on the dendritic excitability (compare current threshold for the plateau potential at the dendrites between FIGS. 2G and 2H). The action potentials passively propagating into the dendrites may have both excitatory and inhibitory effects on the activation of PIC channels by their spike and afterhyperpolarization (AHP) phase. The contribution of the passive dendrites to the back-propagation of action potentials was characterized with the $VA_{SD}^{AC}$ which negatively related to the signal frequency. Because the duration of AHP (e.g. 100 ms) is much longer than spike (e.g. 2 ms) in MNs, the inhibitory effect of back-propagating action potentials is expected to be dominant rather than the excitatory effect (compare the current threshold for PIC activation between FIGS. 2G and 2H). This inhibitory effect has been also shown to be important to shape the graded activation of plateau potentials, preventing from being activated in an all-or-none manner [Elbasiouny S M, Bennett D J, Mushahwar V K (2006) Simulation of $Ca^{2+}$ persistent inward currents in spinal motoneurones: mode of activation and integration of synaptic inputs. J Physiol 570: 355-374]. Due to exponential decay of the $VA_{SD}^{AC}$ with increasing distance, the back-propagating action potentials would hamper the activation of PIC channels around the soma more effectively. This implies that the VGICs in proximal dendritic sites would be even harder to be activated relative to distal sites. The similar non-uniformity of dendritic excitability, lower around the soma than distal dendrites, would be expected to occur in other major types of neurons in the brain because they showed the similar profile of the three VA factors as a function of the distance from the soma (FIGS. 1A-1F).

Many computational studies on the nonlinear firing patterns of MNs have suggested that L-type $Ca^{2+}$ channels mediating plateau potentials should be clustered in the dendrites away from the soma to generate the nonlinear firing patterns (hysteretic F-$I_{soma}$ relationship, bottom panel in FIG. 2H) [Carlin K P, Jones K E, Jiang Z, Jordan L M, Brownstone R M (2000) Dendritic L-type calcium currents in mouse spinal motoneurons: implications for bistability. Eur J Neurosci 12: 1635-1646, Booth V, Rinzel J (1995) A minimal, compartmental model for a dendritic origin of bistability of motoneuron firing patterns. J Comput Neurosci 2: 299-312]. However recent immunohistochemical study has shown the high densities of CaV1.3 clustered at both proximal (<100 μm) and distal sites (450~650 μm) from the soma [Ballou E W, Smith W B, Anelli R, Heckman C J (2006) Measuring dendritic distribution of membrane proteins. J Neurosci Methods 156: 257-266]. Furthermore the nucleated patch clamp recordings from an isolated soma without the dendrites have revealed the existence of Ca PIC channels even at the soma [Moritz A T, Newkirk G, Powers R K, Binder M D (2007) Facilitation of somatic calcium channels can evoke prolonged tail currents in rat hypoglossal motoneurons. J Neurophysiol 98: 1042-1047]. However, the distal PIC channels may be predominant in determining firing patterns during the current stimulation to the soma because of the higher excitability at the distal dendritic region relative to the proximal sites (FIGS. 3A-3F and 6).

The location dependent excitability in the dendrites was associated with input/output relationships of the model MN (FIGS. 3A-3F). While varying the location of PIC channels, the MN could reproduce all nonlinear firing patterns experimentally observed in MNs. Four firing types (i.e. Type I-IV) have been classified based on the F-I relationship during triangular current stimulation to the soma [Bennett D J, Li Y, Siu M (2001) Plateau potentials in sacrocaudal motoneurons of chronic spinal rats, recorded in vitro. J Neurophysiol 86: 1955-1971]. The Type I (linearly overlapping F-I relationship without self-sustained firing) or II firing (clockwise F-I relationship without self-sustained firing) was observed near the soma (<300 μm) whereas the Type III (linearly overlapping F-I relationship with self-sustained firing) or IV (counterclockwise F-I relationship with self-sustained firing) tended to occur in a dendritic region separated further away from the soma (>600 μm). A variance in firing patterns between MNs might be due to the different distribution of PIC channels in the dendrites, instead of variation in active channel properties.

Variability in Voltage Attenuation Properties and Dendritic Excitability

The distance dependent VA property of the dendrites is potentially tunable during normal behavior of neural networks. In a MN pool of cat medial gastrocnemius muscle, electrical properties including $R_N$, $\tau_m$, and AHP properties have been reported to be systematically related to the types (S-, FR- and FF-type) of MNs in a continuous manner [Zengel J E, Reid S A, Sypert G W, Munson J B (1985) Membrane electrical properties and prediction of motor-unit type of medial gastrocnemius motoneurons in the cat. J Neurophysiol 53: 1323-1344]. $R_N$ has been shown to have positive effect on the reduction of voltage attenuation by altering the spatial profile of individual VA factors: $VA_{SD}^{DC}$ [Kim H, Major L A, Jones K E (2009) Derivation of cable parameters for a reduced model that retains asymmetric voltage attenuation of reconstructed spinal motor neuron dendrites. J Comput Neurosci 27: 321-336], $VA_{SD}^{AC}$ [Kim H, Jones K E (2012) The retrograde frequency response of passive dendritic trees constrains the nonlinear firing behaviour of a reduced neuron model. PLoS One 7: e43654] and $VA_{DS}^{DC}$ (FIG. 1E). The $\tau_m$ and AHP properties may further influence the frequency dependent $VA_{SD}^{AC}$ because they are key parameters determining the shape of action potentials. In addition, the membrane electrical properties of individual neurons could be modulated by the different levels of background activity or shunting effect by synapses bombarding the dendritic trees [Destexhe A, Pare D (1999) Impact of network activity on the integrative properties of neocortical pyramidal neurons in vivo. J Neurophysiol 81: 1531-1547, Williams S R (2004) Spatial compartmentalization and functional 570 impact of conductance in pyramidal neurons. Nat Neurosci 7: 961-967]. Furthermore the properties of leak current channels determining the cable property might be targeted by a variety of diffusive neurotransmitters to manipulate the spatial dendritic excitability [Bockenhauer D, O'Kelly I, Zilberberg N (2001) Potassium leak channels and the KCNK family of two-P-domain subunits. Nat Rev Neurosci 2: 175-184, Nicoll R A, Malenka R C, Kauer J A (1990) Functional comparison of neurotransmitter receptor subtypes in mammalian central nervous system. Physiol Rev 70: 513-565]. In addition, dendritic morphology is not static, but dynamically varying in physiological conditions. Subtle changes in morphology may also occur due to a various pathological conditions [Yamada M, Wada Y, Tsukagoshi H, Otomo E, Hayakawa M (1988) A quantitative Golgi study of basal dendrites of hippocampal CA1 pyramidal cells in senile dementia of Alzheimer type. J Neurol Neurosurg Psychiatry 51: 1088-1090, Teskey G C, Monfils M H, Silasi G, Kolb B (2006) Neocortical kindling is associated with opposing alterations in dendritic morphology in neocortical layer V and striatum from neocortical layer III. Synapse 59: 1-9, Sousa N, Lukoyanov N V, Madeira M D, Almeida O F, Paula-Barbosa M M (2000) Reorganization of the morphology of hippocampal neurites and synapses after stress-induced damage correlates with behavioral improvement. Neuroscience 97: 253-266] or physical damage [Krenz NR, Weaver L C (1998) Changes in the morphology of sympathetic preganglionic neurons parallel the development of autonomic dysreflexia after spinal cord injury in rats. Neurosci Lett 243: 61-64]. All these electrical and morphological influences on the VA properties of the dendrites may significantly alter the spatial profile of dendritic excitability, enriching the repertoire of input/output functions of neurons within neural networks without changing physical location or activation properties of VGICs in the dendrites.

Implications to Reduced Modeling of Dendritic Neurons

The complex dendritic trees have been collapsed into the wide range of levels from multiple equivalent cables to one compartment in many reduced neuron models. The dendritic excitability in the reduced models depends on the reduction methods such as the conservation of surface area [Clements J D, Redman S J (1989) Cable properties of cat spinal motoneurones measured by combining voltage clamp, current clamp and intracellular staining. J Physiol 409: 63-87] or axial resistance [Bush P C, Sejnowski T J (1993) Reduced compartmental models of neocortical pyramidal cells. J Neurosci Methods 46: 159-166]. However, it has not been shown to what degree the local excitability in the reduced dendrites is comparable with the anatomical case, resulting in the sacrifice of traceability between the anatomical and reduced models [Hendrickson E B, Edgerton J R, Jaeger D (2011) The capabilities and limitations of conductance-based compartmental neuron models with reduced branched or unbranched morphologies and active dendrites. J Comput Neurosci 30: 301-321]. In the present invention, the inventors have shown the close relationship between voltage attenuation factors and dendritic excitability at all distances from the soma (FIGS. 3A-3F and 6). This finding could provide a theoretical basis for physiologically representing the excitability of the dendrite in the reduced neuron models on the physical domain (i.e. $D_{path}$), not on the electrical domain (i.e. length constant, $\lambda$) used up to date. Thereby the identification of voltage attenuation factors governing spatial heterogeneity of dendritic excitability may bridge the gap between the anatomically reconstructed and reduced neuron models.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

What is claimed is:

1. A method of activing a neuron based on a reduced model for the neuron, comprising:
    confirming asymmetry in signal propagation between a soma and dendrites of the neuron which is being modeled;
    confirming dendritic excitability of the neuron;
    identifying a relationship between the asymmetry in signal propagation and the dendritic excitability;
    determining the reduced model of the neuron using the relationship between the asymmetry in signal propagation and the dendritic excitability;
    adjusting a magnitude of a voltage to be applied to the neuron based on the reduced model;
    generating a command signal using the adjusted magnitude of the voltage; and
    applying the command signal to the soma of the neuron, wherein the relationship between the asymmetry in signal propagation and the dendritic excitability comprises:
    increases in signal attenuation from the soma to the dendrites increase an activation threshold of a persistent inward current (PIC) dispersed over the dendrites (hypo-excitability); and
    increases in signal attenuation from the dendrites to the soma decrease the activation threshold of the PIC dispersed over the dendrites (hyper-excitability).

2. The method as set forth in claim 1, wherein the asymmetry in the signal propagation comprises spatial profiles of three voltage attenuation factors, wherein voltage attenuation factors have neuron voltage profiles in response to steady current injected at the soma ($VA_{SD}^{DC}$), action potentials propagating from an initial segment and the soma into the dendrites ($VA_{SD}$ AC), and steady synaptic inputs and plateau potential generated by voltage-gated ion channels (VGICs) in the dendrites ($VA_{DS}^{DC}$).

3. The method as set forth in claim 2, wherein the $VA_{SD}^{DC}$, the $VA_{SD}^{AC}$ and the $VA_{Ds}^{DC}$ are determined using path length ($D_{path}$) from the soma according to equations 1 to 3 respectively as below:

$$VA_{SD}^{DC}(D_{path}) = \exp\left(-\frac{D_{path}}{\lambda_{SD}^{DC}}\right) \quad (1)$$

$$VA_{SD}^{AC}(D_{path}) = \exp\left(-\frac{D_{path}}{\lambda_{SD}^{AC}}\right) \quad (2)$$

$$VA_{DS}^{DC}(D_{path}) = \frac{1}{1 - \exp\left(\frac{-\alpha_1}{\alpha_2}\right) + \exp\left(\frac{D_{path} - \alpha_1}{\alpha_2}\right)} \quad (3)$$

where $\lambda_{SD}^{DC}$ and $\lambda_{SD}^{AC}$ are voltage decay constants for voltage attenuation factors $VA_{SD}^{DC}$ and $VA_{SD}^{Ac}$ respectively, and where $\alpha_1$ approximately represents a distance at the $VA_{DS}^{Dc}=0.5$ and $\alpha_2$ indicates the variation in a slope of an inverse-sigmoid curve of the $VA_{DS}^{DC}$ at $\alpha_1$.

4. The method as set forth in claim 2, wherein the asymmetry in the signal propagation is quantified by a ratio ($VA_{SD}^{DC}/VA_{DS}^{DC}$) of DC voltage between the soma and a single point in the dendrites as below:

$$R_{N,D}(D_{path}) = R_N * VA_{SD}^{DC}(D_{path})/VA_{DS}^{DC}(D_{path}),$$

wherein $R_{N,D}$ is input resistance ($R_{N,D}$) at the same site of the dendrites, and $R_N$ is a somatic input resistance of the neuron.

5. A method of activating a neuron based on a reduced model for the neuron, comprising:
    determining voltage attenuation factors which represent properties of signal propagation between dendrites and a soma of the neuron and is represented as functions of distance from the soma; and
    determining a plurality of passive parameters at a pre-determined path length using system parameters defined from an anatomical model comprising the voltage attenuation factors at the pre-determined path length;
    determining the reduced model of the neuron using the plurality of passive parameters;
    adjusting a magnitude of a voltage to be applied to the neuron based on the reduced model;
    generating a command signal using the adjusted magnitude of the voltage; and
    applying the command signal to the soma of the neuron, wherein the voltage attenuation factors comprise $VA_{SD}^{DC}$ and $VA_{SD}^{AC}$
    which are DC and AC components from the soma to dendrites respectively, and $VA_{SD}^{DC}$ which is a DC component from the dendrites to the soma.

6. The method as set forth in claim 5, wherein the voltage attenuation factors representing signal propagation of the dendrites is defined as a ratio of voltage at measurement site to voltage at a current injection site in a passive membrane condition.

7. The method as set forth in claim 5, the $VA_{SD}^{DC}$ is measured at dendrites for propagation of steady current injected at the soma.

8. The method as set forth in claim 5, wherein the $VA_{SD}^{DC}$ is measured for propagation of steady synaptic inputs and persistent inward current generated by voltage gated ion channels (VGICs) that are distributed over all branches of the dendrites at the same distance from the soma.

9. The method as set forth in claim 5, wherein the $VA_{SD}^{AC}$ is measured for action potentials propagating from initial segment and the soma into the dendrites.

10. The method as set forth in claim 5, wherein the $VA_{SD}^{DC}$ and $VA_{SD}^{AC}$ are fitted by a single exponential function with voltage decay constant ($\lambda_{SD}^{DC}$ and $\lambda_{SD}^{AC}$).

11. The method as set forth in claim 10, wherein the $VA_{SD}^{DC}$ and $VA_{SD}^{AC}$ are determined by equations 1 and 2 as below:

$$VA_{SD}^{DC}(D_{path}) = \exp\left(-\frac{D_{path}}{\lambda_{SD}^{DC}}\right) \quad (1)$$

$$VA_{SD}^{AC}(D_{path}) = \exp\left(\frac{D_{path}}{\lambda_{SD}^{AC}}\right) \quad (2)$$

where $\lambda_{SD}^{DC}$ and $\lambda_{SD}^{AC}$ are voltage decay constants for voltage attenuation factors $VA_{SD}^{DC}$ and $VA_{SD}^{AC}$ respectively.

12. The method as set forth in claim 5, wherein the $VA_{SD}^{DC}$ is fitted with a modified Boltzmann equation with two parameters $\alpha_1$ and $\alpha_2$, wherein $\alpha_1$ approximately represents the distance at the $VA_{SD}^{DC}=0.5$ and $\alpha_2$ indicates a variation in a slope of an inverse-sigmoid curve of the $VA_{SD}^{DC}$ at $\alpha_1$.

13. The method as set forth in claim 12, wherein the $VA_{SD}^{DC}$ is determined by equation 3 as below:

$$VA_{DS}^{DC}(D_{path}) = \frac{1}{1 - \exp\left(\frac{-\alpha_1}{\alpha_2}\right) + \exp\left(\frac{D_{path} - \alpha_1}{\alpha_2}\right)}. \quad (3)$$

14. The method as set forth in claim 5, wherein the system parameters comprise the voltage attenuation factors, somatic input resistance of the neuron ($R_N$) and membrane time constant of the neuron ($\tau_m$).

15. The method as set forth in claim 13, wherein the plurality of passive parameter is determined at a specific $D_{path}$ from the soma by solving the inverse equations for the system parameters.

16. The method as set forth in claim 15, wherein the passive parameters comprise somatic membrane conductance and dendritic membrane conductance ($G_m,s$ and $G_{m,D}$), somatic membrane capacitance and dendritic membrane capacitance ($G_m,s$ and $G_{m,D}$), and one coupling conductance ($G_C$) between the soma and dendrite.

17. The method as set forth in claim 16 further comprises determining two-compartmental neuron model consisting of a somatic compartment and a dendritic compartment that are coupled with the single conductance ($G_C$), wherein the somatic compartment has the $G_{m,s}$ and the $C_{m,S}$ as passive dynamics, and the dendritic compartment has the $G_{m,D}$ and the $C_{m,D}$ as passive dynamics.

18. The method as set forth in claim 16, wherein the determining a plurality of passive parameter comprises determining the plurality of passive parameter by equation 4 to 8 as below:

$$G_{m,S} = \frac{1 - VA_{DS}^{DC}}{r_N(1 - VA_{SD}^{DC} VA_{DS}^{DC})} \quad (4)$$

$$G_{m,D} = \frac{p VA_{DS}^{DC}(1 - VA_{SD}^{DC})}{(1-p)r_N VA_{SD}^{DC}(1 - VA_{SD}^{DC} VA_{DS}^{DC})} \quad (5)$$

$$G_C = \frac{p VA_{DS}^{DC}}{r_N(1 - VA_{SD}^{DC} VA_{DS}^{DC})} \quad (6)$$

$$C_{m,D} = \frac{1}{\omega(1-p)} \sqrt{\frac{G_C^2}{(VA_{SD}^{AC})^2} - \{G_C + G_{m,D}(1-p)\}^2} \quad (7)$$

$$C_{m,S} = \frac{\tau_m\{p(1-p)\tau_m G_{m,S} G_{m,D} + p G_{m,S}(\tau_m G_C - C_{m,D}) + p^2 G_{m,S} C_{m,D} + (1-p)(\tau_m G_C G_{m,D} - G_C C_{m,D}\}}{p\{(1-p)(\tau_m G_{m,D} - C_{m,D}) + \tau_m G_C\}} \quad (8)$$

wherein $r_N$ is the input resistance ($R_N$) normalized with the surface area of somatic compartment, $\Omega\cdot$ is the maximum frequency component in an action potential, and p is the ratio of somatic to total surface area of the reduced model.

\* \* \* \* \*